US008515679B2

(12) United States Patent
Rabinowitz et al.

(10) Patent No.: US 8,515,679 B2
(45) Date of Patent: *Aug. 20, 2013

(54) SYSTEM AND METHOD FOR CLEANING NOISY GENETIC DATA AND DETERMINING CHROMOSOME COPY NUMBER

(75) Inventors: Matthew Rabinowitz, Portola Valley, CA (US); Milena Banjevic, New York, NY (US); Zachary Demko, Somerville, MA (US); David Scott Johnson, Portola Valley, CA (US); Dusan Kijacic, New York, NY (US); Dimitri Petrov, Menlo Park, CA (US); Josh Sweetkind-Singer, San Jose, CA (US); Jing Xu, Springfield, NJ (US)

(73) Assignee: Natera, Inc., San Carlos, CA (US)

( * ) Notice: Subject to any disclaimer, the term of this patent is extended or adjusted under 35 U.S.C. 154(b) by 955 days.

This patent is subject to a terminal disclaimer.

(21) Appl. No.: 12/076,348

(22) Filed: Mar. 17, 2008

(65) Prior Publication Data
US 2008/0243398 A1     Oct. 2, 2008

Related U.S. Application Data

(63) Continuation-in-part of application No. 11/496,982, filed on Jul. 31, 2006, and a continuation-in-part of application No. 11/603,406, filed on Nov. 22, 2006, and a continuation-in-part of application No. 11/634,550, filed on Dec. 6, 2006.

(60) Provisional application No. 60/846,610, filed on Sep. 22, 2006, provisional application No. 60/817,741, filed on Jun. 30, 2006, provisional application No. 60/789,506, filed on Apr. 4, 2006, provisional application No. 60/774,976, filed on Feb. 21, 2006, provisional application No. 60/754,396, filed on Dec. 29, 2005, provisional application No. 60/742,305, filed on Dec. 6, 2005, provisional application No. 60/918,292, filed on Mar. 16, 2007, provisional application No. 60/926,198, filed on Apr. 25, 2007, provisional application No. 60/932,456, filed on May 31, 2007, provisional application No. 60/934,441, filed on Jun. 13, 2007, provisional application No. 61/003,101, filed on Nov. 13, 2007, provisional application No. 61/008,637, filed on Dec. 21, 2007, provisional application No. 60/739,882, filed on Nov. 26, 2005, provisional application No. 60/703,415, filed on Jul. 29, 2005.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................. 702/19; 702/22; 703/11; 703/12

(58) Field of Classification Search
None
See application file for complete search history.

(56) References Cited

U.S. PATENT DOCUMENTS

| 5,635,366 A | 6/1997 | Cooke et al. |
| 5,824,467 A | 10/1998 | Mascarenhas |
| 5,860,917 A | 1/1999 | Comanor |
| 5,994,148 A | 11/1999 | Stewart et al. |
| 6,025,128 A | 2/2000 | Veltri et al. |
| 6,108,635 A | 8/2000 | Herren |
| 6,180,349 B1 | 1/2001 | Ginzinger |
| 6,258,540 B1 | 7/2001 | Lo et al. |
| 6,489,135 B1 | 12/2002 | Parrott |
| 6,720,140 B1 | 4/2004 | Hartley et al. |
| 6,807,491 B2 | 10/2004 | Pavlovic et al. |

(Continued)

FOREIGN PATENT DOCUMENTS

| EP | 1 524 321 | 4/2005 |
| WO | WO 03/031646 | 4/2003 |

(Continued)

OTHER PUBLICATIONS

Zhou et al. (Cancer Research, 2004, 64, 3060-3071).*
Colella S. et al., (2007), Nucl. Acids Res. 35(6):2013-2025.
Freeman J. et al., (2006), Genome Res. 16(8):949-961.
Beaumont M. et al., (2004), Nature Rev. Genet. 5(4):251-261.
Ogino S. et al., (2004), J. Mole. Diagnostics, 6(1):1-9.
Written Opinion of the International Searching Authority, Appl. No. PCT/US2008/003547, Mailed on: Apr. 15, 2009.
Beerenwinkel et al. (2003), Bioinformatics, 19 Supp. 3:i16-i25.
Breithaupt (2001), European Molecular Biology Organization, 21(61):465-467.

(Continued)

*Primary Examiner* — Larry D Riggs, II
(74) *Attorney, Agent, or Firm* — Zachary P. Demko; Scott R. Bortner; Vicki L. Healy

(57) ABSTRACT

Disclosed herein is a system and method for increasing the fidelity of measured genetic data, for making allele calls, and for determining the state of aneuploidy, in one or a small set of cells, or from fragmentary DNA, where a limited quantity of genetic data is available. Genetic material from the target individual is acquired, amplified and the genetic data is measured using known methods. Poorly or incorrectly measured base pairs, missing alleles and missing regions are reconstructed using expected similarities between the target genome and the genome of genetically related individuals. In accordance with one embodiment of the invention, incomplete genetic data from an embryonic cell are reconstructed at a plurality of loci using the more complete genetic data from a larger sample of diploid cells from one or both parents, with or without haploid genetic data from one or both parents. In another embodiment of the invention, the chromosome copy number can be determined from the measured genetic data of a single or small number of cells, with or without genetic information from one or both parents. In another embodiment of the invention, these determinations are made for the purpose of embryo selection in the context of in-vitro fertilization. In another embodiment of the invention, the genetic data can be reconstructed for the purposes of making phenotypic predictions.

26 Claims, No Drawings

(56) References Cited

U.S. PATENT DOCUMENTS

| | | |
|---|---|---|
| 6,958,211 B2 | 10/2005 | Vingerhoets et al. |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg |
| 7,297,485 B2 | 11/2007 | Bornarth |
| 7,332,277 B2 | 2/2008 | Dhallan |
| 7,442,506 B2 | 10/2008 | Dhallan |
| 7,459,273 B2 | 12/2008 | Jones et al. |
| 7,645,576 B2 | 1/2010 | Lo et al. |
| 7,700,325 B2 | 4/2010 | Cantor et al. |
| 7,718,370 B2 | 5/2010 | Dhallan |
| 7,727,720 B2 | 6/2010 | Dhallan |
| 7,805,282 B2 | 9/2010 | Casey et al. |
| 7,838,647 B2 | 11/2010 | Hahn et al. |
| 7,888,017 B2 | 2/2011 | Quake et al. |
| 8,008,018 B2 | 8/2011 | Quake et al. |
| 8,024,128 B2 | 9/2011 | Rabinowitz et al. |
| 2003/0009295 A1 | 1/2003 | Markowitz |
| 2003/0065535 A1 | 4/2003 | Karlov |
| 2003/0077586 A1 | 4/2003 | Pavlovic et al. |
| 2003/0101000 A1 | 5/2003 | Bader |
| 2003/0228613 A1 | 12/2003 | Bornarth |
| 2004/0033596 A1 | 2/2004 | Threadgill et al. |
| 2004/0137470 A1 | 7/2004 | Dhallan et al. |
| 2004/0236518 A1 | 11/2004 | Pavlovic |
| 2004/0259100 A1 | 12/2004 | Gunderson |
| 2005/0009069 A1 | 1/2005 | Liu |
| 2005/0049793 A1 | 3/2005 | Paterlini-Brechot |
| 2005/0142577 A1 | 6/2005 | Jones et al. |
| 2005/0144664 A1 | 6/2005 | Smith |
| 2005/0250111 A1 | 11/2005 | Xie et al. |
| 2005/0255508 A1 | 11/2005 | Casey et al. |
| 2005/0272073 A1 | 12/2005 | Vaisberg |
| 2006/0040300 A1 | 2/2006 | Dapprich |
| 2006/0052945 A1 | 3/2006 | Rabinowitz et al. |
| 2006/0057618 A1 | 3/2006 | Piper |
| 2006/0121452 A1 | 6/2006 | Dallan |
| 2006/0134662 A1 | 6/2006 | Pratt et al. |
| 2006/0141499 A1 | 6/2006 | Sher |
| 2006/0216738 A1 | 9/2006 | Wada et al. |
| 2006/0229823 A1 | 10/2006 | Liu |
| 2007/0027636 A1 | 2/2007 | Rabinowitz et al. |
| 2007/0059707 A1 | 3/2007 | Cantor et al. |
| 2007/0122805 A1 | 5/2007 | Cantor et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0207466 A1 | 9/2007 | Cantor |
| 2007/0212689 A1 | 9/2007 | Bianchi |
| 2007/0259351 A1 | 11/2007 | Chinitz |
| 2008/0020390 A1 | 1/2008 | Mitchell |
| 2008/0070792 A1 | 3/2008 | Stoughton |
| 2008/0102455 A1 | 5/2008 | Poetter |
| 2008/0138809 A1 | 6/2008 | Kapur |
| 2008/0182244 A1 | 7/2008 | Tafas |
| 2009/0029377 A1 | 1/2009 | Lo et al. |
| 2009/0099041 A1 | 4/2009 | Church et al. |
| 2010/0112590 A1 | 5/2010 | Lo et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0256013 A1 | 10/2010 | Quake et al. |
| 2010/0285537 A1 | 11/2010 | Zimmermann |
| 2011/0033862 A1 | 2/2011 | Rabinowitz et al. |
| 2011/0092763 A1 | 4/2011 | Rabinowitz et al. |
| 2011/0178719 A1 | 7/2011 | Rabinowitz et al. |
| 2011/0288780 A1 | 11/2011 | Rabinowitz et al. |
| 2012/0122701 A1 | 5/2012 | Ryan et al. |
| 2012/0185176 A1 | 7/2012 | Rabinowitz et al. |
| 2012/0270212 A1 | 10/2012 | Rabinowitz et al. |

FOREIGN PATENT DOCUMENTS

| | | |
|---|---|---|
| WO | 2007062164 A | 5/2007 |
| WO | WO 2007/057647 | 5/2007 |
| WO | WO 2007/070482 | 6/2007 |
| WO | WO 2007/132167 | 11/2007 |
| WO | WO 2008/115497 | 9/2008 |
| WO | WO 2009/013492 | 1/2009 |
| WO | WO 2009/013496 | 1/2009 |
| WO | WO 2009/019455 | 2/2009 |
| WO | WO 2009/105531 | 8/2009 |
| WO | WO 2009/146335 | 12/2009 |
| WO | WO 2010/017214 | 2/2010 |
| WO | WO 2011/041485 | 4/2011 |
| WO | WO 2011/146632 | 11/2011 |
| WO | WO 2012/088456 | 6/2012 |
| WO | WO 2012/108920 | 8/2012 |

OTHER PUBLICATIONS

Fiorentino et al. (2004), Mo. Human Reproduction, 10(6):445-460.
Fiorentino et al. (2005), European J. Human Genetics, 13:953-958.
Fiorentino et al. (2006), Human Reproduction, 21(3):670-684.
Harper and Wells (1999), Prenatal Diagnosis, 19:1193-1199.
Hellani et al. (2005), Reproductive BioMedicine Online, 10(3):376-380.
Hu et al. (2004), Molecular Human Reproduction, 10(4):283-289.
Kijak et al. (2003), HIV Medicine, 4:72-78.
Kuliev and Verlinsky (2003), Reproductive BioMedicine Online, 8(2):229-235.
Munne et al. (2004), Chromosome Abnormalities in Human Embryos, In BOOK, 355-377.
Rabinowitz et al. (2006), Bioinformatics, 22(5):541-549.
Rechitsky et al. (2004), Reproductive BioMedicine Online, 9(2):210-221.
Renwick et al. (2006), Reproductive BioMedicine Online, 13(1):110-119.
Sandler (2000), Science, 287(5460):1977-1978.
Slater et a. (2005), Am. J. Human Genetics, 77:709-726.
Verlinsky et al. (2004), Fertility and Sterility, 82(2):302-303.
Wells (2004), European J. of Obstetrics & Gynecology, 115S, S97-S101.
Wells, *Microarray for Analysis and Diagnosis of Human Embryos, 12th International Congress on Prenatal Diagnosis and Therapy*, Budapest, Hungary, 9-17(Jun. 24-27, 2004).
European Examination Report, Application No. EP08742125.1, Date: Feb. 12, 2010.
Abidi et al., Leveraging XML-based Electronic Medical Records to Extract Experimental Clinical Knowledge, International Journal of Medical Informatics, 68, p. 187-203 (Dec. 18, 2002).
Allaire, Mate Selection by Selection Index Theory, Theor. Appl. Genet., 57, p. 267-272 (Nov. 1980).
Bada et al., Computational Modeling of Structural Experimental Data, Methods in Enzymology, 317, p. 470-491 (May 2000).
Beerenwinkel et al., Geno2pheno: Estimating Phenotypic Drug Resistance from HIV-1 Genotypes, Nucleic Acids Research, 31 (13), p. 3850-3855 (Jul. 2003).
Bodenreider, The Unified Medical Language System (UMLS): Integrating Biomedical Terminology, Nucleic Acids Research, 32, p. D267-D270 (Jan. 2004).
Chu et al., Statistical Model for Whole Genome Sequencing and its Application to Minimally Invasive Diagnosis of Fetal Genetic Disease, Bioinformatics, 25(10), p. 1244-1250 (May 15, 2009).
Coyle et al., Standards for Detailed Clinical Models as the Basis for Medical Data Exchange and Decision Support, International Journal of Medical Informatics, 69 (2), p. 157-174 (Mar. 2003).
Daruwala et al., A Versatile Statistical Analysis Algorithm to Detect Genome Copy Number Variation, PNAS, 101(46), p. 16292-16297 (Nov. 16, 2004).
Donoso et al., Current Value of Preimplantation Genetic Aneuploidy Screening in IVF, Hum. Reprod. Update, 13 (1), p. 15-25 (Jan./Feb. 2007).
Fixed Medium, Academic Press Dictionary of Science and Technology, Retrieved from www.credoreference.com/entry/apdst/fixed_medium (Sep. 1992, Accessed on Nov. 18, 2009).

Hollox et al., Extensive Normal Copy Number Variation of a β-Defensin Antimicrobial-Gene Cluster, Am. J. Hum. Genet., 73 (3), p. 591-600 (Sep. 2003).
McCray et al., Aggregating UMLS Semantic Types for Reducing Conceptual Complexity, Medinfo2001, 84, p. 216-220 (Jun. 2001).
Nannya et al., A Robust Algorithm for Copy Number Detection Using High-density Oligonucleotide Single Nucleotide Polymorphism Genotyping Arrays, Cancer Res, 65(14), p. 6071-6079 (Jul. 15, 2005).
Page et al., Chromosome Choreography: The Meiotic Ballet, Science, 301, p. 785-789 (Aug. 8, 2003).
Perry et al., The Fine-Scale and Complex Architecture of Human Copy-Number Variation, The American Journal of Human Genetics, 82, p. 685-695 (Mar. 2008).
Pfaffl et al., Relative Expression Software Tool (REST©) for Group-Wise Comparison and Statistical Analysis of Relative Expression Results in Real-Time PCR, Nucleic Acids Research, 30(9), p. 1-10 (May 1, 2002).
Sebat et al., Strong Association of De Novo Copy Number Mutations with Autism, Science, 316, p. 445-449 (Apr. 20, 2007).
Sweetkind-Singer, Log-Penalized Linear Regression, International Symposium on Information Theory, p. 286 (Jun. 29-Jul. 4, 2003).
Stephens, et al., A Comparison of Bayesian Methods for Haplotype Reconstruction from Population Genotype Data, Am. J. Human Genetics, 73 (5), p. 1162-1169 (Nov. 1, 2003).
Stevens et al., Ontology-Based Knowledge Representation for Bioinformatics, Briefings in Bioinformatics, 1 (4), p. 398-414 (Nov. 2000).
Steyerberg et al., Application of Shrinkage Techniques in Logistic Regression Analysis: A Case Study, Statistical Neerlandica, 55 (1), p. 76-88 (Mar. 2001).
Strom et al., Neonatal Outcome of Preimplantation Genetic Diagnosis by Polar Body Removal: the first 109 infants, Pediatrics, (4), p. 650-653 (Oct. 2000).
Troyanskaya et al., A Bayesian Framework for Combining Heterogeneous Data Sources for Gene Function Prediction, Proc. Nat. Academy of Sci., 100(14), p. 8348-8353 (Jul. 8, 2003).
Wilton, Preimplantation Genetic Diagnosis and Chromosome Analysis of Blastomeres Using Comparative Genomic Hybridization, Hum. Record. Update, (11) 1, p. 33-41 (Jan./Feb. 2005).
Yeh et al., Knowledge Acquisition, Consistency Checking and Concurrency Control for Gene Ontology (GO), Bioinformatics, 19(2), p. 241-248 (Jan. 2003).
Zhao et al., An Integrated View of Copy Number and Allelic Alterations in the Cancer Genome Using Single Nucleotide Polymorphism Arrays, Cancer Research, 64, p. 3060-3071 (May 1, 2004).
Extended European Search Report in 06 838 311.6 dated Dec. 30, 2008.
PCT International Preliminary Report on Patentability based on PCT/US2006/045281 dated May 27, 2008.
PCT International Search Report based on PCT/US2006/045281 dated Sep. 28, 2007.
PCT International Search Report based on PCT/US2009/034506 dated Jul. 8, 2009.
PCT International Search Report based on PCT/US2009/045335 dated Jul. 27, 2009.
PCT International Search Report based on PCT/US2009/052730 dated Sep. 28, 2009.
PCT International Search Report based on PCT/US2010/050824 dated Nov. 15, 2010.
Office Action in U.S. Appl. No. 11/004,274 mailed Nov. 24, 2009.
Office Action in U.S. Appl. No. 11/004,274 mailed Feb. 4, 2009.
Office Action in U.S. Appl. No. 11/004,274 mailed May 13, 2008.
Office Action in U.S. Appl. No. 11/496,982 mailed May 27, 2010.
Office Action in U.S. Appl. No. 11/603,406 mailed Aug. 19, 2010.
Office Action in U.S. Appl. No. 11/634,550 mailed Aug. 4, 2010.
Chiu et al., Non-Invasive Prenatal Assessment of Trisomy 21 by Multiplexed Maternal Plasma DNA Sequencing: Large Scale Validity Study, BMJ, 342(7790), p. 1-9 (Jan. 2011).
Chiu et al., Non-Invasive Prenatal Diagnosis by Single Molecule Counting Technologies, Trends in Genetics, 25(7), p. 324-331 (Jul. 2009).

Dhallan et al., A Non-Invasive Test for Prenatal Diagnosis Based on Fetal DNA Present in Maternal Blood: A Preliminary Study, Lancet, 369(9560), p. 474-481 (Feb. 2007).
Ehrich et al., Noninvasive Detection of Fetal Trisomy 21 by Sequencing of DNA in Maternal Blood: A Study in a Clinical Setting, AJOG, 204(3), p. 205.e1-205.e11 (Mar. 2011).
Fan et al., Noninvasive Diagnosis of Fetal Aneuploidy by Shotgun Sequencing DNA from Maternal Blood, PNAS, 105(42), p. 16266-16271 (Oct. 2008).
Hojsgaard et al., BIFROST—Block Recursive Models Induced from Relevant Knowledge, Observations, and Statistical Techniques, Computational Statistics & Data Analysis, 19(2), p. 155-175 (Feb. 1995).
Liao et al., Targeted Massively Parallel Sequencing of Maternal Plasma DNA Permits Efficient and Unbiased Detection of Fetal Alleles, Clin Chem, 57(1), p. 92-101 (Jan. 2011).
Lo et al., Plasma Placental RNA Allelic Ratio Permits Noninvasive Prenatal Chromosomal Aneuploidy Detection, Nature Medicine, 13(2), p. 218-223 (Feb. 2007).
Lo et al., Maternal Plasma DNA Sequencing Reveals the Genome-Wide Genetic and Mutational Profile of the Fetus, Science Translational Medicine, 2(61), p. 1-13 (Dec. 2010).
Lun et al., Noninvasive Prenatal Diagnosis of Monogenic Diseases by Digital Size Selection and Relative Mutation Dosage on DNA in Maternal Plasma, PNAS, 105(50), p. 19920-19925 (Dec. 2008).
Porreca et al., Multiplex Amplification of Large Sets of Human Exons, Nature Methods, 4(11), p. 931-936 (Oct. 2007).
Tsui et al., Non-Invasive Prenatal Detection of Fetal Trisomy 18 by RNA-SNP Allelic Ratio Analysis Using Maternal Plasma *SERPINB2* mRNA: A Feasibility Study, Prenatal Diagnosis, 29(11), p. 1031-1037 (Nov. 2009).
Turner et al., Massively Parallel Exon Capture and Library-Free Resequencing Across 16 Genomes, Nature Methods, 6(5), p. 315-316 (Apr. 2009).
Office Action in U.S. Appl. No. 11/496,982 mailed Jan. 21, 2011.
Office Action in U.S. Appl. No. 11/634,550 mailed Jan. 24, 2011.
Office Action in U.S. Appl. No. 11/603,406 mailed Feb. 18, 2011.
Office Action in U.S. Appl. No. 11/004,274 mailed Mar. 2, 2011.
Gardina et al., Ploidy Status and Copy Number Aberrations in Primary Glioblastomas Defined by Integrated Analysis of Allelic Ratios, Signal Ratios and Loss of Heterozygosity Using 500K SNP Mapping Arrays, *BMC Genomics*, 9(489), pp. 1-16 (Oct. 2008).
PCT International Search Report based on PCT/US2011/037018 dated Sep. 27, 2011.
Ashoor et al., Chromosome-Selective Sequencing of Maternal Plasma Cell-Free DNA for First-Trimester Detection of Trisomy 21 and Trisomy 18, American Journal of Obstetrics & Gynecology, 206(4), pp. 322.e1-322.e5 (Apr. 2012).
Beer et al., The Biological Basis of Passage of Fetal Cellular Material into the Maternal Circulation, Annals New York Academy of Sciences, 731, pp. 21-35 (Sep. 7, 1994).
Bisignano et al., PGD and Aneuploidy Screening for 24 Chromosomes: Advantages and Disadvantages of Competing Platforms, Reproductive BioMedicine Online, 23(6), pp. 677-685 (Dec. 2011).
Chen et al., Noninvasive Prenatal Diagnosis of Fetal Trisomy 18 and Trisomy 13 by Maternal Plasma DNA Sequencing, PLoS ONE, 6(7), pp. 1-7 (Jul. 2011).
Chiu et al., Noninvasive Prenatal Diagnosis of Fetal Chromosomal Aneuploidy by Massively Parallel Genomic Sequencing of DNA in Maternal Plasma, PNAS, 105(51), pp. 20458-20463 (Dec. 23, 2008).
Chiu et al., Supporting Information, PNAS, 105(51), pp. 1-17 (Dec. 23, 2008).
Chiu et al., Maternal Plasma DNA Analysis with Massively Parallel Sequencing by Litigation for Noninvasive Prenatal Diagnosis of Trisomy 21, Clinical Chemistry, 56(3), pp. 459-463 (Mar. 2010).
Chu et al., Statistical Considerations for Digital Approaches to Non-Invasive Fetal Genotyping, Bioinformatics, 26(22), pp. 2863-2866 (Sep. 23, 2010).
Chu et al., A Novel Approach Toward the Challenge of Accurately Quantifying Fetal DNA in Maternal Plasma, Prenatal diagnosis, 30, pp. 1226-1229 (Nov. 11, 2010).

Cossu et al., Rh D/d Genotyping by Quantitative Polymerase Chain Reaction and Capillary Zone Electrophoresis, Electrophoresis, 17(12), pp. 1911-1915 (Dec. 1996).

DeAngelis et al., Solid-phase Reversible Immobilization for the Isolation of PCR Products, Nucleic Acids Research, 23(22), pp. 4742-4743 (Nov. 25, 1995).

Devaney et al., Noninvasive Fetal Sex Determination Using Cell-Free Fetal DNA: A Systematic Review and Meta-analysis, JAMA, 306(6), pp. 627-636 (Aug. 10, 2011).

Dhallan et al., Methods to Increase the Percentage of Free Fetal DNA Recovered from the Maternal Circulation, JAMA, 291(9), pp. 1114-1119 (Mar. 3, 2004).

Eichler et al., Mild Course of Fetal RhD Haemolytic Disease due to Maternal Alloimmunisation to Paternal HLA Class I and II Antigens, Vox Sang, 68(4), pp. 243-247 (1995).

Ganshirt-Ahlert et al., Three Cases of 45,X/46,XYnf Mosaicism, Hum Genet, 76(2), pp. 153-156 (Jun. 1987).

Gänshirt-Ahlert et al., Ratio of Fetal to Maternal DNA is Less Than 1 in 5000 at different Gestational Ages in Maternal Blood, Clinical Genetics, 38(1), pp. 38-43 (Jul. 1990).

Gänshirt-Ahlert et al., Fetal DNA in Uterine Vein Blood, Obstetrics & Gynecology, 80(4), pp. 601-603 (Oct. 1992).

Ghanta et al., Non-Invasive Prenatal Detection of Trisomy 21 Using Tandem Single Nucleotide Polymorphisms, PLoS ONE, 5(10), pp. 1-10 (Oct. 2010).

Greenwalt et al., The Quantification of Fetomaternal Hemorrhage by an Enzyme-Linked Antibody Test with Glutaraldehyde Fixation, Vox Sang, 63(4), pp. 238-271 (1992).

Homer et al., Resolving Individuals Contributing Trace Amounts of DNA to Highly Complex Mixtures Using High-Density SNP Genotyping Microarrays, PLOS Genetics, 4(8), pp. 1-9 (Aug. 2008).

Kazakov et al., Extracellular DNA in the Blood of Pregnant Women, Tsitologia, 37(3), pp. 1-8 (1995).

Lambert-Messerlian et al., Adjustment of Serum Markers in First Trimester Screening, Journal of Medical Screening, 16(2), pp. 102-103 (2009).

Li et al., Non-Invasive Prenatal Diagnosis Using Cell-Free Fetal DNA in Maternal Plasma from PGD Pregnancies, Reproductive BioMedicine Online, 19(5), pp. 714-720 (Nov. 2009).

Lo et al., Prenatal Sex Determination by DNA Amplification from Maternal Peripheral Blood, The Lancet, 2(8676), pp. 1363-1365 (Dec. 9, 1989).

Lo et al., Detection of Single-Copy Fetal DNA Sequence from Maternal Blood, The Lancet, 335, pp. 1463-1464 (Jun. 16, 1990).

Lo et al., Letters to the Editor: Prenatal Determination of Fetal RhD Status by Analysis of Peripheral Blood of Rhesus Negative Mothers, The Lancet, 341, pp. 1147-1148 (May 1, 1993).

Lo et al., Detection of Fetal RhD Sequence from Peripheral Blood of Sensitized RhD-Negative Pregnant Women, British Journal of Haematology, 87, pp. 658-660 (Apr. 22, 1994).

Lo et al., Prenatal Determination of Fetal Rhesus D Status by DNA Amplification of Peripheral Blood of Rhesus-Negative Mothers, Annals New York Academy of Sciences, 731, pp. 229-236 (Sep. 7, 1994).

Lo et al., Strategies for the Detection of Autosomal Fetal DNA Sequence from Maternal Peripheral Blood, Annals New York Academy of Sciences, 731, pp. 204-213 (Sep. 7, 1994).

Lo et al., Rapid Clearance of Fetal DNA from Maternal Plasma, Am. J. Hum. Genet., 64(1), pp. 218-224 (Jan. 1999).

Lo et al., Letter to the Editor: Free Fetal DNA in Maternal Circulation, JAMA, 292(23), pp. 2835-2836 (Dec. 15, 2004).

Lo et al., Digital PCR for the Molecular Detection of Fetal Chromosomal Aneuploidy, PNAS, 104(32), pp. 13116-13121 (Aug. 7, 2007).

Lo, Fetal Nucleic Acids in Maternal Plasma: Toward the Development of Noninvasive Prenatal Diagnosis of Fetal Chromosomal Aneuploidies, Ann. N.Y. Acad. Sci., 1137, pp. 140-143 (Aug. 2008).

Maniatis et al., Molecular Cloning: A Laboratory Manual, Cold Spring Harbor Laboratory, pp. 458-459 (Jul. 1982).

Mansfield, Diagnosis of Down Syndrome and Other Aneuploidies Using Quantitative Polymerase Chain Reaction and Small Tandem Repeat Polymorphisms, Human Molecular Genetics, 2(1), pp. 43-50 (Jan. 1993).

Orozco et al., Placental Release of Distinct DNA-Associated Micro-Particles into Maternal Circulation: Reflective of Gestation Time and Preeclampsia, Placenta, 30(10), pp. 891-897 (Oct. 2009).

Ozawa et al., Two Families with Fukuyama Congenital Muscular Dystrophy that Underwent In Utero Diagnosis Based on Polymorphism Analysis, Clinical Muscular Dystrophy: Research in Immunology and Genetic Counseling—FY 1994/1995, pp. 13-15 (Mar. 28, 1996).

Palomaki et al., DNA Sequencing of Maternal Plasma to Detect Down Syndrome: An International Clinical Validation Study, Genetics in Medicine, 13(11), pp. 913-920 (Nov. 2011).

Papageorgiou et al., Fetal-Specific DNA Methylation Ratio Permits Noninvasive Prenatal Diagnosis of Trisomy 21, Nature Medicine, 17, pp. 510-513 (Mar. 6, 2011).

Pena et al., Reviews: Paternity Testing in the DNA Era, TIG, 10(6), pp. 204-209 (Jun. 1994).

Peters et al., Noninvasive Prenatal Diagnosis of a Fetal Microdeletion Syndrome, The New England Journal of Medicine, 365(19), pp. 1847-1848 (Nov. 10, 2011).

Phillips et al., Resolving Relationship Tests that Show Ambiguous STR Results Using Autosomal SNPs as Supplementary Markers, Forensic Science International: Genetics 2, 2(3), pp. 198-204 (Jun. 2008).

Roper et al., Forensic Aspects of DNA-Based Human Identity Testing, Journal of Forensic Nursing 4(4), pp. 150-156 (2008).

Sehnert et al., Optimal Detection of Fetal Chromosomal Abnormalities by Massively Parallel DNA Sequencing of Cell-Free Fetal DNA from Maternal Blood, Clinical Chemistry, 57(7), pp. 1-8 (Apr. 25, 2011).

Simpson et al., Fetal Cells in Maternal Blood: Overview and Historical Perspective, Annals New York Academy of Sciences, 731, pp. 1-8 (Sep. 1994).

Sparks et al., Selective Analysis of Cell-Free DNA in Maternal Blood for Evaluation of Fetal Trisomy, Prenatal Diagnosis, 32, pp. 1-7 (Jan. 6, 2012).

Sparks et al., Non-Invasive Prenatal Detection and Selective Analysis of Cell-Free DNA Obtained from Maternal Blood: Evaluation for Trisomy 21 and Trisomy 18, American Journal of Obstetrics & Gynecology, 206(4), pp. 319.e1-319.e9 (Apr. 2012).

Stroun et al., Prehistory of the Notion of Circulating Nucleic Acids in Plasma/Serum (CNAPS): Birth of a Hypothesis, Ann. N.Y. Acad. Sci., 1075, pp. 10-20 (Sep. 2006).

Thomas et al., The Time of Appearance and Disappearance of Fetal DNA from the Maternal Circulation, Prenatal Diagnosis, 15(7), pp. 641-646 (Jul. 1995).

Tong et al., Noninvasive Prenatal Detection of Trisomy 21 by an Epigenetic-Genetic Chromosome-Dosage Approach, Clinical Chemistry, 56(1), pp. 90-98 (Jan. 2010).

PCT International Search Report based on PCT/US2011/061506 dated Mar. 16, 2012.

Harlon et al., "Preimplantation Genetic Testing for Marfan Syndrome", Molecular Human Reproduction, vol. 2, No. 9, pp. 713-715, Sep. 1996.

Myers et al., "Accurate Detection of Aneuploidies in Array CGH and Gene Expression Microarray Data", Bioinformatics, 2004, 20(18), 3533-3543 (2004).

Shaw-Smith et al. "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., Issue 41, pp. 241-248, Apr. 2004.

Wagner et al, "Non-Invasive Prenatal Paternity Testing from Maternal Blood", Int. J. Legal Med. 123: 75-79, Oct. 24, 2008.

Wilton et al., "Birth of a Healthy Infant After Preimplantation Confirmation of Euploidy by Comparative Genomic Hybridization", N. Engl. J. Med., vol. 345, No. 21, pp. 1537-1541, Nov. 22, 2001.

USPTO Office Action in U.S. Appl. No. 11/603,406 mailed Mar. 14, 2013.

PCT International Search Report in PCT/US2011/066938 dated Jun. 20, 2012.

* cited by examiner

SYSTEM AND METHOD FOR CLEANING NOISY GENETIC DATA AND DETERMINING CHROMOSOME COPY NUMBER

CROSS-REFERENCES TO RELATED APPLICATIONS

This application is a continuation-in-part of U.S. application Ser. No. 11/496,982, filed Jul. 31, 2006; a continuation-in-part of U.S. application Ser. No. 11/603,406, filed Nov. 22, 2006; and a continuation-in-part of U.S. application Ser. No. 11/634,550, filed Dec. 6, 2006; which claims the benefit of U.S. 60/846,610, filed Sep. 22, 2006; U.S. 60/817,741, filed Jun. 30, 2006; U.S. 60/789,506, filed Apr. 4, 2006; U.S. 60/774,976, filed Feb. 21, 2006; U.S. 60/754,396, filed Dec. 29, 2005; U.S. 60/742,305, filed Dec. 6, 2005; U.S. 60/739,882, filed Nov. 26, 2005; and U.S. 60/703,415, filed Jul. 29, 2005; the disclosures thereof are incorporated by reference herein in their entirety. This application also claims the benefit of priority to U.S. 60/918,292, filed Mar. 16, 2007; U.S. 60/926,198, filed Apr. 25, 2007; U.S. 60/932,456, filed May 31, 2007; U.S. 60/934,441, filed Jun. 11, 2007; U.S. 61/003,101, filed Nov. 12, 2007; and U.S. 61/008,637, filed Dec. 21, 2007; the disclosures thereof are incorporated by reference herein in their entirety.

GOVERNMENT LICENSE RIGHTS

This invention was made with government support under Grant No. R44HD054958-02A2 awarded by the National Institutes of Health. The government has certain rights in the invention.

BACKGROUND OF THE INVENTION

1. Field of the Invention

The invention relates generally to the field of acquiring, manipulating and using genetic data for medically predictive purposes, and specifically to a system in which imperfectly measured genetic data of a target individual are made more accurate by using known genetic data of genetically related individuals, thereby allowing more effective identification of genetic variations, specifically aneuploidy and disease linked genes, that could result in various phenotypic outcomes.

2. Description of the Related Art

In 2006, across the globe, roughly 800,000 in vitro fertilization (IVF) cycles were run. Of the roughly 150,000 cycles run in the US, about 10,000 involved pre-implantation genetic diagnosis (PGD). Current PGD techniques are unregulated, expensive and highly unreliable: error rates for screening disease-linked loci or aneuploidy are on the order of 10%, each screening test costs roughly $5,000, and a couple is forced to choose between testing aneuploidy, which afflicts roughly 50% of IVF embryos, or screening for disease-linked loci on the single cell. There is a great need for an affordable technology that can reliably determine genetic data from a single cell in order to screen in parallel for aneuploidy, monogenic diseases such as Cystic Fibrosis, and susceptibility to complex disease phenotypes for which the multiple genetic markers are known through whole-genome association studies.

Most PGD today focuses on high-level chromosomal abnormalities such as aneuploidy and balanced translocations with the primary outcomes being successful implantation and a take-home baby. The other main focus of PGD is for genetic disease screening, with the primary outcome being a healthy baby not afflicted with a genetically heritable disease for which one or both parents are carriers. In both cases, the likelihood of the desired outcome is enhanced by excluding genetically suboptimal embryos from transfer and implantation in the mother.

The process of PGD during IVF currently involves extracting a single cell from the roughly eight cells of an early-stage embryo for analysis. Isolation of single cells from human embryos, while highly technical, is now routine in IVF clinics. Both polar bodies and blastomeres have been isolated with success. The most common technique is to remove single blastomeres from day 3 embryos (6 or 8 cell stage). Embryos are transferred to a special cell culture medium (standard culture medium lacking calcium and magnesium), and a hole is introduced into the zona pellucida using an acidic solution, laser, or mechanical techniques. The technician then uses a biopsy pipette to remove a single blastomere with a visible nucleus. Features of the DNA of the single (or occasionally multiple) blastomere are measured using a variety of techniques. Since only a single copy of the DNA is available from one cell, direct measurements of the DNA are highly error-prone, or noisy. There is a great need for a technique that can correct, or make more accurate, these noisy genetic measurements.

Normal humans have two sets of 23 chromosomes in every diploid cell, with one copy coming from each parent. Aneuploidy, the state of a cell with extra or missing chromosome(s), and uniparental disomy, the state of a cell with two of a given chromosome both of which originate from one parent, are believed to be responsible for a large percentage of failed implantations and miscarriages, and some genetic diseases. When only certain cells in an individual are aneuploid, the individual is said to exhibit mosaicism. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as the age of a potential mother increases: between the ages of 35 and 40 it is estimated that between 40% and 50% of the embryos are abnormal, and above the age of 40, more than half of the embryos are like to be abnormal. The main cause of aneuploidy is nondisjunction during meiosis. Maternal nondisjunction constitutes 88% of all nondisjunction of which 65% occurs in meiosis 1 and 23% in meiosis II. Common types of human aneuploidy include trisomy from meiosis I nondisjunction, monosomy, and uniparental disomy. In a particular type of trisomy that arises in meiosis II nondisjunction, or M2 trisomy, an extra chromosome is identical to one of the two normal chromosomes. M2 trisomy is particularly difficult to detect. There is a great need for a better method that can detect for many or all types of aneuploidy at most or all of the chromosomes efficiently and with high accuracy.

Karyotyping, the traditional method used for the prediction of aneuploidy and mosaicism is giving way to other more high-throughput, more cost effective methods such as Flow Cytometry (FC) and fluorescent in situ hybridization (FISH). Currently, the vast majority of prenatal diagnoses use FISH, which can determine large chromosomal aberrations and PCR/electrophoresis, and which can determine a handful of SNPs or other allele calls. One advantage of FISH is that it is less expensive than karyotyping, but the technique is complex and expensive enough that generally a small selection of chromosomes are tested (usually chromosomes 13, 18, 21, X, Y; also sometimes 8, 9, 15, 16, 17, 22); in addition, FISH has a low level of specificity. Roughly seventy-five percent of PGD today measures high-level chromosomal abnormalities such as aneuploidy using FISH with error rates on the order of 10-15%. There is a great demand for an aneuploidy screening method that has a higher throughput, lower cost, and greater accuracy.

The number of known disease associated genetic alleles is currently at 389 according to OMIM and steadily climbing. Consequently, it is becoming increasingly relevant to analyze multiple positions on the embryonic DNA, or loci, that are associated with particular phenotypes. A clear advantage of pre-implantation genetic diagnosis over prenatal diagnosis is that it avoids some of the ethical issues regarding possible choices of action once undesirable phenotypes have been detected. A need exists for a method for more extensive genotyping of embryos at the pre-implantation stage.

There are a number of advanced technologies that enable the diagnosis of genetic aberrations at one or a few loci at the single-cell level. These include interphase chromosome conversion, comparative genomic hybridization, fluorescent PCR, mini-sequencing and whole genome amplification. The reliability of the data generated by all of these techniques relies on the quality of the DNA preparation. Better methods for the preparation of single-cell DNA for amplification and PGD are therefore needed and are under study. All genotyping techniques, when used on single cells, small numbers of cells, or fragments of DNA, suffer from integrity issues, most notably allele drop out (ADO). This is exacerbated in the context of in-vitro fertilization since the efficiency of the hybridization reaction is low, and the technique must operate quickly in order to genotype the embryo within the time period of maximal embryo viability. There exists a great need for a method that alleviates the problem of a high ADO rate when measuring genetic data from one or a small number of cells, especially when time constraints exist.

Listed here is a set of prior art which is related to the field of the current invention. None of this prior art contains or in any way refers to the novel elements of the current invention. In U.S. Pat. No. 6,489,135 Parrott et al. provide methods for determining various biological characteristics of in vitro fertilized embryos, including overall embryo health, implantability, and increased likelihood of developing successfully to term by analyzing media specimens of in vitro fertilization cultures for levels of bioactive lipids in order to determine these characteristics. In US Patent Application 20040033596 Threadgill et al. describe a method for preparing homozygous cellular libraries useful for in vitro phenotyping and gene mapping involving site-specific mitotic recombination in a plurality of isolated parent cells. In U.S. Pat. No. 5,635,366 Cooke et al. provide a method for predicting the outcome of IVF by determining the level of 11β-hydroxysteroid dehydrogenase (11β-HSD) in a biological sample from a female patient. In U.S. Pat. No. 7,058,517 Denton et al. describe a method wherein an individual's haplotypes are compared to a known database of haplotypes in the general population to predict clinical response to a treatment. In U.S. Pat. No. 7,035,739 Schadt at al. describe a method is described wherein a genetic marker map is constructed and the individual genes and traits are analyzed to give a gene-trait locus data, which are then clustered as a way to identify genetically interacting pathways, which are validated using multivariate analysis. In US Patent Application US 2004/0137470 A1, Dhallan et al. describe using primers especially selected so as to improve the amplification rate, and detection of, a large number of pertinent disease related loci, and a method of more efficiently quantitating the absence, presence and/or amount of each of those genes. In World Patent Application WO 03/031646, Findlay et al. describe a method to use an improved selection of genetic markers such that amplification of the limited amount of genetic material will give more uniformly amplified material, and it can be genotyped with higher fidelity.

SUMMARY OF THE INVENTION

The system disclosed enables the cleaning of incomplete or noisy genetic data using secondary genetic data as a source of information, and also the determination of chromosome copy number using said genetic data. While the disclosure focuses on genetic data from human subjects, and more specifically on as-yet not implanted embryos or developing fetuses, as well as related individuals, it should be noted that the methods disclosed apply to the genetic data of a range of organisms, in a range of contexts. The techniques described for cleaning genetic data are most relevant in the context of pre-implantation diagnosis during in-vitro fertilization, prenatal diagnosis in conjunction with amniocentesis, chorion villus biopsy, fetal tissue sampling, and non-invasive prenatal diagnosis, where a small quantity of fetal genetic material is isolated from maternal blood. The use of this method may facilitate diagnoses focusing on inheritable diseases, chromosome copy number predictions, increased likelihoods of defects or abnormalities, as well as making predictions of susceptibility to various disease- and non-disease phenotypes for individuals to enhance clinical and lifestyle decisions. The invention addresses the shortcomings of prior art that are discussed above.

In one aspect of the invention, methods make use of knowledge of the genetic data of the mother and the father such as diploid tissue samples, sperm from the father, haploid samples from the mother or other embryos derived from the mother's and father's gametes, together with the knowledge of the mechanism of meiosis and the imperfect measurement of the embryonic DNA, in order to reconstruct, in silico, the embryonic DNA at the location of key loci with a high degree of confidence. In one aspect of the invention, genetic data derived from other related individuals, such as other embryos, brothers and sisters, grandparents or other relatives can also be used to increase the fidelity of the reconstructed embryonic DNA. It is important to note that the parental and other secondary genetic data allows the reconstruction not only of SNPs that were measured poorly, but also of insertions, deletions, and of SNPs or whole regions of DNA that were not measured at all.

In one aspect of the invention, the fetal or embryonic genomic data which has been reconstructed, with or without the use of genetic data from related individuals, can be used to detect if the cell is aneuploid, that is, where fewer or more than two of a particular chromosome is present in a cell. The reconstructed data can also be used to detect for uniparental disomy, a condition in which two of a given chromosome are present, both of which originate from one parent. This is done by creating a set of hypotheses about the potential states of the DNA, and testing to see which hypothesis has the highest probability of being true given the measured data. Note that the use of high throughput genotyping data for screening for aneuploidy enables a single blastomere from each embryo to be used both to measure multiple disease-linked loci as well as to screen for aneuploidy.

In another aspect of the invention, the direct measurements of the amount of genetic material, amplified or unamplified, present at a plurality of loci, can be used to detect for monosomy, uniparental disomy, trisomy and other aneuploidy states. The idea behind this method is that measuring the amount of genetic material at multiple loci will give a statistically significant result.

In another aspect of the invention, the measurements, direct or indirect, of a particular subset of SNPs, namely those loci where the parents are both homozygous but with different allele values, can be used to detect for chromosomal abnormalities by looking at the ratios of maternally versus paternally miscalled homozygous loci on the embryo. The idea behind this method is that those loci where each parent is homozygous, but have different alleles, by definition result in a heterozygous loci on the embryo. Allele drop outs at those loci are random, and a shift in the ratio of loci miscalled as homozygous can only be due to incorrect chromosome number.

It will be recognized by a person of ordinary skill in the art, given the benefit of this disclosure, that various aspects and embodiments of this disclosure may implemented in combination or separately.

DETAILED DESCRIPTION OF THE PREFERRED EMBODIMENT

Conceptual Overview of the System

The goal of the disclosed system is to provide highly accurate genomic data for the purpose of genetic diagnoses. In cases where the genetic data of an individual contains a significant amount of noise, or errors, the disclosed system makes use of the expected similarities between the genetic data of the target individual and the genetic data of related individuals, to clean the noise in the target genome. This is done by determining which segments of chromosomes of related individuals were involved in gamete formation and, when necessary where crossovers may have occurred during meiosis, and therefore which segments of the genomes of related individuals are expected to be nearly identical to sections of the target genome. In certain situations this method can be used to clean noisy base pair measurements on the target individual, but it also can be used to infer the identity of individual base pairs or whole regions of DNA that were not measured. It can also be used to determine the number of copies of a given chromosome segment in the target individual. In addition, a confidence may be computed for each call made. A highly simplified explanation is presented first, making unrealistic assumptions in order to illustrate the concept of the invention. A detailed statistical approach that can be applied to the technology of today is presented afterward.

In one aspect of the invention, the target individual is an embryo, and the purpose of applying the disclosed method to the genetic data of the embryo is to allow a doctor or other agent to make an informed choice of which embryo(s) should be implanted during IVF. In another aspect of the invention, the target individual is a fetus, and the purpose of applying the disclosed method to genetic data of the fetus is to allow a doctor or other agent to make an informed choice about possible clinical decisions or other actions to be taken with respect to the fetus.

Definitions

SNP (Single Nucleotide Polymorphism): a single nucleotide that may differ between the genomes of two members of the same species. In our usage of the term, we do not set any limit on the frequency with which each variant occurs.

To call a SNP: to make a decision about the true state of a particular base pair, taking into account the direct and indirect evidence.

Locus: a particular region of interest on the DNA of an individual, which may refer to a SNP, the site of a possible insertion or deletion, or the site of some other relevant genetic variation. Disease-linked SNPs may also refer to disease-linked loci.

To call an allele: to determine the state of a particular locus of DNA. This may involve calling a SNP, or determining whether or not an insertion or deletion is present at that locus, or determining the number of insertions that may be present at that locus, or determining whether some other genetic variant is present at that locus.

Correct allele call: An allele call that correctly reflects the true state of the actual genetic material of an individual.

To clean genetic data: to take imperfect genetic data and correct some or all of the errors or fill in missing data at one or more loci. In the context of this disclosure, this involves using genetic data of related individuals and the method described herein.

To increase the fidelity of allele calls: to clean genetic data.

Imperfect genetic data: genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof.

Noisy genetic data: imperfect genetic data, also called incomplete genetic data.

Uncleaned genetic data: genetic data as measured, that is, where no method has been used to correct for the presence of noise or errors in the raw genetic data; also called crude genetic data.

Confidence: the statistical likelihood that the called SNP, allele, set of alleles, or determined number of chromosome segment copies correctly represents the real genetic state of the individual.

Parental Support (PS): a name sometimes used for the any of the methods disclosed herein, where the genetic information of related individuals is used to determine the genetic state of target individuals. In some cases, it refers specifically to the allele calling method, sometimes to the method used for cleaning genetic data, sometimes to the method to determine the number of copies of a segment of a chromosome, and sometimes to some or all of these methods used in combination.

Copy Number Calling (CNC): the name given to the method described in this disclosure used to determine the number of chromosome segments in a cell.

Qualitative CNC (also qCNC): the name given to the method in this disclosure used to determine chromosome copy number in a cell that makes use of qualitative measured genetic data of the target individual and of related individuals.

Multigenic: affected by multiple genes, or alleles.

Direct relation: mother, father, son, or daughter.

Chromosomal Region: a segment of a chromosome, or a full chromosome.

Segment of a Chromosome: a section of a chromosome that can range in size from one base pair to the entire chromosome.

Section: a section of a chromosome. Section and segment can be used interchangeably.

Chromosome: may refer to either a full chromosome, or also a segment or section of a chromosome.

Copies: the number of copies of a chromosome segment may refer to identical copies, or it may refer to non-identical copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotypic Data: also called 'phased data' or 'ordered genetic data;' data from a single chromosome in a diploid or polyploid genome, i.e., either the segregated maternal or paternal copy of a chromosome in a diploid genome.

Unordered Genetic Data: pooled data derived from measurements on two or more chromosomes in a diploid or polyploid genome, i.e., both the maternal and paternal copies of a chromosome in a diploid genome.

Genetic data 'in', 'of', 'at' or 'on' an individual: These phrases all refer to the data describing aspects of the genome of an individual. It may refer to one or a set of loci, partial or entire sequences, partial or entire chromosomes, or the entire genome.

Hypothesis: a set of possible copy numbers of a given set of chromosomes, or a set of possible genotypes at a given set of loci. The set of possibilities may contain one or more elements.

Target Individual: the individual whose genetic data is being determined. Typically, only a limited amount of DNA is available from the target individual. In one context, the target individual is an embryo or a fetus.

Related Individual: any individual who is genetically related, and thus shares haplotype blocks, with the target individual.

Platform response: a mathematical characterization of the input/output characteristics of a genetic measurement platform, such as TAQMAN or INFINIUM. The input to the channel is the true underlying genotypes of the genetic loci being measured. The channel output could be allele calls (qualitative) or raw numerical measurements (quantitative), depending on the context. For example, in the case in which the platform's raw numeric output is reduced to qualitative genotype calls, the platform response consists of an error transition matrix that describes the conditional probability of seeing a particular output genotype call given a particular true genotype input. In the case in which the platform's output is left as raw numeric measurements, the platform response is a conditional probability density function that describes the probability of the numeric outputs given a particular true genotype input.

Copy number hypothesis: a hypothesis about how many copies of a particular chromosome segment are in the embryo. In a preferred embodiment, this hypothesis consists of a set of sub-hypotheses about how many copies of this chromosome segment were contributed by each related individual to the target individual.

Technical Description of the System
A Allele Calling: Preferred Method

Assume here the goal is to estimate the genetic data of an embryo as accurately as possible, and where the estimate is derived from measurements taken from the embryo, father, and mother across the same set of n SNPs. Note that where this description refers to SNPs, it may also refer to a locus where any genetic variation, such as a point mutation, insertion or deletion may be present. This allele calling method is part of the Parental Support (PS) system. One way to increase the fidelity of allele calls in the genetic data of a target individual for the purposes of making clinically actionable predictions is described here. It should be obvious to one skilled in the art how to modify the method for use in contexts where the target individual is not an embryo, where genetic data from only one parent is available, where neither, one or both of the parental haplotypes are known, or where genetic data from other related individuals is known and can be incorporated.

For the purposes of this discussion, only consider SNPs that admit two allele values; without loss of generality it is possible to assume that the allele values on all SNPs belong to the alphabet $A=\{A,C\}$. It is also assumed that the errors on the measurements of each of the SNPs are independent. This assumption is reasonable when the SNPs being measured are from sufficiently distant genic regions. Note that one could incorporate information about haplotype blocks or other techniques to model correlation between measurement errors on SNPs without changing the fundamental concepts of this invention.

Let $e=(e_1,e_2)$ be the true, unknown, ordered SNP information on the embryo, $e_1,e_2 \in A^n$. Define $e_1$ to be the genetic haploid information inherited from the father and $e_2$ to be the genetic haploid information inherited from the mother. Also use $e_i=(e_{1i},e_{2i})$ to denote the ordered pair of alleles at the i-th position of e. In similar fashion, let $f=(f_1,f_2)$ and $m=(m_1,m_2)$ be the true, unknown, ordered SNP information on the father and mother respectively. In addition, let $g_1$ be the true, unknown, haploid information on a single sperm from the father. (One can think of the letter g as standing for gamete. There is no $g_2$. The subscript is used to remind the reader that the information is haploid, in the same way that $f_1$ and $f_2$ are haploid.) It is also convenient to define $r=(f,m)$, so that there is a symbol to represent the complete set of diploid parent information from which e inherits, and also write $r_i=(f_i,m_i)=((f_{1i},f_{2i}),(m_{1i},m_{2i}))$ to denote the complete set of ordered information on father and mother at the i-th SNP. Finally, let $\hat{e}=(\hat{e}_1,\hat{e}_2)$ be the estimate of e that is sought, $\hat{e}_1,\hat{e}_2 \in A^n$.

By a crossover map, it is meant an n-tuple $\theta \in \{1,2\}^n$ that specifies how a haploid pair such as $(f_1,f_2)$ recombines to form a gamete such as $e_1$. Treating $\theta$ as a function whose output is a haploid sequence, define $\theta(f)_i=\theta(f_1,f_2)_i=f_{\theta_i,i}$. To make this idea more concrete, let $f_1$=ACAAACCC, let $f_2$=CAACCACA, and let $\theta$=11111222. Then $\theta(f_1,f_2)$=ACAAAACA. In this example, the crossover map $\theta$ implicitly indicates that a crossover occurred between SNPs i=5 and i=6.

Formally, let $\theta$ be the true, unknown crossover map that determines $e_1$ from f, let $\phi$ be the true, unknown crossover map that determines $e_2$ from m, and let $\psi$ be the true, unknown crossover map that determines $g_1$ from f. That is, $e_1=\theta(f)$, $e_2=\phi(m)$, $g_1=\psi(f)$. It is also convenient to define $X=(\theta,\phi,\psi)$ so that there is a symbol to represent the complete set of crossover information associated with the problem. For simplicity sake, write $e=X(r)$ as shorthand for $e=(\theta(f),\phi(m))$; also write $e_i=X(r_i)$ as shorthand for $e_i=X(r)_i$.

In reality, when chromosomes combine, at most a few crossovers occur, making most of the $2^n$ theoretically possible crossover maps distinctly improbable. In practice, these very low probability crossover maps will be treated as though they had probability zero, considering only crossover maps belonging to a comparatively small set $\Omega$. For example, if $\Omega$ is defined to be the set of crossover maps that derive from at most one crossover, then $|\Omega|=2n$.

It is convenient to have an alphabet that can be used to describe unordered diploid measurements. To that end, let $B=\{A,B,C,X\}$. Here A and C represent their respective homozygous locus states and B represents a heterozygous but unordered locus state. Note: this section is the only section of the document that uses the symbol B to stand for a heterozygous but unordered locus state. Most other sections of the document use the symbols A and B to stand for the two different allele values that can occur at a locus. X represents an unmeasured locus, i.e., a locus drop-out. To make this idea more concrete, let $f_1$=ACAAACCC, and let $f_2$=CAACCACA. Then a noiseless unordered diploid measurement of f would yield $\tilde{f}$=BBABBBCB.

In the problem at hand, it is only possible to take unordered diploid measurements of e, f, and m, although there may be ordered haploid measurements on $g_1$. This results in noisy measured sequences that are denoted $\tilde{e} \in B^n$, $\tilde{f} \in B^n$, $\tilde{m} \in B^n$, and $\tilde{g}_1 \in A^n$ respectively. It will be convenient to define $\tilde{r}=(\tilde{f},\tilde{m})$ so that there is a symbol that represents the noisy measurements on the parent data. It will also be convenient to define $\tilde{D}=(\tilde{r}, \tilde{e}, \tilde{g}_1)$ so that there is a symbol to represent the complete set of noisy measurements associated with the problem, and to write $\tilde{D}_i=(\tilde{r}_i,\tilde{e}_i,\tilde{g}_{1i})=(\tilde{f}_i,\tilde{m}_i,\tilde{e}_i,\tilde{g}_{1i})$ to denote the complete set of measurements on the i-th SNP. (Please note that, while $f_i$ is an ordered pair such as (A,C), $\tilde{f}_i$ is a single letter such as B.)

Because the diploid measurements are unordered, nothing in the data can distinguish the state $(f_1,f_2)$ from $(f_2,f_1)$ or the state $(m_1,m_2)$ from $(m_2,m_1)$. These indistinguishable symmetric states give rise to multiple optimal solutions of the estimation problem. To eliminate the symmetries, and without loss of generality, assign $\theta_1=\phi_1=1$.

In summary, then, the problem is defined by a true but unknown underlying set of information $\{r,e,g_1,X\}$, with $e=X$ (r). Only noisy measurements $\tilde{D}=(\tilde{r},\tilde{e},\tilde{g}_1)$ are available. The goal is to come up with an estimate $\hat{e}$ of e, based on $\tilde{D}$.

Note that this method implicitly assumes euploidy on the embryo. It should be obvious to one skilled in the art how this method could be used in conjunction with the aneuploidy calling methods described elsewhere in this patent. For example, the aneuploidy calling method could be first employed to ensure that the embryo is indeed euploid and only then would the allele calling method be employed, or the aneuploidy calling method could be used to determine how many chromosome copies were derived from each parent and only then would the allele calling method be employed. It should also be obvious to one skilled in the art how this method could be modified in the case of a sex chromosome where there is only one copy of a chromosome present.

Solution Via Maximum a Posteriori Estimation

In one embodiment of the invention, it is possible, for each of the n SNP positions, to use a maximum a posteriori (MAP) estimation to determine the most probable ordered allele pair at that position. The derivation that follows uses a common shorthand notation for probability expressions. For example, $P(e'_i,\tilde{D}|X')$ is written to denote the probability that random variable $e_i$ takes on value $e'_i$ and the random variable $\tilde{D}$ takes on its observed value, conditional on the event that the random variable X takes on the value X'. Using MAP estimation, then, the i-th component of $\hat{e}$, denoted $\hat{e}_i=(\hat{e}_{1i},\hat{e}_{2i})$ is given by $$\hat{e}_i = \underset{e'_i}{\operatorname{argmax}} P(e'_i \mid \tilde{D})$$

$$= \underset{e'_i}{\operatorname{argmax}} P(e'_i, \tilde{D})$$

$$= \underset{e'_i}{\operatorname{argmax}} \sum_{X' \in \Omega^3} P(X')P(e'_i, \tilde{D} \mid X')$$

$$(a) = \underset{e'_i}{\operatorname{argmax}} \sum_{X' \in \Omega^3 : \theta'_1 = \phi'_1 = 1} P(X')P(e'_i, \tilde{D}_i \mid X') \prod_{j \neq i} P(\tilde{D}_j \mid X')$$

$$(b) = \underset{e'_i}{\operatorname{argmax}} \sum_{X' \in \Omega^3 P : \theta'_1 = \phi'_1 = 1} P(X')$$

$$\sum_{r'_i \in A^4} P(r'_i)P(e'_i, \tilde{D}_i \mid X', r'_i) \prod_{j \neq i} \sum_{r'_j \in A^4} P(r'_j)P(\tilde{D}_j \mid X', r'_j)$$

$$(c) = \underset{e'_i}{\operatorname{argmax}} \sum_{X' \in \Omega^3 : \theta'_1 = \phi'_1 = 1} P(X') \sum_{r'_i \in A^4} P(r'_i)P(e'_i \mid X', r'_i)$$

$$P(\tilde{D}_i \mid X', r'_i) \prod_{j \neq i} \sum_{r'_j \in A^4} P(r'_j)P(\tilde{D}_j \mid X', r'_j)$$

$$(*) = \underset{e'_i}{\operatorname{argmax}} \sum_{X' \in \Omega^3 : \theta'_1 = \phi'_1 = 1} P(X')$$

$$\prod_j \sum_{r'_j \in A^4} \mathbb{1}(i \neq j \text{ or } X'(r'_j) = e'_i)P(r'_j)P(\tilde{D}_j \mid X', r'_j)$$

In the preceding set of equations, (a) holds because the assumption of SNP independence means that all of the random variables associated with SNP i are conditionally independent of all of the random variables associated with SNP j, given X; (b) holds because r is independent of X; (c) holds because $e_i$ and $\tilde{D}_i$ are conditionally independent given $r_i$ and X (in particular, $e_i=X(r_i)$); and (*) holds, again, because $e_i=X(r_i)$, which means that $P(e'_i|X',r'_i)$ evaluates to either one or zero and hence effectively filters $r'_i$ to just those values that are consistent with $e'_i$ and X'.

The final expression (*) above contains three probability expressions: $P(X')$, $P(r'_j)$, and $P(\tilde{D}_j|X',r'_j)$. The computation of each of these quantities is discussed in the following three sections.

Crossover Map Probabilities

Recent research has enabled the modeling of the probability of recombination between any two SNP loci. Observations from sperm studies and patterns of genetic variation show that recombination rates vary extensively on kilobase scales and that much recombination occurs in recombination hotspots. The NCBI data about recombination rates on the Human Genome is publicly available through the UCSC Genome Annotation Database.

One may use the data set from the Hapmap Project or the Perlegen Human Haplotype Project. The latter is higher density; the former is higher quality. These rates can be estimated using various techniques known to those skilled in the art, such as the reversible-jump Markov Chain Monte Carlo (MCMC) method that is available in the package LDHat.

In one embodiment of the invention, it is possible to calculate the probability of any crossover map given the probability of crossover between any two SNPs. For example, $P(\theta=11111222)$ is one half the probability that a crossover occurred between SNPs five and six. The reason it is only half the probability is that a particular crossover pattern has two crossover maps associated with it: one for each gamete. In this case, the other crossover map is $\theta=22222111$.

Recall that $X=(\theta,\phi,\psi)$, where $e_1=\theta(f)$, $e_2=\phi(m)$, $g_1=\psi(f)$. Obviously $\theta$, $\phi$, and $\psi$ result from independent physical events, so $P(X)=P(\theta)P(\phi)P(\psi)$. Further assume that $P_\theta(\bullet)=P_\phi(\bullet)=P_\psi(\bullet)$, where the actual distribution $P_\theta(\bullet)$ is determined in the obvious way from the Hapmap data.

Allele Probabilities

It is possible to determine $P(r_i)=P(f_i)P(m_i)=P(f_{i1})P(f_{i2})P(m_{i1})P(m_{i2})$ using population frequency information from databases such as dbSNP. Also, as mentioned previously, choose SNPs for which the assumption of intra-haploid independence is a reasonable one. That is, assume that $$P(r) = \prod_i P(r_i)$$

Measurement Errors

Conditional on whether a locus is heterozygous or homozygous, measurement errors may be modeled as independent and identically distributed across all similarly typed loci. Thus:

$$P(\tilde{D} \mid X, r) = \prod_i P(\tilde{D}_i \mid X, r_i)$$

$$= \prod_i P(\tilde{f}_i, \tilde{m}_i, \tilde{e}_i, \tilde{g}_{1i} \mid X, f_i, m_i)$$

$$= \prod_i P(\tilde{f}_i \mid f_i) P(\tilde{m}_i \mid m_i) P(\tilde{e}_i \mid \theta(f_i), \phi(m_i)) P(\tilde{g}_{1i} \mid \Psi(f_i))$$

where each of the four conditional probability distributions in the final expression is determined empirically, and where the additional assumption is made that the first two distributions are identical. For example, for unordered diploid measurements on a blastomere, empirical values $p_d=0.5$ and $p_a=0.02$ are obtained, which lead to the conditional probability distribution for $P(\tilde{e}_i | e_i)$ shown in Table 1.

Note that the conditional probability distributions mentioned above, $P(\tilde{f}_i | f_i)$, $P(\tilde{m}_i | m_i)$, $P(\tilde{e}_i | e_i)$, can vary widely from experiment to experiment, depending on various factors in the lab such as variations in the quality of genetic samples, or variations in the efficiency of whole genome amplification, or small variations in protocols used. Therefore, in a preferred embodiment, these conditional probability distributions are estimated on a per-experiment basis. We focus in later sections of this disclosure on estimating $P(\tilde{e}_i | e_i)$, but it will be clear to one skilled in the art after reading this disclosure how similar techniques can be applied to estimating $P(\tilde{f}_i | f_i)$ and $P(\tilde{m}_i | m_i)$. The distributions can each be modeled as belonging to a parametric family of distributions whose particular parameter values vary from experiment to experiment. As one example among many, it is possible to implicitly model the conditional probability distribution $P(\tilde{e}_i | e_i)$ as being parameterized by an allele dropout parameter $p_d$ and an allele dropin parameter $p_a$. The values of these parameters might vary widely from experiment to experiment, and it is possible to use standard techniques such as maximum likelihood estimation, MAP estimation, or Bayesian inference, whose application is illustrated at various places in this document, to estimate the values that these parameters take on in any individual experiment. Regardless of the precise method one uses, the key is to find the set of parameter values that maximizes the joint probability of the parameters and the data, by considering all possible tuples of parameter values within a region of interest in the parameter space. As described elsewhere in the document, this approach can be implemented when one knows the chromosome copy number of the target genome, or when one doesn't know the copy number call but is exploring different hypotheses. In the latter case, one searches for the combination of parameters and hypotheses that best match the data are found, as is described elsewhere in this disclosure.

Note that one can also determine the conditional probability distributions as a function of particular parameters derived from the measurements, such as the magnitude of quantitative genotyping measurements, in order to increase accuracy of the method. This would not change the fundamental concept of the invention.

It is also possible to use non-parameteric methods to estimate the above conditional probability distributions on a per-experiment basis. Nearest neighbor methods, smoothing kernels, and similar non-parameteric methods familiar to those skilled in the art are some possibilities. Although this disclosure focuses parametric estimation methods, use of non-parameteric methods to estimate these conditional probability distributions would not change the fundamental concept of the invention. The usual caveats apply: parametric methods may suffer from model bias, but have lower variance. Non-parametric methods tend to be unbiased, but will have higher variance.

Note that it should be obvious to one skilled in the art, after reading this disclosure, how one could use quantitative information instead of explicit allele calls, in order to apply the PS method to making reliable allele calls, and this would not change the essential concepts of the disclosure.

B Factoring the Allele Calling Equation

In a preferred embodiment of the invention, the algorithm for allele calling can be structured so that it can be executed in a more computationally efficient fashion. In this section the equations are re-derived for allele-calling via the MAP method, this time reformulating the equations so that they reflect such a computationally efficient method of calculating the result.

Notation $X^*, Y^*, Z^* \in \{A,C\}^{n \times 2}$ are the true ordered values on the mother, father, and embryo respectively.

$H^* \in \{A,C\}^{n \times h}$ are true values on h sperm samples.

$B^* \in \{A,C\}^{n \times b \times 2}$ are true ordered values on b blastomeres.

$D = \{x,y,z,B,H\}$ is the set of unordered measurement data on father, mother, embryo, b blastomeres and h sperm samples. $D_i = \{x_i, y_i, z_i, H_i, B_i\}$ is the data set restricted to the i-th SNP.

$r \in \{A,C\}^4$ represents a candidate 4-tuple of ordered values on both the mother and father at a particular locus.

$\hat{Z}_i \in \{A,C\}^2$ is the estimated ordered embryo value at SNP i.

$Q = (2+2b+h)$ is the effective number of haploid chromosomes being measured, excluding the parents. Any hypothesis about the parental origin of all measured data (excluding the parents themselves) requires that Q crossover maps be specified.

$\chi \in \{1,2\}^{n \times Q}$ is a crossover map matrix, representing a hypothesis about the parental origin of all measured data, excluding the parents. Note that there are $2^{nQ}$ different crossover matrices. $\chi_i \triangleq \chi_{i,}$ is the matrix restricted to the i-th row. Note that there are $2^Q$ vector values that the i-th row can take on, from the set $\chi \in \{1,2\}^Q$.

$f(x; y, z)$ is a function of $(x, y, z)$ that is being treated as a function of just x. The values behind the semi-colon are constants in the context in which the function is being evaluated.

PS Equation Factorization $$\hat{Z}_i = \underset{z_i}{\mathrm{argmax}} P(Z_i, D)$$

$$= \underset{z_i}{\mathrm{argmax}} \sum_{\chi} P(\chi) P(Z_i, D|\chi)$$

$$= \underset{z_i}{\mathrm{argmax}} \sum_{\chi} P(\chi_1) P(\chi_2|\chi_1) \ldots P(\chi_n, \chi_{n-1})$$

$$\left( \sum_{r \in (A,C)^4} P(r) P(Z_i, D_i | X_i, r) \right) \prod_{j \neq 1} \left( \sum_{r \in (A,C)^4} P(r) P(D_j | X_j, r) \right)$$

$$= \underset{z_i}{\mathrm{argmax}} \sum_{\chi} P(\chi_1) P(\chi_2|\chi_1) \ldots P(\chi_n, \chi_{n-1}) f_1(\chi_i; Z_i, D_i)$$

$$\prod_{j=1} f_2(\chi_j; D_j)$$

$$= \underset{z_i}{\mathrm{argmax}} \sum_{\chi_1 \in \{1,2\}^Q} \ldots \sum_{\chi_2 \in \{1,2\}^Q} P(\chi_1) P(\chi_2|\chi_1) \ldots P(\chi_n, \chi_{n-1})$$

$$f_1(\chi_i; Z_i, D_i) \prod_{j=1} f_2(\chi_j; D_j)$$

$$= \underset{z_i}{\mathrm{argmax}} \sum_{\chi_1 \in \{1,2\}^Q} P(\chi_1) f_2(\chi_1; D_1) \times \sum_{\chi_2 \in \{1,2\}^Q} P(\chi_2|\chi_1)$$

$$f_2(\chi_2; D_2) \times \ldots \sum_{\chi_1 \in \{1,2\}^Q} P(\chi_i | X_{i-1}) f_1(\chi_i; Z_i, D_i) \times$$

$$\sum_{\chi_n \in \{1,2\}^Q} P(\chi_n | X_{n-1}) f_2(\chi_n; D_n)$$

The number of different crossover matrices $\chi$ is $2^{nQ}$. Thus, a brute-force application of the first line above is $U(n2^{nQ})$. By exploiting structure via the factorization of $P(\chi)$ and $P(z_i, D|\chi)$, and invoking the previous result, final line gives an expression that can be computed in $O(n2^{2Q})$.

C Quantitative Detection of Aneuploidy

In one embodiment of the invention, aneuploidy can be detected using the quantitative data output from the PS method discussed in this patent. Disclosed herein are multiple methods that make use of the same concept; these methods are termed Copy Number Calling (CNC). The statement of the problem is to determine the copy number of each of 23 chromosome-types in a single cell. The cell is first pre-amplified using a technique such as whole genome amplification using the MDA method. Then the resulting genetic material is selectively amplified with a technique such as PCR at a set of n chosen SNPs at each of m=23 chromosome types.

This yields a data set $[t_{ij}]$, $i=1 \ldots n$, $j=1 \ldots m$ of regularized ct (ct, or CT, is the point during the cycle time of the amplification at which dye measurement exceeds a given threshold) values obtained at SNP i, chromosome j. A regularized ct value implies that, for a given (i,j), the pair of raw ct values on channels FAM and VIC (these are arbitrary channel names denoting different dyes) obtained at that locus are combined to yield a ct value that accurately reflects the ct value that would have been obtained had the locus been homozygous. Thus, rather than having two ct values per locus, there is just one regularized ct value per locus.

The goal is to determine the set $\{n_j\}$ of copy numbers on each chromosome. If the cell is euploid, then $n_j=2$ for all j; one exception is the case of the male X chromosome. If $n_j \neq 2$ for at least one j, then the cell is aneuploid; excepting the case of male X.

Biochemical Model

The relationship between ct values and chromosomal copy number is modeled as follows: $\alpha_{ij} n_j Q 2^{\beta_{ij} t_{ij}} - Q_T$. In this expression, $n_j$ is the copy number of chromosome j. Q is an abstract quantity representing a baseline amount of pre-amplified genetic material from which the actual amount of pre-amplified genetic material at SNP i, chromosome j can be calculated as $\alpha_{ij} n_j Q$. $\alpha_{ij}$ is a preferential amplification factor that specifies how much more SNP i on chromosome j will be pre-amplified via MDA than SNP 1 on chromosome 1. By definition, the preferential amplification factors are relative to $$\alpha_{11} \triangleq 1.$$

$\beta_{ij}$ is the doubling rate for SNP i chromosome j under PCR. $t_{ij}$ is the ct value. $Q_T$ is the amount of genetic material at which the ct value is determined. T is a symbol, not an index, and merely stands for threshold.

It is important to realize that $\alpha_{ij}$, $\beta_{ij}$, and $Q_T$ are constants of the model that do not change from experiment to experiment. By contrast, $n_j$ and Q are variables that change from experiment to experiment. Q is the amount of material there would be at SNP 1 of chromosome 1, if chromosome 1 were monosomic.

The original equation above does not contain a noise term. This can be included by rewriting it as follows:

$$(*) \beta_{ij} t_{ij} = \log \frac{Q_T}{\alpha_{ij}} - \log n_j, \log Q + Z_{ij}$$

The above equation indicates that the ct value is corrupted by additive Gaussian noise $Z_{ij}$. Let the variance of this noise term be $\sigma_{ij}^2$.

Maximum Likelihood (ML) Estimation of Copy Number

In one embodiment of the method, the maximum likelihood estimation is used, with respect to the model described above, to determine $n_j$. The parameter Q makes this difficult unless another constraint is added:

$$\frac{1}{m} \sum_j \log n_j = 1$$

This indicates that the average copy number is 2, or, equivalently, that the average log copy number is 1. With this additional constraint one can now solve the following ML problem:

$$\hat{Q}, \hat{n}_j = \underset{Q, n_j}{\mathrm{argmax}} \prod_{ij} f_z \left( \left( \log \frac{Q_T}{\alpha_{ij}} - \beta_{ij} t_{ij} \right)^{\log n_j + \log Q -} \right) \text{s.t.} \frac{1}{m} \sum_j \log n_j = 1$$

$$= \underset{Q, n_j}{\mathrm{argmin}} \sum_{ij} \frac{1}{\sigma_{ij}^2} \left( \left( \log \frac{Q_T}{\alpha_{ij}} - \beta_{ij} t_{ij} \right)^{\log n_j + \log Q -} \right)^2 \text{s.t.} \frac{1}{m} \sum_j \log n_j = 1$$

The last line above is linear in the variables $\log n_j$ and $\log Q$, and is a simple weighted least squares problem with an equality constraint. The solution can be obtained in closed form by forming the Lagrangian $$L(\log n_j, \log Q) = \sum_{ij} \frac{1}{\sigma_{ij}^2}\left(\left(\log\frac{Q_T}{\alpha_{ij}} - \beta_{ij}t_{ij}\right) - \frac{\log n_j + \log Q - }{}\right)^2 + \lambda\sum_j \log n_j$$

and taking partial derivatives.

Solution when Noise Variance is Constant

To avoid unnecessarily complicating the exposition, set $\sigma_{ij}^2=1$. This assumption will remain unless explicitly stated otherwise. (In the general case in which each $\sigma_{ij}^2$ is different, the solutions will be weighted averages instead of simple averages, or weighted least squares solutions instead of simple least squares solutions.) In that case, the above linear system has the solution:

$$\log Q_j \triangleq \frac{1}{n}\sum_i \left(\log\frac{Q_T}{\alpha_{ij}} - \beta_{ij}t_{ij}\right)$$

$$\log Q = \frac{1}{m}\sum_j \log Q_j - 1$$

$$\log n_j = \log Q_j - \log Q = \log\frac{Q_j}{Q}$$

The first equation can be interpreted as a log estimate of the quantity of chromosome j. The second equation can be interpreted as saying that the average of the $Q_j$ is the average of a diploid quantity; subtracting one from its log gives the desired monosome quantity. The third equation can be interpreted as saying that the copy number is just the ratio $$\frac{Q_j}{Q}.$$

Note that $n_j$ is a 'double difference', since it is a difference of Q-values, each of which is itself a difference of values.

Simple Solution

The above equations also reveal the solution under simpler modeling assumptions: for example, when making the assumption $\alpha_{ij}=1$ for all i and j and/or when making the assumption that $\beta_{ij}=\beta$ for all i and j. In the simplest case, when both $\alpha_{ij}=1$ and $\beta_{ij}=\beta$, the solution reduces to $$(**)\log n_j = 1 + \beta\left(\frac{1}{mn}\sum_{ij} t_{ij} - \frac{1}{n}\sum_i t_{ij}\right)$$

The Double Differencing Method

In one embodiment of the invention, it is possible to detect monosomy using double differencing. It should be obvious to one skilled in the art how to modify this method for detecting other aneuploidy states. Let $\{t_{ij}\}$ be the regularized ct values obtained from MDA pre-amplification followed by PCR on the genetic sample. As always, $t_{ij}$ is the ct value on the i-th SNP of the j-th chromosome. Denote by $t_j$ the vector of ct values associated with the j-th chromosome. Make the following definitions:

$$\bar{t} \triangleq \frac{1}{mn}\sum_{ij} t_{ij}$$

-continued $$\tilde{t}_j \triangleq t_j - \bar{t}\mathbf{1}$$

Classify chromosome j as monosomic if and only if $f^T\tilde{t}_j$ is higher than a certain threshold value, where f is a vector that represents a monosomy signature. f is the matched filter, whose construction is described next.

The matched filter f is constructed as a double difference of values obtained from two controlled experiments. Begin with known quantities of euploid male genetic data and euploid female genetic material. Assume there are large quantities of this material, and pre-amplification can be omitted. On both the male and female material, use PCR to sequence n SNPs on both the X chromosome (chromosome 23), and chromosome 7. Let $\{t_{ij}^X\}$, i=1 ... n, j∈{7, 23} denote the measurements on the female, and let $\{t_{ij}^Y\}$ similarly denote the measurements on the male. Given this, it is possible to construct the matched filter f from the resulting data as follows:

$$\bar{t}_7^X \triangleq \frac{1}{n}\sum_i t_{i,7}^X$$

$$\bar{t}_7^Y \triangleq \frac{1}{n}\sum_i t_{i,7}^Y$$

$$\Delta^X \triangleq t_{23}^X - \bar{t}_7^X \mathbf{1}$$

$$\Delta^Y \triangleq t_{23}^Y - \bar{t}_7^Y \mathbf{1}$$

$$f \triangleq \Delta^Y - \Delta^X$$

In the above, equations, $\bar{t}_7^X$ and $\bar{t}_7^Y$ are scalars, while $\Delta^X$ and $\Delta^Y$ are vectors. Note that the superscripts X and Y are just symbolic labels, not indices, denoting female and male respectively. Do not to confuse the superscript X with measurements on the X chromosome. The X chromosome measurements are the ones with subscript 23.

The next step is to take noise into account and to see what remnants of noise survive in the construction of the matched filter f as well as in the construction of $\tilde{t}_j$. In this section, consider the simplest possible modeling assumption: that $\beta_{ij}=\beta$ for all i and j, and that $\alpha_{ij}=1$ for all i and j. Under these assumptions, from (*) above:

$$\beta t_{ij} = \log Q_T - \log n_j - \log Q + Z_{ij}$$

Which can be rewritten as:

$$t_{ij} = \frac{1}{\beta}\log Q_T - \frac{1}{\beta}\log n_j - \frac{1}{\beta}\log Q + Z_{ij}$$

In that case, the i-th component of the matched filter f is given by:

$$f_i \triangleq \Delta_i^Y - \Delta_i^X =$$

$$\{t_{i,23}^Y - \bar{t}_7^Y\} - \{(t_{i,23}^X - \bar{t}_7^X)\} = \left\{\left(\frac{1}{\beta}\log Q_T - \frac{1}{\beta}\log n_{23}^Y - \frac{1}{\beta}\log Q^Y + Z_{i,23}^Y\right) - \right.$$

$$\frac{1}{n}\sum_i\left(\frac{1}{\beta}\log Q_T - \frac{1}{\beta}\log n_7^Y - \frac{1}{\beta}\log Q^Y + Z_{i,7}^Y\right)\right\} -$$

$$\left\{\left(\frac{1}{\beta}\log Q_T - \frac{1}{\beta}\log n_{23}^X - \frac{1}{\beta}\log Q^X + Z_{i,23}^X\right) -\right.$$

$$\frac{1}{n}\sum_i\left(\frac{1}{\beta}\log Q_T - \frac{1}{\beta}\log n_7^X - \frac{1}{\beta}\log Q^X + Z_{i,7}^X\right)\right\} -$$

$$\left\{\left(\frac{1}{\beta}+Z_{i,23}^Y\right)-\frac{1}{n}\sum_i Z_{i,7}^Y\right\}-\left\{Z_{i,23}^X-\frac{1}{n}\sum_i Z_{i,7}^X\right\}$$

Note that the above equations take advantage of the fact that all the copy number variables are known, for example, $n_{23}{}^Y=1$ and that $n_{23}{}^X=2$.

Given that all the noise terms are zero mean, the ideal matched filter is $1/\beta 1$. Further, since scaling the filter vector doesn't really change things, the vector 1 can be used as the matched filter. This is equivalent to simply taking the average of the components of $\tilde{t}_j$. In other words, the matched filter paradigm is not necessary if the underlying biochemistry follows the simple model. In addition, one may omit the noise terms above, which can only serve to lower the accuracy of the method. Accordingly, this gives:

$$\tilde{t}_{ij} \triangleq t_j - \bar{t} = \left\{\frac{1}{\beta}\log Q_T - \frac{1}{\beta}\log n_i - \frac{1}{\beta}\log Q + Z_{ij}\right\} -$$

$$\frac{1}{mn}\sum_{i,j}\left\{\frac{1}{\beta}\log Q_T - \frac{1}{\beta}\log n_i - \frac{1}{\beta}\log Q + Z_{ij}\right\} =$$

$$\frac{1}{\beta}(1-\log n_j) + Z_{ij} - \frac{1}{mn}\sum_{i,j} Z_{ij}$$

In the above, it is assumed that $$\frac{1}{mn}\sum_{i,j}\log n_j = 1.$$

that is, that the average copy number is 2.

Each element of the vector is an independent measurement of the log copy number (scaled by $1/\beta$), and then corrupted by noise. The noise term $Z_{ij}$ cannot be gotten rid of: it is inherent in the measurement. The second noise term probably cannot be gotten rid of either, since subtracting out $\bar{t}$ is necessary to remove the nuisance term $$\frac{1}{\beta}\log Q.$$

Again, note that, given the observation that each element of $\tilde{t}_j$ is an independent measurement of $$\frac{1}{\beta}(1-\log n_j),$$

it is clear that a UMVU (uniform minimum variance unbiased) estimate of $$\frac{1}{\beta}(1-\log n_j)$$

is just the average of the elements of $\tilde{t}_j$. (In the case in which each $\sigma_{ij}^2$ is different, it will be a weighted average.) Thus, performing a little bit of algebra, the UMVU estimator for $\log n_j$ is given by:

$$\frac{1}{n}\sum_i \tilde{t}_{ij} \approx \frac{1}{\beta}(1-\log n_j) \Rightarrow$$

$$\log n_j \approx 1 - \beta \cdot \frac{1}{n}\sum_{i,j}\tilde{t}_{ij} = 1 - \beta\left(\frac{1}{n}\sum_i t_{ij} - \frac{1}{mn}\sum_{i,j} t_{ij}\right)$$

Analysis Under the Complicated Model

Now repeat the preceding analysis with respect to a biochemical model in which each $\beta_{ij}$ and $\alpha_{ij}$ is different. Again, take noise into account and to see what remnants of noise survive in the construction of the matched filter f as well as in the construction of $\tilde{t}_j$. Under the complicated model, from (*) above:

$$\beta_{ij} t_{ij} = \log\frac{Q_T}{\alpha_{ij}} - \log n_j - \log Q + Z_{ij}$$

Which can be rewritten as:

$$(***)\; t_{ij} = \frac{1}{\beta_{ij}}\log\frac{Q_T}{\alpha_{ij}} - \frac{1}{\beta_{ij}}\log n_j - \frac{1}{\beta_{ij}}\log Q + Z_{ij}$$

The i-th component of the matched filter f is given by:

$$f_i \triangleq \Delta_i^Y - \Delta_i^X - \{t_{i,23}^Y - t_7^Y\} - \{(t_{i,23}^X - t_7^X\} =$$

$$\left\{\left(\frac{1}{\beta_{i,23}}\log\frac{Q_T}{\alpha_{i,23}} - \frac{1}{\beta_{i,23}}\log n_{23}^Y - \frac{1}{\beta_{i,23}}\log Q^Y + Z_{i,23}^Y\right) - \right.$$

$$\frac{1}{n}\sum_i\left(\frac{1}{\beta_{i,7}}\log\frac{Q_T}{\alpha_{i,7}} - \frac{1}{\beta_{i,7}}\log n_7^Y - \frac{1}{\beta_{i,7}}\log Q^Y + Z_{i,7}^Y\right)\right\} -$$

$$\left\{\left(\frac{1}{\beta_{i,23}}\log\frac{Q_T}{\alpha_{i,23}} - \frac{1}{\beta_{i,23}}\log n_{23}^X - \frac{1}{\beta_{i,23}}\log Q^X + Z_{i,23}^X\right) - \right.$$

$$\frac{1}{n}\sum_i\left(\frac{1}{\beta_{i,7}}\log\frac{Q_T}{\alpha_{i,7}} - \frac{1}{\beta_{i,7}}\log n_7^X - \frac{1}{\beta_{i,7}}\log Q^X + Z_{i,7}^X\right)\right\} = \frac{1}{\beta_{i,23}} +$$

$$\left(\frac{1}{\beta_{i,23}}-\left(\frac{1}{n}\sum_i\frac{1}{\beta_{i,7}}\right)\right)\log\frac{Q^Y}{Q^X} + \left\{Z_{i,23}^Y - Z_{i,23}^X + \frac{1}{n}\sum_i Z_{i,7}^X - \frac{1}{n}\sum_i Z_{i,7}^Y\right\}$$

Under the complicated model, this gives:

$$\tilde{t}_{ij} \triangleq t_j - \bar{t} = \left\{\frac{1}{B_{ij}}\log\frac{Q_T}{\alpha_{ij}} - \frac{1}{\beta_{ij}}\log n_j - \frac{1}{\beta_{ij}}\log Q + Z_{ij}\right\} -$$

$$\frac{1}{mn}\sum_{i,j}\left\{\frac{1}{\beta_{ij}}\log\frac{Q_T}{\alpha_{ij}} - \frac{1}{\beta_{ij}}\log n_j - \frac{1}{\beta_{ij}}\log Q + Z_{ij}\right\}$$

An Alternate Way to Regularize CT Values

In another embodiment of the method, one can average the CT values rather than transforming to exponential scale and then taking logs, as this distorts the noise so that it is no longer zero mean. First, start with known Q and solve for betas. Then do multiple experiments with known n_j to solve for alphas. Since aneuploidy is a whole set of hypotheses, it is convenient to use ML to determine the most likely n_j and Q values, and then use this as a basis for calculating the most likely aneuploid state, e.g., by taking the n_j value that is most off from 1 and pushing it to its nearest aneuploid neighbor.

Estimation of the Error Rates in the Embryonic Measurements.

In one embodiment of the invention, it is possible to determine the conditional probabilities of particular embryonic measurements given specific underlying true states in embryonic DNA. In certain contexts, the given data consists of (i) the data about the parental SNP states, measured with a high degree of accuracy, and (ii) measurements on all of the SNPs in a specific blastomere, measured poorly.

Use the following notation: U—is any specific homozygote, $\bar{U}$ is the other homozygote at that SNP, H is the heterozygote. The goal is to determine the probabilities ($p_{ij}$) shown in Table 2. For instance $p_{11}$ is the probability of the embryonic DNA being U and the readout being U as well. There are three conditions that these probabilities have to satisfy:

$$p_{11}+p_{12}+p_{13}+p_{14}=1 \quad (1)$$

$$p_{21}+p_{22}+p_{23}+p_{24}=1 \quad (2)$$

$$p_{21}=p_{23} \quad (3)$$

The first two are obvious, and the third is the statement of symmetry of heterozygote dropouts (H should give the same dropout rate on average to either U or $\bar{U}$).

There are 4 possible types of matings: U×U, U×$\bar{U}$, U×H, H×H. Split all of the SNPs into these 4 categories depending on the specific mating type. Table 3 shows the matings, expected embryonic states, and then probabilities of specific readings ($p_{ij}$). Note that the first two rows of this table are the same as the two rows of the Table 2 and the notation ($p_{ij}$) remains the same as in Table 2.

Probabilities $p_{3i}$ and $p_{4i}$ can be written out in terms of $p_{1i}$ and $p_{2i}$.

$$p_{31}=\tfrac{1}{2}[p_{11}+p_{21}] \quad (4)$$

$$p_{32}=\tfrac{1}{2}[p_{12}+p_{22}] \quad (5)$$

$$p_{33}=\tfrac{1}{2}[p_{13}+p_{23}] \quad (6)$$

$$p_{34}=\tfrac{1}{2}[p_{14}+p_{24}] \quad (7)$$

$$p_{41}=\tfrac{1}{4}[p_{11}+2p_{21}+p_{13}] \quad (8)$$

$$p_{42}=\tfrac{1}{2}[p_{12}+p_{22}] \quad (9)$$

$$p_{43}=\tfrac{1}{4}[p_{11}+2p_{23}+p_{13}] \quad (10)$$

$$p_{44}=\tfrac{1}{2}[p_{14}+p_{24}] \quad (11)$$

These can be thought of as a set of 8 linear constraints to add to the constraints (1), (2), and (3) listed above. If a vector $P=[p_{11}, p_{12}, p_{13}, p_{14}, p_{21} \ldots, p_{44}]^T$ (16×1 dimension) is defined, then the matrix A (11×16) and a vector C can be defined such that the constraints can be represented as:

$$AP=C \quad (12)$$

$C=[1, 1, 0, 0, 0, 0, 0, 0, 0, 0, 0, 0, 0, 0, 0, 0]^T$.
Specifically, A is shown in Table 4, where empty cells have zeroes.

The problem can now be framed as that of finding P that would maximize the likelihood of the observations and that is subject to a set of linear constraints (AP=C). The observations come in the same 16 types as $p_{ij}$. These are shown in Table 5. The likelihood of making a set of these 16 $n_{ij}$ observations is defined by a multinomial distribution with the probabilities $p_{ij}$ and is proportional to:

$$L(P, n_{ij}) \propto \prod_{ij} p_{ij}^{n_{ij}} \quad (13)$$

Note that the full likelihood function contains multinomial coefficients that are not written out given that these coefficients do not depend on P and thus do not change the values within P at which L is maximized. The problem is then to find:

$$\max_P [L(P, n_{ij})] = \max_P [\ln(L(P, n_{ij}))] = \max_P \left(\sum_{ij} n_{ij} \ln(p_{ij})\right) \quad (14)$$

subject to the constraints AP=C.

Note that in (14) taking the ln of L makes the problem more tractable (to deal with a sum instead of products). This is standard given that value of x such that f(x) is maximized is the same for which ln(f(x)) is maximized. $P(n_j,Q,D)=P(n_j)P(Q)P(D_j|Q,n_j)P(D_{k \neq j}|Q)$ D MAP Detection of Aneuploidy without Parents In one embodiment of the invention, the PS method can be applied to determine the number of copies of a given chromosome segment in a target without using parental genetic information. In this section, a maximum a-posteriori (MAP) method is described that enables the classification of genetic allele information as aneuploid or euploid. The method does not require parental data, though when parental data are available the classification power is enhanced. The method does not require regularization of channel values. One way to determine the number of copies of a chromosome segment in the genome of a target individual by incorporating the genetic data of the target individual and related individual(s) into a hypothesis, and calculating the most likely hypothesis is described here. In this description, the method will be applied to ct values from TAQMAN measurements; it should be obvious to one skilled in the art how to apply this method to any kind of measurement from any platform. The description will focus on the case in which there are measurements on just chromosomes X and 7; again, it should be obvious to one skilled in the art how to apply the method to any number of chromosomes and sections of chromosomes.

Setup of the Problem

The given measurements are from triploid blastomeres, on chromosomes X and 7, and the goal is to successfully make aneuploidy calls on these. The only "truth" known about these blastomeres is that there must be three copies of chromosome 7. The number of copies of chromosome X is not known.

The strategy here is to use MAP estimation to classify the copy number $N_7$ of chromosome 7 from among the choices {1,2,3} given the measurements D. Formally that looks like this:

$$\hat{n}_7 = \underset{n_7 \in \{1,2,3\}}{\operatorname{argmax}} P(n_7, D)$$

Unfortunately, it is not possible to calculate this probability, because the probability depends on the unknown quantity Q. If the distribution $f$ on Q were known, then it would be possible to solve the following:

$$\hat{n}_7 = \underset{n_7 \in \{1,2,3\}}{\operatorname{argmax}} \int f(Q) P(n_7, D \mid Q) dQ$$

In practice, a continuous distribution on Q is not known. However, identifying Q to within a power of two is sufficient, and in practice a probability mass function (pmf) on Q that is uniform on say $\{2^1, 2^2 \ldots, 2^{40}\}$ can be used. In the development that follows, the integral sign will be used as though a probability distribution function (pdf) on Q were known, even though in practice a uniform pmf on a handful of exponential values of Q will be substituted.

This discussion will use the following notation and definitions:

- $N_7$ is the copy number of chromosome seven. It is a random variable. $n_7$ denotes a potential value for $N_7$.
- $N_X$ is the copy number of chromosome X. $n_X$ denotes a potential value for $N_X$.
- $N_j$ is the copy number of chromosome-j, where for the purposes here $j \in \{7, X\}$. $n_j$ denotes a potential value for $N_j$.
- D is the set of all measurements. In one case, these are TAQMAN measurements on chromosomes X and 7, so this gives $D = \{D_7, D_X\}$, where $D_j = \{t_{ij}^A, t_{ij}^C\}$ is the set of TAQMAN measurements on this chromosome.
- $t_{ij}^A$ is the ct value on channel-A of locus i of chromosome-j. Similarly, $t_{ij}^C$ is the ct value on channel-C of locus i of chromosome-j. (A is just a logical name and denotes the major allele value at the locus, while C denotes the minor allele value at the locus.)
- Q represents a unit-amount of genetic material such that, if the copy number of chromosome-j is $n_j$, then the total amount of genetic material at any locus of chromosome-j is $n_j Q$. For example, under trisomy, if a locus were AAC, then the amount of A-material at this locus would be 2Q, the amount of C-material at this locus is Q, and the total combined amount of genetic material at this locus is 3Q.
- $(n^A, n^C)$ denotes an unordered allele patterns at a locus when the copy number for the associate chromosome is n. $n^A$ is the number of times allele A appears on the locus and $n^C$ is the number of times allele C appears on the locus. Each can take on values in $0, \ldots, n$, and it must be the case that $n^A + n^C = n$. For example, under trisomy, the set of allele patterns is $\{(0,3), (1,2), (2,1), (3,0)\}$. The allele pattern (2,1) for example corresponds to a locus value of $A^2C$, i.e., that two chromosomes have allele value A and the third has an allele value of C at the locus. Under disomy, the set of allele patterns is $\{(0,2), (1,1), (2,0)\}$. Under monosomy, the set of allele patterns is $\{(0,1), (1,0)\}$.
- $Q_T$ is the (known) threshold value from the fundamental TAQMAN equation $Q_0 2^{\beta t} = Q_T$.
- $\beta$ is the (known) doubling-rate from the fundamental TAQMAN equation $Q_0 2^{\beta t} = Q_T$.
- $\perp$ (pronounced "bottom") is the ct value that is interpreted as meaning "no signal".
- $f_Z(x)$ is the standard normal Gaussian pdf evaluated at x.
- $\sigma$ is the (known) standard deviation of the noise on TAQMAN ct values.

MAP Solution

In the solution below, the following assumptions have been made:

$N_7$ and $N_X$ are independent.

Allele values on neighboring loci are independent.

The goal is to classify the copy number of a designated chromosome. In this case, the description will focus on chromosome 7. The MAP solution is given by:

$$\hat{n}_7 = \underset{n_7 \in \{1,2,3\}}{\operatorname{argmax}} \int f(Q) P(n_7, D \mid Q) dQ$$

$$= \underset{n_7 \in \{1,2,3\}}{\operatorname{argmax}} \int f(Q) \sum_{n_X \in \{1,2,3\}} P(n_7, n_X, D \mid Q) dQ$$

$$= \underset{n_7 \in \{1,2,3\}}{\operatorname{argmax}} \int f(Q) \sum_{n_X \in \{1,2,3\}} P(n_7) P(n_X) P(D_7 \mid Q, n_7) P(D_X \mid Q, n_X) dQ$$

$$= \underset{n_7 \in \{1,2,3\}}{\operatorname{argmax}} \int f(Q) (P(n_7) P(D_7 \mid Q, n_7)) \left( \sum_{n_X \in \{1,2,3\}} P(n_X) P(D_X \mid Q, n_X) \right) dQ$$

$$= \underset{n_7 \in \{1,2,3\}}{\operatorname{argmax}} \int f(Q) \left( P(n_7) \prod_i P(t_{i,7}^A, t_{i,7}^C \mid Q, n_7) \right) \left( \sum_{n_Z \in \{1,2,3\}} P(n_X) \prod_i P(t_{i,X}^A, t_{i,X}^C \mid Q, n_X) \right) dQ (*)$$

$$= \underset{n_7 \in \{1,2,3\}}{\operatorname{argmax}} \int f(Q)$$

$$\left( P(n_7) \prod_i \sum_{n^A + n^C = n_7} P(n^A, n^C \mid n_7, i) P(t_{i,7}^A \mid Q, n^A) P(t_{i,7}^C \mid Q, n^C) \right) \times$$

-continued $$\left(\sum_{n_X \in \{1,2,3\}} P(n_X) \prod_i \sum_{n^A + n^C = n_X} P(n^A, n^C \mid n_X, i) P(t_{i,X}^A \mid Q, n^A) P(t_{i,X}^C \mid Q, n^C)\right) dQ$$

Allele Distribution Model

Equation (*) depends on being able to calculate values for $P(n^A, n^C \mid n_7, i)$ and $P(n^A, n^C \mid n_X, i)$. These values may be calculated by assuming that the allele pattern $(n^A, n^C)$ is drawn i.i.d (independent and identically distributed) according to the allele frequencies for its letters at locus i. An example should suffice to illustrate this. Calculate $P((2,1) \mid n_7 = 3)$ under the assumption that the allele frequency for A is 60%, and the minor allele frequency for C is 40%. (As an aside, note that $P((2,1) \mid n_7 = 2) = 0$, since in this case the pair must sum to 2.) This probability is given by $$P((2, 1) \mid n_7 = 3) = \binom{3}{2}(.60)^2(.40)$$

The general equation is $$P(n^A, n^C \mid n_j, i) = \binom{n}{n^A}(1 - p_{ij})^{n^A}(p_{ij})^{n^C}$$

Where $p_{i,j}$ is the minor allele frequency at locus i of chromosome j.

Error Model

Equation (*) depends on being able to calculate values for $P(t^A \mid Q, n^A)$ and $P(t^C \mid Q, n^C)$. For this an error model is needed. One may use the following error model:

$$P(t^A \mid Q, n^A) = \begin{cases} p_d & t^A = \perp \text{ and } n^A > 0 \\ (1 - p_a)f_Z\left(\frac{1}{\sigma}\left(t^A - \frac{1}{\beta}\log\frac{Q_T}{n^A Q}\right)\right) & t^A \neq \perp \text{ and } n^A > 0 \\ 1 - p_a & t^A = \perp \text{ and } n^A = 0 \\ 2p_a f_Z\left(\frac{1}{\sigma}(t^A - \perp)\right) & t^A \neq \perp \text{ and } n^A = 0 \end{cases}$$

Each of the four cases mentioned above is described here. In the first case, no signal is received, even though there was A-material on the locus. That is a dropout, and its probability is therefore $p_d$. In the second case, a signal is received, as expected since there was A-material on the locus. The probability of this is the probability that a dropout does not occur, multiplied by the pdf for the distribution on the ct value when there is no dropout. (Note that, to be rigorous, one should divide through by that portion of the probability mass on the Gaussian curve that lies below ⊥, but this is practically one, and will be ignored here.) In the third case, no signal was received and there was no signal to receive. This is the probability that no drop-in occurred, $1 - p_a$. In the final case, a signal is received even through there was no A-material on the locus. This is the probability of a drop-in multiplied by the pdf for the distribution on the ct value when there is a drop-in. Note that the '2' at the beginning of the equation occurs because the Gaussian distribution in the case of a drop-in is modeled as being centered at ⊥. Thus, only half of the probability mass lies below ⊥ in the case of a drop-in, and when the equation is normalized by dividing through by one-half, it is equivalent to multiplying by 2. The error model for $P(t^C \mid Q, n^C)$ by symmetry is the same as for $P(t^A \mid Q, n^A)$ above. It should be obvious to one skilled in the art how different error models can be applied to a range of different genotyping platforms, for example the ILLUMINA INFINIUM genotyping platform.

Computational Considerations

In one embodiment of the invention, the MAP estimation mathematics can be carried out by brute-force as specified in the final MAP equation, except for the integration over Q. Since doubling Q only results in a difference in ct value of $1/\beta$, the equations are sensitive to Q only on the log scale. Therefore to do the integration it should be sufficient to try a handful of Q-values at different powers of two and to assume a uniform distribution on these values. For example, one could start at $Q = Q_T 2^{-20\beta}$, which is the quantity of material that would result in a ct value of 20, and then halve it in succession twenty times, yielding a final Q value that would result in a ct value of 40.

What follows is a re-derivation of a derivation described elsewhere in this disclosure, with slightly difference emphasis, for elucidating the programming of the math. Note that the variable D below is not really a variable. It is always a constant set to the value of the data set actually in question, so it does not introduce another array dimension when representing in MATLAB. However, the variables $D_j$ do introduce an array dimension, due to the presence of the index j.

$$\hat{n}_7 = \underset{n_7 \in \{1,2,3\}}{\operatorname{argmax}} P(n_7, D)$$

$$P(n_7, D) = \sum_Q P(n_7, Q, D)$$

$$P(n_7, Q, D) = P(n_7)P(Q)P(D_7 \mid Q, n_7)P(D_X \mid Q)$$

$$P(D_j \mid Q) = \sum_{n_j \in \{1,2,3\}} P(D_j, n_j \mid Q)$$

$$P(D_j, n_j \mid Q) = P(n_j)P(D_j \mid Q, n_j)$$

$$P(D_j \mid Q, n_j) = \prod_i P(D_{ij} \mid Q, n_j)$$

$$P(D_{ij} \mid Q, n_j) = \sum_{n^A + n^C = n_j} P(D_{ij}, n^A, n^C \mid Q, n_j)$$

$$P\begin{pmatrix} D_{ij}, n^A, \\ n^C \mid Q, n_j \end{pmatrix} = P(n^A, n^C \mid n_j, i) P(t_{ij}^A \mid Q, n^A) P(t_{ij}^C \mid Q, n^C)$$

$$P(n^A, n^C \mid n_j, i) = \binom{n}{n^A}(1 - p_{ij})^{n^A}(p_{ij})^{n^C}$$

$$P\begin{pmatrix} t_{ij}^A \mid Q, \\ n^A \end{pmatrix} = \begin{cases} p_d & t^A = \perp \text{ and } n^A > 0 \\ (1 - p_d)f_Z\left(\frac{1}{\sigma}\left(t^A - \frac{1}{\beta}\log\frac{Q_T}{n^A Q}\right)\right) & t^A \neq \perp \text{ and } n^A > 0 \\ 1 - p_a & t^A = \perp \text{ and } n^A = 0 \\ 2p_z f_Z\left(\frac{1}{\sigma}(t^A - \perp)\right) & t^A \neq \perp \text{ and } n^A = 0 \end{cases}$$

E MAP Detection of Aneuploidy with Parental Info

In one embodiment of the invention, the disclosed method enables one to make aneuploidy calls on each chromosome of each blastomere, given multiple blastomeres with measurements at some loci on all chromosomes, where it is not known how many copies of each chromosome there are. In this embodiment, the a MAP estimation is used to classify the copy number $N_j$ of chromosome where $j \in \{1,2 \ldots 22,X,Y\}$, from among the choices $\{0, 1, 2, 3\}$ given the measurements D, which includes both genotyping information of the blastomeres and the parents. To be general, let $j \in \{1,2 \ldots m\}$ where m is the number of chromosomes of interest; m=24 implies that all chromosomes are of interest. Formally, this looks like:

$$\hat{n}_j = \underset{n_j \in \{1,2,3\}}{\operatorname{argmax}} P(n_j, D)$$

Unfortunately, it is not possible to calculate this probability, because the probability depends on an unknown random variable Q that describes the amplification factor of MDA. If the distribution $f$ on Q were known, then it would be possible to solve the following:

$$\hat{n}_j = \underset{n_j \in \{1,2,3\}}{\operatorname{argmax}} \int f(Q) P(n_j, D \mid Q) dQ$$

In practice, a continuous distribution on Q is not known. However, identifying Q to within a power of two is sufficient, and in practice a probability mass function (pmf) on Q that is uniform on say $\{2^1, 2^2 \ldots, 2^{40}\}$ can be used. In the development that follows, the integral sign will be used as though a probability distribution function (pdf) on Q were known, even though in practice a uniform pmf on a handful of exponential values of Q will be substituted.

This discussion will use the following notation and definitions:

$N_\alpha$ is the copy number of autosomal chromosome $\alpha$, where $\alpha \in \{1, 2 \ldots 22\}$. It is a random variable. $n_\alpha$ denotes a potential value for $N_\alpha$.

$N_X$ is the copy number of chromosome X. $n_X$ denotes a potential value for $N_X$.

$N_j$ is the copy number of chromosome-j, where for the purposes here $j \in \{1,2 \ldots m\}$. $n_j$ denotes a potential value for $N_j$.

m is the number of chromosomes of interest, m=24 when all chromosomes are of interest.

H is the set of aneuploidy states. $h \in H$. For the purposes of this derivation, let H={paternal monosomy, maternal monosomy, disomy, t1 paternal trisomy, t2 paternal trisomy, t1 maternal trisomy, t2 maternal trisomy}. Paternal monosomy means the only existing chromosome came from the father; paternal trisomy means there is one additional chromosome coming from father. Type 1 (t1) paternal trisomy is such that the two paternal chromosomes are sister chromosomes (exact copy of each other) except in case of crossover, when a section of the two chromosomes are the exact copies. Type 2 (t2) paternal trisomy is such that the two paternal chromosomes are complementary chromosomes (independent chromosomes coming from two grandparents). The same definitions apply to the maternal monosomy and maternal trisomies.

D is the set of all measurements including measurements on embryo $D_E$ and on parents $D_F, D_M$. In the case where these are TAQMAN measurements on all chromosomes, one can say: $D=\{D_1, D_2 \ldots D'_m\}$, $D_E=\{D_{E,1}, D_{E,2} \ldots D_{E,m}\}$, where $D_k=(D_{E,k}, D_{F,k}, D_{M,k})$, $D_{Ej}=\{t_{E,ij}{}^A, t_{E,ij}{}^C\}$ is the set of TAQMAN measurements on chromosome j.

$t_{E,ij}{}^A$ is the ct value on channel-A of locus i of chromosome-j. Similarly, $t_{E,ij}{}^C$ is the ct value on channel-C of locus i of chromosome-j. (A is just a logical name and denotes the major allele value at the locus, while C denotes the minor allele value at the locus.)

Q represents a unit-amount of genetic material after MDA of single cell's genomic DNA such that, if the copy number of chromosome-j is $n_j$, then the total amount of genetic material at any locus of chromosome-j is $n_j Q$. For example, under trisomy, if a locus were AAC, then the amount of A-material at this locus is 2Q, the amount of C-material at this locus is Q, and the total combined amount of genetic material at this locus is 3Q.

q is the number of numerical steps that will be considered for the value of Q.

N is the number of SNPs per chromosome that will be measured.

$(n^A, n^C)$ denotes an unordered allele patterns at a locus when the copy number for the associated chromosome is n. $n^A$ is the number of times allele A appears on the locus and $n^C$ is the number of times allele C appears on the locus. Each can take on values in $0, \ldots, n$, and it must be the case that $n^A + n^C = n$. For example, under trisomy, the set of allele patterns is $\{(0,3),(1,2),(2,1),(3,0)\}$. The allele pattern $(2,1)$ for example corresponds to a locus value of $A^2C$, i.e., that two chromosomes have allele value A and the third has an allele value of C at the locus. Under disomy, the set of allele patterns is $\{(0,2),(1,1),(2,0)\}$. Under monosomy, the set of allele patterns is $\{(0,1),(1,0)\}$.

$Q_T$ is the (known) threshold value from the fundamental TAQMAN equation $Q_0 2^{\beta t} = Q_T$.

$\beta$ is the (known) doubling-rate from the fundamental TAQMAN equation $Q_0 2^{\beta t} = Q_T$.

$\perp$ (pronounced "bottom") is the ct value that is interpreted as meaning "no signal".

$f_Z(x)$ is the standard normal Gaussian pdf evaluated at x.

$\sigma$ is the (known) standard deviation of the noise on TAQMAN ct values.

MAP Solution

In the solution below, the following assumptions are made:

$N_j$s are independent of one another.

Allele values on neighboring loci are independent.

The goal is to classify the copy number of a designated chromosome. For instance, the MAP solution for chromosome a is given by $$\begin{aligned}
\hat{n}_j &= \underset{n_j \in \{1,2,3\}}{\operatorname{argmax}} \int f(Q) P(n_j, D \mid Q) dQ \\
&= \underset{n_j \in \{1,2,3\}}{\operatorname{argmax}} \int f(Q) \sum_{n_1 \in \{1,2,3\}} \cdots \sum_{n_{j-1} \in \{1,2,3\}} \sum_{n_{j+1} \in \{1,2,3\}} \cdots \\
&\quad \sum_{n_m \in \{1,2,3\}} P(n_1, \ldots n_m, D \mid Q) dQ \\
&= \underset{n_j \in \{1,2,3\}}{\operatorname{argmax}} \int f(Q) \sum_{n_1 \in \{1,2,3\}} \cdots \sum_{n_{j-1} \in \{1,2,3\}} \sum_{n_{j+1} \in \{1,2,3\}} \cdots \\
&\quad \sum_{n_m \in \{1,2,3\}} \prod_{k=1}^{m} P(n_k) P(D_k \mid Q, n_k) dQ
\end{aligned}$$

-continued $$= \underset{n_j \in \{1,2,3\}}{\operatorname{argmax}} \int f(Q)(P(n_j)P(D_j|Q,n_j))$$

$$\left(\prod_{k \neq j} \sum_{n_k \in \{1,2,3\}} P(n_k)P(D_k|Q,n_k)\right) dQ$$

$$= \underset{n_j \in \{1,2,3\}}{\operatorname{argmax}} \int f(Q)\left(P(n_j)\sum_{h \in H} P(D_j|Q,n_j,h)P(h|n_j)\right)$$

$$\left(\prod_{k \neq j} \sum_{n_k \in \{1,2,3\}} P(n_k) \sum_{h \in H} P(D_k|Q,n_k,h)P(h|n_k)\right) dQ$$

$$= \underset{n_j \in \{1,2,3\}}{\operatorname{argmax}} \int f(Q)$$

$$\left(P(n_j) \sum_{h \in H} P(h|n_j) \prod_i P(t^A_{E,ij}, t^C_{E,ij}, D_{F,ij}D_{M,ij}|Q,n_j,h)\right) \times$$

$$\left(\prod_{k \neq j} \sum_{n_k \in \{1,2,3\}} P(n_k) \sum_{h \in H} P(h|n_k)\right)$$

$$\prod_i P(t^A_{E,ik}, t^C_{E,ik}, D_{F,ik}D_{M,ik}|Q,n_k,h)) dQ$$

$$= \underset{n_j \in \{1,2,3\}}{\operatorname{argmax}} \int f(Q)$$

$$(P(n_j) \sum_{h \in H} P(h|n_j) \prod_i \sum_{\substack{n^A_F + n^C_F = 2 \\ n^A_M + n^C_M = 2}} P(n^A_F, n^C_F, n^A_M, n^C_M)$$

$$P(t^A_{E,ij}, t^C_{E,ij}, D_{F,ij}D_{M,ij}|Q,n_j,h,n^A_F,n^C_F,n^A_M,n^C_M)) \times$$

$$\left(\prod_{k \neq j} \sum_{n_k \in \{1,2,3\}} P(n_k) \sum_{h \in H} P(h|n_k)\right)$$

$$\prod_i \sum_{\substack{n^A_F + n^C_F = 2 \\ n^A_M + n^C_M = 2}} P(n^A_F, n^C_F, n^A_M, n^C_M)$$

$$P(t^A_{E,ik}, t^C_{E,ik}, D_{F,ik}D_{M,ik}|Q,n_k,h,n^A_F,n^C_F,n^A_M,n^C_M)) dQ$$

$$= \underset{n_1 \in \{1,2,3\}}{\operatorname{argmax}} \int f(Q)(P(n_j) \sum_{h \in H} P(h|n_j)$$

$$\prod_i \sum_{\substack{n^A_F + n^C_F = 2 \\ n^A_K + n^C_K = 2}} P(n^A_F, n^C_F, n^A_M, n^C_M)$$

$$P(t^A_{F,ij}|n^A_F Q')P(t^C_{F,ij}|n^C_F Q')P(t^A_{M,ij}|n^A_M Q')$$

$$P(t^C_{M,ij}|n^C_N Q') \times \sum_{n^A + n^C = n_j} P(n^A, n^C|n_j, h, n^A_F, n^C_F, n^A_M, n^C_M)$$

$$P(t^A_{E,ij}|Q, n^A)P(t^C_{E,ij}|Q, n^C)) \times$$

$$\left(\prod_{k \neq j} \sum_{n_k \in \{1,2,3\}} P(n_k) \sum_{h \in H} P(h|n_k)\right)$$

$$\prod_t \sum_{\substack{n^A_F + n^C_F = 2 \\ n^A_M + n^C_M = 2}} P(n^A_F, n^C_F, n^A_M, n^C_M)P(\tau^A_{F,ik}|n^A_F Q')$$

$$P(\tau^C_{F,ik}|n^C_F Q')P(\tau^A_{M,ik}|n^A_M Q')P(\tau^C_{m,ik}|n^C_M Q') \times$$

$$\sum_{n^A + n^C = n_1} P(n^A, n^C|n_k, h, n^A_F, n^C_F, n^A_M, n^C_M)P(\tau^A_{E,ik}|n^A Q)$$

$$P(t^C_{E,ik}|n^C Q)) dQ \quad (*)$$

Here it is assumed that Q', the Q are known exactly for the parental data.

Copy Number Prior Probability

Equation (*) depends on being able to calculate values for $P(n_\alpha)$ and $P(n_X)$, the distribution of prior probabilities of chromosome copy number, which is different depending on whether it is an autosomal chromosome or chromosome X. If these numbers are readily available for each chromosome, they may be used as is. If they are not available for all chromosomes, or are not reliable, some distributions may be assumed. Let the prior probability $$P(n_a = 1) = P(n_a = 2) = P(n_a = 3) = \frac{1}{3}$$

for autosomal chromosomes, let the probability of sex chromosomes being XY or XX be ½.

$$P(n_X = 0) = \frac{1}{3} \times \frac{1}{4} = \frac{1}{12}.$$

$$P(n_X = 1) = \frac{1}{3} \times \frac{3}{4} + \frac{1}{3} \times \frac{1}{2} + \frac{1}{3} \times \frac{1}{2} \times \frac{1}{4} = \frac{11}{24} = 0.458,$$

where ¾ is the probability of the monosomic chromosome being X (as oppose to Y), ½ is the probability of being XX for two chromosomes and ¼ is the probability of the third chromosome being Y.

$$P(n_X = 3) = \frac{1}{3} \times \frac{1}{2} \times \frac{3}{4} = \frac{1}{8} = 0.125,$$

where ½ is the probability of being XX for two chromosomes and ¾ is the probability of the third chromosome being X.

$$P(n_X = 2) = 1 - P(n_X = 0) - P(n_X = 1) - P(n_X = 3) = \frac{4}{12} = 0.333.$$

Aneuploidy State Prior Probability

Equation (*) depends on being able to calculate values for $P(h|n_j)$, and these are shown in Table 6. The symbols used in the Table 6 are explained below

| Symbol | Meaning |
| --- | --- |
| Ppm | paternal monosomy probability |
| Pmm | maternal monosomy probability |
| Ppt | paternal trisomy probability given trisomy |
| Pmt | maternal trisomy probability given trisomy |
| pt1 | probability of type 1 trisomy for paternal trisomy, or P(type 1\|paternal trisomy) |
| pt2 | probability of type 2 trisomy for paternal trisomy, or P(type 2\|paternal trisomy) |
| mt1 | probability of type 1 trisomy for maternal trisomy, or P(type 1\|maternal trisomy) |
| mt2 | probability of type 2 trisomy for maternal trisomy, or P(type 2\|maternal trisomy) |

Note that there are many other ways that one skilled in the art, after reading this disclosure, could assign or estimate appropriate prior probabilities without changing the essential concept of the patent.

Allele Distribution Model without Parents

Equation (*) depends on being able to calculate values for $p(n^A, n^C|n_\alpha, i)$ and $P(n^A, n^C|n_X, i)$. These values may be calculated by assuming that the allele pattern $(n^A, n^C)$ is drawn i.i.d according to the allele frequencies for its letters at locus i. An illustrative example is given here. Calculate $P((2,1)|n_7=3)$ under the assumption that the allele frequency for A is 60%, and the minor allele frequency for C is 40%. (As an aside, note that $P((2,1)|n_7=2)=0$, since in this case the pair must sum to 2.) This probability is given by $$P((2,1)|n_7=3) = \binom{3}{2}(.60)^2(.40)$$

The general equation is $$P(n^A, n^C | n_j, i) = \binom{n}{n^A}(1-p_{ij})^{n^A}(p_{ij})^{n^C}$$

Where $p_{ij}$ is the minor allele frequency at locus i of chromosome j.

Allele Distribution Model Incorporating Parental Genotypes

Equation (*) depends on being able to calculate values for $p(n^A,n^C|n_j,h,T_{P,ij}T_{M,ij})$ which are listed in Table 7. In a real situation, LDO will be known in either one of the parents, and the table would need to be augmented. If LDO are known in both parents, one can use the model described in the Allele Distribution Model without Parents section.

Population Frequency for Parental Truth

Equation (*) depends on being able to calculate $p(T_{FA,j}T_{MA,j})$. The probabilities of the combinations of parental genotypes can be calculated based on the population frequencies. For example, $P(AA,AA)=P(A)^4$, and $P(AC,AC)= P_{heteroz}^2$ where $P_{heteroz}=2P(A)P(C)$ is the probability of a diploid sample to be heterozygous at one locus i.

Error Model

Equation (*) depends on being able to calculate values for $P(t^A|Q,n^A)$ and $P(t^C|Q,n^C)$. For this an error model is needed. One may use the following error model:

$$P(t^A|Q,n^A) = \begin{cases} p_d & t^A = \perp \text{ and } n^A > 0 \\ (1-p_d)f_Z\left(\frac{1}{\sigma}\left(t^A - \frac{1}{\beta}\log\frac{Q_T}{n^A Q}\right)\right) & t^A \neq \perp \text{ and } n^A > 0 \\ 1-p_a & t^A = \perp \text{ and } n^A = 0 \\ 2p_a f_Z\left(\frac{1}{\sigma}(t^A - \perp)\right) & t^A \neq \perp \text{ and } n^A = 0 \end{cases}$$

This error model is used elsewhere in this disclosure, and the four cases mentioned above are described there. The computational considerations of carrying out the MAP estimation mathematics can be carried out by brute-force are also described in the same section.

Computational Complexity Estimation

Rewrite the equation (*) as follows, $$\hat{n}_j = \underset{n_j \in \{1,2,3\}}{\operatorname{argmax}} \int f(Q) \left( \begin{array}{c} P(n_j)\prod_i \sum_{n^A+n^C=n_j} P(n^A,n^C|n_j,i) \\ P(t_{i,j}^A|Q,n^A)P(t_{i,j}^C|Q,n^C) \end{array} \right) \times$$

$$\left( \begin{array}{c} \prod_{k \neq j} \sum_{n_k \in \{1,2,3\}} P(n_k) \prod_i \sum_{n^A+n^C=n_k} \\ P(n^A,n^C|n_k,i)P(t_{i,k}^A|Q,n^A)P(t_{i,k}^C|Q,n^C) \end{array} \right) dQ \quad (*)$$

Let the computation time for $P(n^A,n^C|n_j,i)$ be $t_x$, that for $P(t_{i,j}^A|Q,n^A)$ or $P(t_{i,j}^C|Q,n^C)$ be $t_y$. Note that $P(n^A,n^C|n_j,i)$ may be pre-computed, since their values don't vary from experiment to experiment. For the discussion here, call a complete 23-chromosome aneuploidy screen an "experiment". Computation of $\Pi_i \Sigma_{n^A+n^C=n_j} P(n^A,n^C|n_j,i)P(t_{i,j}^A|Q,n^A)P(t_{i,j}^C|Q,n^C)$ for 23 chromosomes takes if $n_j=1$, $(2+t_x+2*t_y)*2N*m$
if $n_j=2$, $(2+t_x+2*t_y)*3N*m$
if $n_j=3$, $(2+t_x+2*t_y)*4N*m$ The unit of time here is the time for a multiplication or an addition.

In total, it takes $(2+t_x+2*t_y)*9N*m$

Once these building blocks are computed, the overall integral may be calculated, which takes time on the order of $(2+t_x+2*t_y)*9N*m*q$. In the end, it takes $2*m$ comparisons to determine the best estimate for $n_j$. Therefore, overall the computational complexity is $O(N*m*q)$.

What follows is a re-derivation of the original derivation, with a slight difference in emphasis in order to elucidate the programming of the math. Note that the variable D below is not really a variable. It is always a constant set to the value of the data set actually in question, so it does not introduce another array dimension when representing in MATLAB. However, the variables $D_j$ do introduce an array dimension, due to the presence of the index j.

$$\hat{n}_j = \underset{n_j \in \{1,2,3\}}{\operatorname{argmax}} P(n_j, D)$$

$$P(n_j, D) = \sum_Q P(n_j, Q, D)$$

$$P(n_j, Q, D) = P(n_j)P(Q)P(D_j|Q,n_j)P(D_{k \neq j}|Q)$$

$$P(D_j|Q) = \sum_{n_j \in \{1,2,3\}} P(D_j, n_j|Q)$$

$$P(D_j, n_j|Q) = P(n_j)P(D_j|Q,n_j)$$

$$P(D_j|Q,n_j) = \prod_i P(D_{ij}|Q,n_j)$$

$$P(D_{ij}|Q,n_j) = \sum_{n^A+n^C=n_j} P(D_{ij}, n^A, n^C|Q,n_j)$$

$$P\left(\begin{array}{c} D_{ij}, n^A, \\ n^C|Q,n_j \end{array}\right) = P(n^A,n^C|n_j,i)P(t_{ij}^A|Q,n^A)P(t_{ij}^C|Q,n^C)$$

$$P(n^A,n^C|n_j,i) = \binom{n}{n^A}(1-p_{ij})^{n^A}(p_{ij})^{n^C}$$

$$P\left(\begin{array}{c} t_{ij}^A|Q, \\ n^A \end{array}\right) = \begin{cases} p_d & t^A = \perp \text{ and } n^A > 0 \\ (1-p_d)f_Z\left(\frac{1}{\sigma}\left(t^A - \frac{1}{\beta}\log\frac{Q_T}{n^A Q}\right)\right) & t^A \neq \perp \text{ and } n^A > 0 \\ 1-p_a & t^A = \perp \text{ and } n^A = 0 \\ 2p_z f_Z\left(\frac{1}{\sigma}(t^A - \perp)\right) & t^A \neq \perp \text{ and } n^A = 0 \end{cases}$$

F Qualitative Chromosome Copy Number Calling

One way to determine the number of copies of a chromosome segment in the genome of a target individual by incorporating the genetic data of the target individual and related individual(s) into a hypothesis, and calculating the most likely hypothesis is described here. In one embodiment of the invention, the aneuploidy calling method may be modified to use purely qualitative data. There are many approaches to solving this problem, and several of them are presented here. It should be obvious to one skilled in the art how to use other methods to accomplish the same end, and these will not change the essence of the disclosure.

Notation for Qualitative CNC

1. N is the total number of SNPs on the chromosome.
2. n is the chromosome copy number.
3. $n^M$ is the number of copies supplied to the embryo by the mother: 0, 1, or 2.
4. $n^F$ is the number of copies supplied to the embryo by the father: 0, 1, or 2.
5. $p_d$ is the dropout rate, and $f(p_d)$ is a prior on this rate.
6. $p_a$ is dropin rate, and $f(p_a)$ is a prior on this rate.
7. c is the cutoff threshold for no-calls.
8. $D=(x_k, y_k)$ is the platform response on channels X and Y for SNP k.
9. $D(c) = \{G(x_k, y_k); c\} = \{\hat{g}_k^{(c)}\}$ is the set of genotype calls on the chromosome. Note that the genotype calls depend on the no-call cutoff threshold c.
10. $\hat{g}_k^{(c)}$ is the genotype call on the k-th SNP (as opposed to the true value): one of AA, AB, BB, or NC (no-call).
11. Given a genotype call $\hat{g}$ at SNP k, the variables $(\hat{g}_X, \hat{g}_Y)$ are indicator variables (1 or 0), indicating whether the genotype $\hat{g}$ implies that channel X or Y has "lit up". Formally, $\hat{g}_X=1$ just in case $\hat{g}$ contains the allele A, and $\hat{g}_Y=1$ just in case $\hat{g}$ contains the allele B.
12. $M=\{g_k^M\}$ is the known true sequence of genotype calls on the mother. $g^M$ refers to the genotype value at some particular locus.
13. $F=\{g_k^F\}$ is the known true sequence of genotype calls on the father. $g^F$ refers to the genotype value at some particular locus.
14. $n^A, n^B$ are the true number of copies of A and B on the embryo (implicitly at locus k), respectively. Values must be in $\{0,1,2,3,4\}$.
15. $c_M^A, c_M^B$ are the number of A alleles and B alleles respectively supplied by the mother to the embryo (implicitly at locus k). The values must be in $\{0, 1, 2\}$, and must not sum to more than 2. Similarly, $c_F^A, c_F^B$ are the number of A alleles and B alleles respectively supplied by the father to the embryo (implicitly at locus k). Altogether, these four values exactly determine the true genotype of the embryo. For example, if the values were (1,0) and (1,1), then the embryo would have type AAB.

Solution 1: Integrate Over Dropout and Dropin Rates.

In the embodiment of the invention described here, the solution applies to just a single chromosome. In reality, there is loose coupling among all chromosomes to help decide on dropout rate $p_d$, but the math is presented here for just a single chromosome. It should be obvious to one skilled in the art how one could perform this integral over fewer, more, or different parameters that vary from one experiment to another. It should also be obvious to one skilled in the art how to apply this method to handle multiple chromosomes at a time, while integrating over ADO and ADI. Further details are given in Solution 3B below.

$$P(n \mid D(c), M, F) = \sum_{(n^M, n^F) \in n} P(n^M, n^F \mid D(c), M, F)$$

-continued $$P\begin{pmatrix} n^M, n^F \mid D(c), \\ M, F \end{pmatrix} = \frac{P(D(c) \mid n^M, n^F, M, F) P(n^M) P(n^F)}{\sum_{(n^M, n^F)} P(n^M) P(n^F) P(D(c) \mid n^M, n^F, M, F)}$$

$$P\begin{pmatrix} D(c) \mid n^M, \\ n^F, M, F \end{pmatrix} = \int \int f(p_d) f(p_a) P\begin{pmatrix} D(c) \mid n^M, n^F, \\ M, F, p_d, p_a \end{pmatrix} dp_d dp_a$$

$$P\begin{pmatrix} D(c) \mid n^M, n^F, \\ M, F, p_d, p_a \end{pmatrix} = \prod_k P(G(x_k, y_k; c) \mid n^M, n^F, g_k^M, g_k^F, p_d, p_a)$$
$$= \prod_{\substack{g^M \in \{AA,AB,BB\} \\ g^F \in \{AA,AB,BB\} \\ \hat{g} \in \{AA,AB,BB,NC\}}} \prod_{\{k: g_k^M = g^M, g_k^F = g^F, \hat{g}_k^{(c)} = \hat{g}\}} P(\hat{g} \mid n^M, n^F, g^M, g^F, p_d, p_a)$$

$$= \prod_{\substack{g^M \in \{AA,AB,BB\} \\ g^F \in \{AA,AB,BB\} \\ \hat{g} \in \{AA,AB,BB,NC\}}} P\begin{pmatrix} \hat{g} \mid n^M, n^F, g^M, \\ g^F, p_d, p_a \end{pmatrix}^{\left|\left\{ \substack{k: g_k^M = g^M, \\ g_k^F = g^F, \hat{g}_k^{(c)} = \hat{g}} \right\}\right|}$$

$$= \exp\left( \sum_{\substack{g^M \in \{AA,AB,BB\} \\ g^F \in \{AA,AB,BB\} \\ \hat{g} \in \{AA,AB,BB,NC\}}} \left|\left\{ \substack{k: g_k^M = g^M, \\ g_k^F = g^F, \hat{g}_k^{(c)} = \hat{g}} \right\}\right| \times \log P(\hat{g} \mid n^M, n^F, g^M, g^F, p_d, p_a) \right)$$

$$P\begin{pmatrix} \hat{g} \mid n^M, n^F, g^M, \\ g^F, p_d, p_a \end{pmatrix} = \sum_{n^A, n^B} P\begin{pmatrix} n^A, n^B \mid n^M, \\ n^F, g^M, g^F \end{pmatrix} \overbrace{\begin{pmatrix} P(\hat{g}_X \mid n^A, p_d, p_a) \\ P(\hat{g}_Y \mid n^B, p_d, p_a) \end{pmatrix}}^{\text{platformmodeling}}$$
$$\underbrace{\phantom{xxxxxxxxxxxxxxxxxxxxxxxx}}_{\text{geneticmodeling}}$$

$$P\begin{pmatrix} \hat{g}_X \mid n^A, \\ p_d, p_a \end{pmatrix} = \left( \hat{g}_X \begin{pmatrix} (1 - p_d^{n^A}) + \\ (n^A = 0) p_a \end{pmatrix} + (1 - \hat{g}_X) \begin{pmatrix} (n^A > 0) p_d^{n^A} + \\ (n^A = 0)(1 - p_a) \end{pmatrix} \right)$$

The derivation other is the same, except applied to channel Y.

$$P\begin{pmatrix} n^A, n^B \mid n^M, \\ n^F, g^M, g^F \end{pmatrix} = \sum_{\substack{c_M^A + c_F^A = n^A \\ c_M^B + c_F^B = n^B}} P\begin{pmatrix} c_M^A, c_M^B \mid \\ n^M, g^M \end{pmatrix} P\begin{pmatrix} c_F^A, c_F^B \mid \\ n^F, g^F \end{pmatrix}$$

$$P(c_M^A, c_M^B \mid n^M, g^M) = (c_M^A + c_M^B = n^M) \begin{cases} (c_M^B = 0), & g^M = AA \\ (c_M^A = 0), & g^M = BB \\ \frac{1}{n^M + 1}, & g^M = AB \end{cases}$$

The other derivation is the same, except applied to the father.

Solution 2: Use ML to Estimate Optimal Cutoff Threshold c

Solution 2, Variation A $$\hat{c} = \underset{c \in (0,a]}{\operatorname{argmax}} P(D(c) \mid M, F)$$

$$P(n) = \sum_{(n^M, n^F) \in n} P(n^M, n^F \mid D(\hat{c}), M, F)$$

In this embodiment, one first uses the ML estimation to get the best estimate of the cutoff threshold based on the data, and then use this c to do the standard Bayesian inference as in solution 1. Note that, as written, the estimate of ĉ would still involve integrating over all dropout and dropin rates. However, since it is known that the dropout and dropin parameters tend to peak sharply in probability when they are "tuned" to their proper values with respect to c, one may save computation time by doing the following instead:

Solution 2, Variation B $$\hat{c}, \hat{p}_d, \hat{p}_a = \underset{c, p_d, p_a}{\operatorname{argmax}} f(p_d) f(p_a) P(D(c) \mid M, F, p_d, p_a)$$

$$P(n) = \sum_{(n^M, n^F) \in n} P(n^M, n^F \mid D(\hat{c}), M, F, \hat{p}_d, \hat{p}_a)$$

In this embodiment, it is not necessary to integrate a second time over the dropout and dropin parameters. The equation goes over all possible triples in the first line. In the second line, it just uses the optimal triple to perform the inference calculation.

Solution 3: Combining Data Across Chromosomes

The data across different chromosomes is conditionally independent given the cutoff and dropout/dropin parameters, so one reason to process them together is to get better resolution on the cutoff and dropout/dropin parameters, assuming that these are actually constant across all chromosomes (and there is good scientific reason to believe that they are roughly constant). In one embodiment of the invention, given this observation, it is possible to use a simple modification of the methods in solution 3 above. Rather than independently estimating the cutoff and dropout/dropin parameters on each chromosome, it is possible to estimate them once using all the chromosomes.

Notation

Since data from all chromosomes is being combined, use the subscript j to denote the j-th chromosome. For example, $D_j(c)$ is the genotype data on chromosome j using c as the no-call threshold. Similarly, $M_j, F_j$ are the genotype data on the parents on chromosome j.

Solution 3, Variation A: Use all Data to Estimate Cutoff Dropout/Dropin $$\hat{c}, \hat{p}_d, \hat{p}_a = \underset{c, p_d, p_a}{\operatorname{argmax}} f(p_d) f(p_a) \prod_j P(D_j(c) \mid M_j, F_j, p_d, p_a)$$

$$P(n_j) = \sum_{(n^M, n^F) \in n_j} P(n^M, n^F \mid D_j(\hat{c}), M_j, F_j, \hat{p}_d, \hat{p}_a)$$

Solution 3, Variation B:

Theoretically, this is the optimal estimate for the copy number on chromosome j.

$$\hat{n}_j = \underset{n}{\operatorname{argmax}} \sum_{(n^M, n^F) \in n} \int \int f(p_d) f(p_a) P(D_j(\hat{c})) \mid n^M, n^F, M_j, F_j, p_d, p_a)$$

$$\prod_{l \neq j} P(D_j(\hat{c})) \mid n^M, n^F, M_l, F_l, p_d, p_a) dp_d dp_a$$

Estimating Dropout/Dropin Rates from Known Samples

For the sake of thoroughness, a brief discussion of dropout and dropin rates is given here. Since dropout and dropin rates are so important for the algorithm, it may be beneficial to analyze data with a known truth model to find out what the true dropout/dropin rates are. Note that there is no single tree dropout rate: it is a function of the cutoff threshold. That said, if highly reliable genomic data exists that can be used as a truth model, then it is possible to plot the dropout/dropin rates of MDA experiments as a function of the cutoff-threshold. Here a maximum likelihood estimation is used.

$$\hat{c}, \hat{p}_d, \hat{p}_a = \underset{c, p_d, p_a}{\operatorname{argmax}} \prod_{jk} P(\hat{g}_{jk}^{(c)} \mid g_{jk}, p_d, p_a)$$

In the above equation, $\hat{g}_{jk}^{(c)}$, is the genotype call on SNP k of chromosome j, using c as the cutoff threshold, while $g_{jk}$, is the true genotype as determined from a genomic sample. The above equation returns the most likely triple of cutoff, dropout, and dropin. It should be obvious to one skilled in the art how one can implement this technique without parent information using prior probabilities associated with the genotypes of each of the SNPs of the target cell that will not undermine the validity of the work, and this will not change the essence of the invention.

G Bayesian Plus Sperm Method

Another way to determine the number of copies of a chromosome segment in the genome of a target individual is described here. In one embodiment of the invention, the genetic data of a sperm from the father and crossover maps can be used to enhance the methods described herein. Throughout this description, it is assumed that there is a chromosome of interest, and all notation is with respect to that chromosome. It is also assumed that there is a fixed cutoff threshold for genotyping. Previous comments about the impact of cutoff threshold choice apply, but will not be made explicit here. In order to best phase the embryonic information, one should combine data from all blastomeres on multiple embryos simultaneously. Here, for ease of explication, it is assumed that there is just one embryo with no additional blastomeres. However, the techniques mentioned in various other sections regarding the use of multiple blastomeres for allele-calling translate in a straightforward manner here.

Notation 1. n is the chromosome copy number.
2. $n^M$ is the number of copies supplied to the embryo by the mother: 0, 1, or 2.
3. $n^F$ is the number of copies supplied to the embryo by the father: 0, 1, or 2.
4. $p_d$ is the dropout rate, and $f(p_d)$ is a prior on this rate.
5. $p_a$ is the dropin rate, and $f(p_a)$ is a prior on this rate.
6. D={$\hat{g}_k$} is the set of genotype measurements on the chromosome of the embryo. $\hat{g}_k$ is the genotype call on the k-th SNP (as opposed to the true value): one of AA, AB, BB, or NC (no-call). Note that the embryo may be aneuploid, in which case the true genotype at a SNP may be, for example, AAB, or even AAAB, but the genotype measurements will always be one of the four listed. (Note: elsewhere in this disclosure 'B' has been used to indicate a heterozygous locus. That is not the sense in which it is being used here. Here 'A' and 'B' are used to denote the two possible allele values that could occur at a given SNP.)

7. $M=\{g_k^M\}$ is the known true sequence of genotypes on the mother. $g_k^M$ is the genotype value at the k-th SNP.
8. $F=\{g_k^F\}$ is the known true sequence of genotypes on the father. $g_k^F$ is the genotype value at the k-th SNP.
9. $S=\{\hat{g}_k^S\}$ is the set of genotype measurements on a sperm from the father. $\hat{g}_k^S$ is the genotype call at the k-th SNP.
10. $(m_1,m_2)$ is the true but unknown ordered pair of phased haplotype information on the mother. $m_{1k}$ is the allele value at SNP k of the first haploid sequence. $m_{2k}$ is the allele value at SNP k of the second haploid sequence. $(m_1,m_2) \in M$ is used to indicate the set of phased pairs $(m_1,m_2)$ that are consistent with the known genotype M. Similarly, $(m_1,m_2) \in g_k^M$ is used to indicate the set of phased pairs that are consistent with the known genotype of the mother at SNP k.
11. $(f_1,f_2)$ is the true but unknown ordered pair of phased haplotype information on the father. $f_{1k}$ is the allele value at SNP k of the first haploid sequence. $f_{2k}$ is the allele value at SNP k of the second haploid sequence. $(f_1,f_2) \in F$ is used to indicate the set of phased pairs $(f_1,f_2)$ that are consistent with the known genotype F. Similarly, $(f_1,f_2) \in g_k^F$ is used to indicate the set of phased pairs that are consistent with the known genotype of the father at SNP k.
12. $s_1$ is the true but unknown phased haplotype information on the measured sperm from the father. $s_{1k}$ is the allele value at SNP k of this haploid sequence. It can be guaranteed that this sperm is euploid by measuring several sperm and selecting one that is euploid.
13. $\chi^M=\{\phi_1, \ldots, \phi_n M\}$ is the multiset of crossover maps that resulted in maternal contribution to the embryo on this chromosome. Similarly, $\chi^F=\{\theta_1, \ldots, \theta_n F\}$ is the multiset of crossover maps that results in paternal contribution to the embryo on this chromosome. Here the possibility that the chromosome may be aneuploid is explicitly modeled. Each parent can contribute zero, one, or two copies of the chromosome to the embryo. If the chromosome is an autosome, then euploidy is the case in which each parent contributes exactly one copy, i.e., $\chi^M=\{\phi_1\}$ and $\chi^F=\{\theta_1\}$. But euploidy is only one of the 3×3=9 possible cases. The remaining eight are all different kinds of aneuploidy. For example, in the case of maternal trisomy resulting from an M2 copy error, one would have $\chi^M=\{\phi_1\phi_1\}$ and $\chi^F=\{\theta_1\}$. In the case of maternal trisomy resulting from an M1 copy error, one would have $\chi^M=\{\phi_1,\phi_2\}$ and $\chi^F=\{\theta_1\}$. $(\chi^M,\chi^F) \in n$ will be used to indicate the set of sub-hypothesis pairs $(\chi^N,\chi^F)$ that are consistent with the copy number n. $\chi_k^M$ will be used to denote $\{\phi_{1,k}, \ldots, \phi_n M_k\}$, the multiset of crossover map values restricted to the k-th SNP, and similarly for $\chi^F$. $\chi_k^M(m_1,m_2)$ is used to mean the multiset of allele values $\{\phi_{1,k}(m_1,m_2), \ldots, \phi_n M_k(m_1,m_2)\} = \{m_{\phi_{1,k}}, \ldots, m_{\phi_n M_k}\}$. Keep in mind that $\phi_{l,k} \in \{1,2\}$.
14. $\psi$ is the crossover map that resulted in the measured sperm from the father. Thus $s_1=\psi(f_1,f_2)$. Note that it is not necessary to consider a crossover multiset because it is assumed that the measured sperm is euploid. $\psi_k$ will be used to denote the value of this crossover map at the k-th SNP.
15. Keeping in mind the previous two definitions, let $\{e_1^M, \ldots, e_n^M M\}$ be the multiset of true but unknown haploid sequences contributed to the embryo by the mother at this chromosome. Specifically, $e_l^M=\phi_l(m_1,m_2)$, where $\phi_l$ is the l-th element of the multiset $\chi^M$, and $e_{1k}^M$ is the allele value at the k-th snp. Similarly, let $\{e_1^F, \ldots, e_n^F\}$ be the multiset of true but unknown haploid sequences contributed to the embryo by the father at this chromosome. Then $e_l^F=\theta_l(f_1,f_2)$, where $\theta_l$ is the l-th element of the multiset $\chi^F$, and $f_{1k}^M$ is the allele value at the k-th SNP. Also, $\{e_1^M, \ldots, e_n^M M\}=\chi^M(m_1,m_2)$, and $\{e_1^F, \ldots, e_n^F\}=\chi^F(f_1,f_2)$ may be written.
16. $P(\hat{g}_k|\chi_k^M(m_1,m_2), \chi_k^F(f_1,f_2),p_d,p_c)$ denotes the probability of the genotype measurement on the embryo at SNP k given a hypothesized true underlying genotype on the embryo and given hypothesized underlying dropout and dropin rates. Note that $\chi_k^M(m_1,m_2)$ and $\chi_k^F(f_1,f_2)$ are both multisets, so are capable of expressing aneuploid genotypes. For example, $\chi_k^M(m_1,m_2)=\{A,A\}$ and $\chi_k^F(f_1,f_2)=\{B\}$ expresses the maternal trisomic genotype AAB.

Note that in this method, the measurements on the mother and father are treated as known truth, while in other places in this disclosure they are treated simply as measurements. Since the measurements on the parents are very precise, treating them as though they are known truth is a reasonable approximation to reality. They are treated as known truth here in order to demonstrate how such an assumption is handled, although it should be clear to one skilled in the art how the more precise method, used elsewhere in the patent, could equally well be used.

Solution $$\hat{n} = \underset{n}{\mathrm{argmax}} P(n, D, M, F, S)$$

$$P(n, D, M, F, S) = \sum_{(\chi^U, \chi^F) \in n} \sum_\psi P(\chi^M, \chi^F, \psi, D, M, F, S)$$

$$= \sum_{(\chi^M, \chi^F) \in n} P(\chi^M) P(\chi^F) \sum_\psi P(\psi) \int f(p_d) \int$$

$$f(p_a) \prod_k P(\hat{g}_k, g_k^M, g_k^F, \hat{g}_k^S \mid \chi_k^M, \chi_k^F, \psi_k, p_d, p_a)$$

$$dp_d dp_c$$

$$= \sum_{(\chi^M, \chi^F) \in n} P(\chi^M) P(\chi^F) \sum_\psi P(\psi) \int f(p_d) \int f(p_c) \times$$

$$\prod_k \sum_{(f_1,f_2)=0_k^F} P(f_1) P(f_2) P(\hat{g}_k^S \mid \psi_k(f_1, f_2), p_d, p_a)$$

$$\sum_{(m_1,m_2)=0_k^M} P(m_1) P(m_2) P(\hat{g}_k \mid \chi_k^M(m_1, m_2), \chi_k^F(f_1, f_2),$$

$$p_d, p_a) dp_d dp_a$$

How to calculate each of the probabilities appearing in the last equation above has been described elsewhere in this disclosure. A method to calculate each of the probabilities appearing in the last equation above has also been described elsewhere in this disclosure. Although multiple sperm can be added in order to increase reliability of the copy number call, in practice one sperm is typically sufficient. This solution is computationally tractable for a small number of sperm.

H Simplified Method Using Only Polar Homozygotes

In another embodiment of the invention, a similar method to determine the number of copies of a chromosome can be implemented using a limited subset of SNPs in a simplified approach. The method is purely qualitative, uses parental data, and focuses exclusively on a subset of SNPs, the so-called polar homozygotes (described below). Polar homozygotic denotes the situation in which the mother and father are both homozygous at a SNP, but the homozygotes are opposite, or different allele values. Thus, the mother could be AA and the father BB, or vice versa. Since the actual allele values are not important—only their relationship to each other, i.e. opposites—the mother's alleles will be referred to as MM, and the father's as FF. In such a situation, if the embryo is euploid, it must be heterozygous at that allele. However, due to allele dropouts, a heterozygous SNP in the embryo may not be called as heterozygous. In fact, given the high rate of dropout associated with single cell amplification, it is far more likely to be called as either MM or FF, each with equal probability.

In this method, the focus is solely on those loci on a particular chromosome that are polar homozygotes and for which the embryo, which is therefore known to be heterozygous, but is nonetheless called homozygous. It is possible to form the statistic |MM|/(|MM|+|FF|), where |MM| is the number of these SNPs that are called MM in the embryo and |FF| is the number of these SNPs that are called FF in the embryo.

Under the hypothesis of euploidy, |MM|/(|MM|+|FF|) is Gaussian in nature, with mean ½ and variance ¼N, where N=(|MM|+|FF|). Therefore the statistic is completely independent of the dropout rate, or, indeed, of any other factors. Due to the symmetry of the construction, the distribution of this statistic under the hypothesis of euploidy is known.

Under the hypothesis of trisomy, the statistic will not have a mean of ½. If, for example, the embryo has MMF trisomy, then the homozygous calls in the embryo will lean toward MM and away from FF, and vice versa. Note that because only loci where the parents are homozygous are under consideration, there is no need to distinguish M1 and M2 copy errors. In all cases, if the mother contributes 2 chromosomes instead of 1, they will be MM regardless of the underlying cause, and similarly for the father. The exact mean under trisomy will depend upon the dropout rate, p, but in no case will the mean be greater than ⅓, which is the limit of the mean as p goes to 1. Under monosomy, the mean would be precisely 0, except for noise induced by allele dropins.

In this embodiment, it is not necessary to model the distribution under aneuploidy, but only to reject the null hypothesis of euploidy, whose distribution is completely known. Any embryo for which the null hypothesis cannot be rejected at a predetermined significance level would be deemed normal.

In another embodiment of the invention, of the homozygotic loci, those that result in no-call (NC) on the embryo contain information, and can be included in the calculations, yielding more loci for consideration. In another embodiment, those loci that are not homozygotic, but rather follow the pattern AA|AB, can also be included in the calculations, yielding more loci for consideration. It should be obvious to one skilled in the art how to modify the method to include these additional loci into the calculation.

I Reduction to Practice of the PS Method as Applied to Allele Calling

In order to demonstrate a reduction to practice of the PS method as applied to cleaning the genetic data of a target individual, and its associated allele-call confidences, extensive Monte-Carlo simulations were run. The PS method's confidence numbers match the observed rate of correct calls in simulation. The details of these simulations are given in separate documents whose benefits are claimed by this disclosure. In addition, this aspect of the PS method has been reduced to practice on real triad data (a mother, a father and a born child). Results are shown below in Table 8. The TAQ-MAN assay was used to measure single cell genotype data consisting of diploid measurements of a large buccal sample from the father (columns $p_1, p_2$), diploid measurements of a buccal sample from the mother $(m_1, m_2)$, haploid measurements on three isolated sperm from the father $(h_1, h_2, h_3)$, and diploid measurements of four single cells from a buccal sample from the born child of the triad. Note that all diploid data are unordered. All SNPs are from chromosome 7 and within 2 megabases of the CFTR gene, in which a defect causes cystic fibrosis.

The goal was to estimate (in E1,E2) the alleles of the child, by running PS on the measured data from a single child buccal cell (e1,e2), which served as a proxy for a cell from the embryo of interest. Since no maternal haplotype sequence was available, the three additional single cells of the child sample—(b11,b12), (b21,b22), (b22,b23), were used in the same way that additional blastomeres from other embryos are used to infer maternal haplotype once the paternal haplotype is determined from sperm. The true allele values (T1,T2) on the child are determined by taking three buccal samples of several thousand cells, genotyping them independently, and only choosing SNPs on which the results were concordant across all three samples. This process yielded 94 concordant SNPs. Those loci that had a valid genotype call, according to the ABI 7900 reader, on the child cell that represented the embryo, were then selected. For each of these 69 SNPs, the disclosed method determined de-noised allele calls on the embryo $(E_1, E_2)$, as well as the confidence associated with each genotype call.

Twenty (29%) of the 69 raw allele calls in uncleaned genetic data from the child cell were incorrect (shaded in column e1 and e2, Table 8). Columns $(E_1, E_2)$ show that PS corrected 18 of these (shaded in column E1 and E1, but not in column 'conf', Table 8), while two remained miscalled (2.9% error rate; shaded in column 'conf', Table 8). Note that the two SNPs that were miscalled had low confidences of 53.8% and 74.4%. These low confidences indicate that the calls might be incorrect, due either to a lack of data or to inconsistent measurements on multiple sperm or "blastomeres." The confidence in the genotype calls produced is an integral part of the PS report. Note that this demonstration, which sought to call the genotype of 69 SNPs on a chromosome, was more difficult than that encountered in practice, where the genotype at only one or two loci will typically be of interest, based on initial screening of parents' data. In some embodiments, the disclosed method may achieve a higher level of accuracy at loci of interest by: i) continuing to measure single sperm until multiple haploid allele calls have been made at the locus of interest; ii) including additional blastomere measurements; iii) incorporating maternal haploid data from extruded polar bodies, which are commonly biopsied in pre-implantation genetic diagnosis today. It should be obvious to one skilled in the art that there exist other modifications to the method that can also increase the level of accuracy, as well as how to implement these, without changing the essential concept of the disclosure.

J Reduction to Practice of the PS Method as Applied to Calling Aneliploidy

To demonstrate the reduction to practice of certain aspects of the invention disclosed herein, the method was used to call aneuploidy on several sets of single cells. In this case, only selected data from the genotyping platform was used: the genotype information from parents and embryo. A simple genotyping algorithm, called "pie slice", was used, and it showed itself to be about 99.9% accurate on genomic data. It is less accurate on MDA data, due to the noise inherent in MDA. It is more accurate when there is a fairly high "dropout" rate in MDA. It also depends, crucially, on being able to model the probabilities of various genotyping errors in terms of parameters known as dropout rate and dropin rate.

The unknown chromosome copy numbers are inferred because different copy numbers interact differently with the dropout rate, dropin rate, and the genotyping algorithm. By creating a statistical model that specifies how the dropout rate, dropin rate, chromosome copy numbers, and genotype cutoff-threshold all interact, it is possible to use standard statistical inference methods to tease out the unknown chromosome copy numbers.

The method of aneuploidy detection described here is termed qualitative CNC, or qCNC for short, and employs the basic statistical inferencing methods of maximum-likelihood estimation, maximum-a-posteriori estimation, and Bayesian inference. The methods are very similar, with slight differences. The methods described here are similar to those described previously, and are summarized here for the sake of convenience.

Maximum Likelihood (ML)

Let $X_1, \ldots, X_n \sim f(x;\theta)$. Here the $X_i$ are independent, identically distributed random variables, drawn according to a probability distribution that belongs to a family of distributions parameterized by the vector θ. For example, the family of distributions might be the family of all Gaussian distributions, in which case $\theta=(\mu,\sigma)$ would be the mean and variance that determine the specific distribution in question. The problem is as follows: θ is unknown, and the goal is to get a good estimate of it based solely on the observations of the data $X_1, \ldots, X_n$. The maximum likelihood solution is given by $$\hat{\theta} = \operatorname*{argmax}_{\theta} \prod_i f(X_i; \theta)$$

Maximum A' Posteriori (MAP) Estimation

Posit a prior distribution $f(\theta)$ that determines the prior probability of actually seeing θ as the parameter, allowing us to write $X_1, \ldots, X_n \sim f(x|\theta)$. The MAP solution is given by $$\hat{\theta} = \operatorname*{argmax}_{\theta} f(\theta) \prod_i (f(X_i | \theta)$$

Note that the ML solution is equivalent to the MAP solution with a uniform (possibly improper) prior.

Bayesian Inference

Bayesian inference comes into play when $\theta=(\theta_1, \ldots, \theta_d)$ is multidimensional but it is only necessary to estimate a subset (typically one) of the parameters $\theta_j$. In this case, if there is a prior on the parameters, it is possible to integrate out the other parameters that are not of interest. Without loss of generality, suppose that $\theta_1$ is the parameter for which an estimate is desired. Then the Bayesian solution is given by:

$$\hat{\theta}_1 = \operatorname*{argmax}_{\theta_1} f(\theta_1) \int f(\theta_2) \ldots f(\theta_d) \prod_i (f(X_i | \theta) d\theta_2 \ldots d\theta_d$$

Copy Number Classification

Any one or some combination of the above methods may be used to determine the copy number count, as well as when making allele calls such as in the cleaning of embryonic genetic data. In one embodiment, the data may come from INFINIUM platform measurements $\{(x_{jk}, y_{jk})\}$, where $x_{jk}$ is the platform response on channel X to SNP k of chromosome j, and $y_{jk}$ is the platform response on channel Y to SNP k of chromosome j. The key to the usefulness of this method lies in choosing the family of distributions from which it is postulated that these data are drawn. In one embodiment, that distribution is parameterized by many parameters. These parameters are responsible for describing things such as probe efficiency, platform noise. MDA characteristics such as dropout, dropin, and overall amplification mean, and, finally, the genetic parameters: the genotypes of the parents, the true but unknown genotype of the embryo, and, of course, the parameters of interest: the chromosome copy numbers supplied by the mother and father to the embryo.

In one embodiment, a good deal of information is discarded before data processing. The advantage of doing this is that it is possible to model the data that remains in a more robust manner. Instead of using the raw platform data $\{(x_{jk}, y_{jk})\}$, it is possible to pre-process the data by running the genotyping algorithm on the data. This results in a set of genotype calls $(y_{jk})$, where $y_{jk} \in \{NC, AA, AB, BB\}$. NC stands for "no-call". Putting these together into the Bayesian inference paradigm above yields:

$$\hat{n}_j^M,$$

$$\hat{n}_j^F = \max_{n^M, n^F} \int \int f(p_d) f(p_a) \prod_k P(g_{jk} | n^M, n^F, M_j, F_j, p_d, p_a) dp_d dp_a$$

Explanation of the Notation:

$\hat{n}_j^N, \hat{n}_j^F$ are the estimated number of chromosome copies supplied to the embryo by the mother and father respectively. These should sum to 2 for the autosomes, in the case of euploidy, i.e., each parent should supply exactly 1 chromosome.

$p_d$ and $p_a$ are the dropout and dropin rates for genotyping, respectively. These reflect some of the modeling assumptions. It is known that in single-cell amplification, some SNPs "drop out", which is to say that they are not amplified and, as a consequence, do not show up when the SNP genotyping is attempted on the INFINIUM platform. This phenomenon is modeled by saying that each allele at each SNP "drops out" independently with probability $p_d$ during the MDA phase. Similarly, the platform is not a perfect measurement instrument. Due to measurement noise, the platform sometimes picks up a ghost signal, which can be modeled as a probability of dropin that acts independently at each SNP with probability $p_a$.

$M_j, F_j$ are the true genotypes on the mother and father respectively. The true genotypes are not known perfectly, but because large samples from the parents are genotyped, one may make the assumption that the truth on the parents is essentially known.

Probe Modeling

In one embodiment of the invention, platform response models, or error models, that vary from one probe to another can be used without changing the essential nature of the invention. The amplification efficiency and error rates caused by allele dropouts, allele dropins, or other factors, may vary between different probes. In one embodiment, an error transition matrix can be made that is particular to a given probe. Platform response models, or error models, can be relevant to a particular probe or can be parameterized according to the quantitative measurements that are performed, so that the response model or error model is therefore specific to that particular probe and measurement.

Genotyping

Genotyping also requires an algorithm with some built-in assumptions. Going from a platform response (x,y) to a genotype g requires significant calculation. It is essentially requires that the positive quadrant of the x/y plane be divided into those regions where AA, AB, BB, and NC will be called. Furthermore, in the most general case, it may be useful to have regions where AAA, AAB, etc., could be called for trisomies.

In one embodiment, use is made of a particular genotyping algorithm called the pie-slice algorithm, because it divides the positive quadrant of the x/y plane into three triangles, or "pie slices". Those (x,y) points that fall in the pie slice that hugs the X axis are called AA, those that fall in the slice that hugs the Y axis are called BB, and those in the middle slice are called AB. In addition, a small square is superimposed whose lower-left corner touches the origin. (x,y) points falling in this square are designated NC, because both x and y components have small values and hence are unreliable.

The width of that small square is called the no-call threshold and it is a parameter of the genotyping algorithm. In order for the dropin/dropout model to correctly model the error transition matrix associated with the genotyping algorithm, the cutoff threshold must be tuned properly. The error transition matrix indicates for each true-genotype/called-genotype pair, the probability of seeing the called genotype given the true genotype. This matrix depends on the dropout rate of the MDA and upon the no-call threshold set for the genotyping algorithm.

Note that a wide variety of different allele calling, or genotyping, algorithms may be used without changing the fundamental concept of the invention. For example, the no-call region could be defined by a many different shapes besides a square, such as for example a quarter circle, and the no call thresholds may vary greatly for different genotyping algorithms.

Results of Aneuploidy Calling Experiments

Presented here are experiments that demonstrate the reduction to practice of the method disclosed herein to correctly call ploidy of single cells. The goal of this demonstration was twofold: first, to show that the disclosed method correctly calls the cell's ploidy state with high confidence using samples with known chromosome copy numbers, both euploid and aneuploid, as controls, and second to show that the method disclosed herein calls the cell's ploidy state with high confidence using blastomeres with unknown chromosome copy numbers.

In order to increase confidences, the ILLUMINA INFINIUM II platform, which allows measurement of hundreds of thousands of SNPs was used. In order to run this experiment in the context of PGD, the standard INFINIUM II protocol was reduced from three days to 20 hours. Single cell measurements were compared between the full and accelerated INFINIUM II protocols, and showed ~85% concordance. The accelerated protocol showed an increase in locus drop-out (LDO) rate from <1% to 5-10%; however, because hundreds of thousands of SNPs are measured and because PS accommodates allele dropouts, this increase in LDO rate does not have a significant negative impact on the results.

The entire aneuploidy calling method was performed on eight known-euploid buccal cells isolated from two healthy children from different families, ten known-trisomic cells isolated from a human immortalized trisomic cell line, and six blastomeres with an unknown number of chromosomes isolated from three embryos donated to research. Half of each set of cells was analyzed by the accelerated 20-hour protocol, and the other half by the standard protocol. Note that for the immortalized trisomic cells, no parent data was available. Consequently, for these cells, a pair of pseudo-parental genomes was generated by drawing their genotypes from the conditional distribution induced by observation of a large tissue sample of the trisomic genotype at each locus.

Where truth was known, the method correctly called the ploidy state of each chromosome in each cell with high confidence. The data are summarized below in three tables. Each table shows the chromosome number in the first column, and each pair of color-matched columns represents the analysis of one cell with the copy number call on the left and the confidence with which the call is made on the right. Each row corresponds to one particular chromosome. Note that these tables contain the ploidy information of the chromosomes in a format that could be used for the report that is provided to the doctor to help in the determination of which embryos are to be selected for transfer to the prospective mother. (Note '1' may result from both monosomy and uniparental disomy.) Table 9 shows the results for eight known-euploid buccal cells; all were correctly found to be euploid with high confidences (>0.99). Table 10 shows the results for ten known-trisomic cells (trisomic at chromosome 21); all were correctly found to be trisomic at chromosome 21 and disomic at all other chromosomes with high confidences (>0.92). Table 11 shows the results for six blastomeres isolated from three different embryos. While no truth models exist for donated blastomeres, it is possible to look for concordance between blastomeres originating from a single embryo, however, the frequency and characteristics of mosaicism in human embryos are not currently known, and thus the presence or lack of concordance between blastomeres from a common embryo is not necessarily indicative of correct ploidy determination. The first three blastomeres are from one embryo (e1) and of those, the first two (e1b1 and e1b3) have the same ploidy state at all chromosomes except one. The third cell (e1b6) is complex aneuploid. Both blastomeres from the second embryo were found to be monosomic at all chromosomes. The blastomere from the third embryo was found to be complex aneuploid. Note that some confidences are below 90%, however, if the confidences of all aneuploid hypotheses are combined, all chromosomes are called either euploid or aneuploid with confidence exceeding 92.8%.

K Laboratory Techniques

There are many techniques available allowing the isolation of cells and DNA fragments for genotyping, as well as for the subsequent genotyping of the DNA. The system and method described here can be applied to any of these techniques, specifically those involving the isolation of fetal cells or DNA fragments from maternal blood, or blastomeres from embryos in the context of IVF. It can be equally applied to genomic data in silico, i.e. not directly measured from genetic material. In one embodiment of the system, this data can be acquired as described below. This description of techniques is not meant to be exhaustive, and it should be clear to one skilled in the arts that there are other laboratory techniques that can achieve the same ends.

Isolation of Cells

Adult diploid cells can be obtained from bulk tissue or blood samples. Adult diploid single cells can be obtained from whole blood samples using FACS, or fluorescence activated cell sorting. Adult haploid single sperm cells can also be isolated from a sperm sample using FACS. Adult haploid single egg cells can be isolated in the context of egg harvesting during IVF procedures.

Isolation of the target single cell blastomeres from human embryos can be done using techniques common in in vitro fertilization clinics, such as embryo biopsy. Isolation of target fetal cells in maternal blood can be accomplished using monoclonal antibodies, or other techniques such as FACS or density gradient centrifugation.

DNA extraction also might entail non-standard methods for this application. Literature reports comparing various methods for DNA extraction have found that in some cases novel protocols, such as the using the addition of N-lauroyl-sarcosine, were found to be more efficient and produce the fewest false positives.

Amplification of Genomic DNA

Amplification of the genome can be accomplished by multiple methods including: ligation-mediated PCR (LM-PCR), degenerate oligonucleotide primer PCR (DOP-PCR), and multiple displacement amplification (MDA). Of the three methods, DOP-PCR reliably produces large quantities of DNA from small quantities of DNA, including single copies of chromosomes; this method may be most appropriate for genotyping the parental diploid data, where data fidelity is critical. MDA is the fastest method, producing hundred-fold amplification of DNA in a few hours; this method may be most appropriate for genotyping embryonic cells, or in other situations where time is of the essence.

Background amplification is a problem for each of these methods, since each method would potentially amplify contaminating DNA. Very tiny quantities of contamination can irreversibly poison the assay and give false data. Therefore, it is critical to use clean laboratory conditions, wherein pre- and post-amplification workflows are completely, physically separated. Clean, contamination free workflows for DNA amplification are now routine in industrial molecular biology, and simply require careful attention to detail.

Genotyping Assay and Hybridization

The genotyping of the amplified DNA can be done by many methods including MOLECULAR INVERSION PROBES (MIPs) such as AFFYMETRIX's GENFLEX TAG array, microarrays such as AFFYMETRIX's 500K array or the ILLUMINA BEAD ARRAYS, or SNP genotyping assays such as APPLIEDBIOSCIENCE's TAQMAN assay. The AFFYMETRIX 500K array, MIPs/GENFLEX, TAQMAN and ILLUMINA assay all require microgram quantities of DNA, so genotyping a single cell with either workflow would require some kind of amplification. Each of these techniques has various tradeoffs in terms of cost, quality of data, quantitative vs. qualitative data, customizability, time to complete the assay and the number of measurable SNPs, among others. An advantage of the 500K and ILLUMINA arrays are the large number of SNPs on which it can gather data, roughly 250,000, as opposed to MIPs which can detect on the order of 10,000 SNPs, and the TAQMAN assay which can detect even fewer. An advantage of the MIPs, TAQMAN and ILLUMINA assay over the 500K arrays is that they are inherently customizable, allowing the user to choose SNPs, whereas the 500K arrays do not permit such customization.

In the context of pre-implantation diagnosis during IVF, the inherent time limitations are significant; in this case it may be advantageous to sacrifice data quality for turn-around time. Although it has other clear advantages, the standard MIPs assay protocol is a relatively time-intensive process that typically takes 2.5 to three days to complete. In MIPs, annealing of probes to target DNA and post-amplification hybridization are particularly time-intensive, and any deviation from these times results in degradation in data quality. Probes anneal overnight (12-16 hours) to DNA sample. Post-amplification hybridization anneals to the arrays overnight (12-16 hours). A number of other steps before and after both annealing and amplification bring the total standard timeline of the protocol to 2.5 days. Optimization of the MIPs assay for speed could potentially reduce the process to fewer than 36 hours. Both the 500K arrays and the ILLUMINA assays have a faster turnaround: approximately 1.5 to two days to generate highly reliable data in the standard protocol. Both of these methods are optimizable, and it is estimated that the turn-around time for the genotyping assay for the 500 k array and/or the ILLUMINA assay could be reduced to less than 24 hours. Even faster is the TAQMAN assay which can be run in three hours. For all of these methods, the reduction in assay time will result in a reduction in data quality, however that is exactly what the disclosed invention is designed to address.

Naturally, in situations where the timing is critical, such as genotyping a blastomere during IVF, the faster assays have a clear advantage over the slower assays, whereas in cases that do not have such time pressure, such as when genotyping the parental DNA before IVF has been initiated, other factors will predominate in choosing the appropriate method. For example, another tradeoff that exists from one technique to another is one of price versus data quality. It may make sense to use more expensive techniques that give high quality data for measurements that are more important, and less expensive techniques that give lower quality data for measurements where the fidelity is not as critical. Any techniques which are developed to the point of allowing sufficiently rapid high-throughput genotyping could be used to genotype genetic material for use with this method.

Methods for Simultaneous Targeted Locus Amplification and Whole Genome Amplification.

During whole genome amplification of small quantities of genetic material, whether through ligation-mediated PCR (LM-PCR), multiple displacement amplification (MDA), or other methods, dropouts of loci occur randomly and unavoidably. It is often desirable to amplify the whole genome non-specifically, but to ensure that a particular locus is amplified with greater certainty. It is possible to perform simultaneous locus targeting and whole genome amplification.

In a preferred embodiment, the basis for this method is to combine standard targeted polymerase chain reaction (PCR) to amplify particular loci of interest with any generalized whole genome amplification method. This may include, but is not limited to: preamplification of particular loci before generalized amplification by MDA or LM-PCR, the addition of targeted PCR primers to universal primers in the generalized PCR step of LM-PCR, and the addition of targeted PCR primers to degenerate primers in MDA.

L Notes

As noted previously, given the benefit of this disclosure, there are more embodiments that may implement one or more of the systems, methods, and features, disclosed herein.

In all cases concerning the determination of the probability of a particular qualitative measurement on a target individual based on parent data, it should be obvious to one skilled in the art, after reading this disclosure, how to apply a similar method to determine the probability of a quantitative measurement of the target individual rather than qualitative. Wherever genetic data of the target or related individuals is treated qualitatively, it will be clear to one skilled in the art, after reading this disclosure, how to apply the techniques disclosed to quantitative data.

It should be obvious to one skilled in the art that a plurality of parameters may be changed without changing the essence of the invention. For example, the genetic data may be obtained using any high throughput genotyping platform, or it may be obtained from any genotyping method, or it may be simulated, inferred or otherwise known. A variety of computational languages could be used to encode the algorithms described in this disclosure, and a variety of computational platforms could be used to execute the calculations. For example, the calculations could be executed using personal computers, supercomputers, a massively parallel computing platform, or even non-silicon based computational platforms such as a sufficiently large number of people armed with abacuses.

Some of the math in this disclosure makes hypotheses concerning a limited number of states of aneuploidy. In some cases, for example, only monosomy, disomy and trisomy are explicitly treated by the math. It should be obvious to one skilled in the art how these mathematical derivations can be expanded to take into account other forms of aneuploidy, such as nullsomy (no chromosomes present), quadrosomy, etc., without changing the fundamental concepts of the invention.

When this disclosure discusses a chromosome, this may refer to a segment of a chromosome, and when a segment of a chromosome is discussed, this may refer to a full chromosome. It is important to note that the math to handle a segment of a chromosome is the same as that needed to handle a full chromosome. It should be obvious to one skilled in the art how to modify the method accordingly It should be obvious to one skilled in the art that a related individual may refer to any individual who is genetically related, and thus shares haplotype blocks with the target individual. Some examples of related individuals include: biological father, biological mother, son, daughter, brother, sister, half-brother, half-sister, grandfather, grandmother, uncle, aunt, nephew, niece, grandson, granddaughter, cousin, clone, the target individual himself/herself/itself, and other individuals with known genetic relationship to the target. The term 'related individual' also encompasses any embryo, fetus, sperm, egg, blastomere, blastocyst, or polar body derived from a related individual.

It is important to note that the target individual may refer to an adult, a juvenile, a fetus, an embryo, a blastocyst, a blastomere, a cell or set of cells from an individual, or from a cell line, or any set of genetic material. The target individual may be alive, dead, frozen, or in stasis.

It is also important to note that where the target individual refers to a blastomere that is used to diagnose an embryo, there may be cases caused by mosaicism where the genome of the blastomere analyzed does not correspond exactly to the genomes of all other cells in the embryo.

It is important to note that it is possible to use the method disclosed herein in the context of cancer genotyping and/or karyotyping, where one or more cancer cells is considered the target individual, and the non-cancerous tissue of the individual afflicted with cancer is considered to be the related individual. The non-cancerous tissue of the individual afflicted with the target could provide the set of genotype calls of the related individual that would allow chromosome copy number determination of the cancerous cell or cells using the methods disclosed herein.

It is important to note that the method described herein concerns the cleaning of genetic data, and as all living or once living creatures contain genetic data, the methods are equally applicable to any live or dead human, animal, or plant that inherits or inherited chromosomes from other individuals.

It is important to note that in many cases, the algorithms described herein make use of prior probabilities, and/or initial values. In some cases the choice of these prior probabilities may have an impact on the efficiency and/or effectiveness of the algorithm. There are many ways that one skilled in the art, after reading this disclosure, could assign or estimate appropriate prior probabilities without changing the essential concept of the patent.

It is also important to note that the embryonic genetic data that can be generated by measuring the amplified DNA from one blastomere can be used for multiple purposes. For example, it can be used for detecting aneuploidy, uniparental disomy, sexing the individual, as well as for making a plurality of phenotypic predictions based on phenotype-associated alleles. Currently, in IVF laboratories, due to the techniques used, it is often the case that one blastomere can only provide enough genetic material to test for one disorder, such as aneuploidy, or a particular monogenic disease. Since the method disclosed herein has the common first step of measuring a large set of SNPs from a blastomere, regardless of the type of prediction to be made, a physician, parent, or other agent is not forced to choose a limited number of disorders for which to screen. Instead, the option exists to screen for as many genes and/or phenotypes as the state of medical knowledge will allow. With the disclosed method, one advantage to identifying particular conditions to screen for prior to genotyping the blastomere is that if it is decided that certain loci are especially relevant, then a more appropriate set of SNPs which are more likely to cosegregate with the locus of interest, can be selected, thus increasing the confidence of the allele calls of interest.

It is also important to note that it is possible to perform haplotype phasing by molecular haplotyping methods. Because separation of the genetic material into haplotypes is challenging, most genotyping methods are only capable of measuring both haplotypes simultaneously, yielding diploid data. As a result, the sequence of each haploid genome cannot be deciphered. In the context of using the disclosed method to determine allele calls and/or chromosome copy number on a target genome, it is often helpful to know the maternal haplotype; however, it is not always simple to measure the maternal haplotype. One way to solve this problem is to measure haplotypes by sequencing single DNA molecules or clonal populations of DNA molecules. The basis for this method is to use any sequencing method to directly determine haplotype phase by direct sequencing of a single DNA molecule or clonal population of DNA molecules. This may include, but not be limited to: cloning amplified DNA fragments from a genome into a recombinant DNA constructs and sequencing by traditional dye-end terminator methods, isolation and sequencing of single molecules in colonies, and direct single DNA molecule or clonal DNA population sequencing using next-generation sequencing methods.

The systems, methods, and techniques of the present invention may be used to in conjunction with embyro screening or prenatal testing procedures. The systems, methods, and techniques of the present invention may be employed in methods of increasing the probability that the embryos and fetuses obtain by in vitro fertilization are successfully implanted and carried through the full gestation period. Further, the systems, methods, and techniques of the present invention may be employed in methods of decreasing the probability that the embryos and fetuses obtain by in vitro fertilization that are implanted and gestated are not specifically at risk for a congenital disorder.

Thus, according to some embodiments, the present invention extends to the use of the systems, methods, and techniques of the invention in conjunction with pre-implantation diagnosis procedures.

According to some embodiments, the present invention extends to the use of the systems, methods, and techniques of the invention in conjunction with prenatal testing procedures.

According to some embodiments, the systems, methods, and techniques of the invention are used in methods to decrease the probability for the implantation of an embryo specifically at risk for a congenital disorder by testing at least one cell removed from early embryos conceived by in vitro fertilization and transferring to the mother's uterus only those embryos determined not to have inherited the congenital disorder.

According to some embodiments, the systems, methods, and techniques of the invention are used in methods to decrease the probability for the implantation of an embryo specifically at risk for a chromosome abnormality by testing at least one cell removed from early embryos conceived by in vitro fertilization and transferring to the mother's uterus only those embryos determined not to have chromosome abnormalities.

According to some embodiments, the systems, methods, and techniques of the invention are used in methods to increase the probability of implanting an embryo obtained by in vitro fertilization that is at a reduced risk of carrying a congenital disorder.

According to some embodiments, the systems, methods, and techniques of the invention are used in methods to increase the probability of gestating a fetus.

According to preferred embodiments, the congenital disorder is a malformation, neural tube defect, chromosome abnormality, Down's syndrome (or trisomy 21), Trisomy 18, spina bifida, cleft palate, Tay Sachs disease, sickle cell anemia, thalassemia, cystic fibrosis, Huntington's disease, and/or fragile x syndrome. Chromosome abnormalities include, but are not limited to, Down syndrome (extra chromosome 21), Turner Syndrome (45X0) and Klinefelter's syndrome (a male with 2 X chromosomes).

According to preferred embodiments, the malformation is a limb malformation. Limb malformations include, but are not limited to, amelia, ectrodactyly, phocomelia, polymelia, polydactyly, syndactyly, polysyndactyly, oligodactyly, brachydactyly, achondroplasia, congenital aplasia or hypoplasia, amniotic band syndrome, and cleidocranial dysostosis.

According to preferred embodiments, the malformation is a congenital malformation of the heart. Congenital malformations of the heart include, but are not limited to, patent ductus arteriosus, atrial septal defect, ventricular septal defect, and tetralogy of fallot.

According to preferred embodiments, the malformation is a congenital malformation of the nervous system. Congenital malformations of the nervous system include, but are not limited to, neural tube defects (e.g., spina bifida, meningocele, meningomyelocele, encephalocele and anencephaly), Arnold-Chiari malformation, the Dandy-Walker malformation, hydrocephalus, microencephaly, megencephaly, lissencephaly, polymicrogyria, holoprosencephaly, and agenesis of the corpus callosum.

According to preferred embodiments, the malformation is a congenital malformation of the gastrointestinal system. Congenital malformations of the gastrointestinal system include, but are not limited to, stenosis, atresia, and imperforate anus.

According to some embodiments, the systems, methods, and techniques of the invention are used in methods to increase the probability of implanting an embryo obtained by in vitro fertilization that is at a reduced risk of carrying a predisposition for a genetic disease.

According to preferred embodiments, the genetic disease is either monogenic or multigenic. Genetic diseases include, but are not limited to, Bloom Syndrome, Canavan Disease, Cystic fibrosis, Familial Dysautonomia, Riley-Day syndrome, Fanconi Anemia (Group C), Gaucher Disease, Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease-juvenile, Connexin26, SMA, Rett syndrome, Phenylketonuria, Becker Muscular Dystrophy, Duchennes Muscular Dystrophy, Fragile X syndrome, Hemophilia A, Alzheimer dementia-early onset, Breast/Ovarian cancer, Colon cancer, Diabetes/MODY, Huntington disease, Myotonic Muscular Dystrophy, Parkinson Disease-early onset, Peutz-Jeghers syndrome, Polycystic Kidney Disease, Torsion Dystonia Combinations of the Aspects of the Invention As noted previously, given the benefit of this disclosure, there are more aspects and embodiments that may implement one or more of the systems, methods, and features, disclosed herein. Below is a short list of examples illustrating situations in which the various aspects of the disclosed invention can be combined in a plurality of ways. It is important to note that this list is not meant to be comprehensive; many other combinations of the aspects, methods, features and embodiments of this invention are possible.

In one embodiment of the invention, it is possible to combine several of the aspect of the invention such that one could perform both allele calling as well as aneuploidy calling in one step, and to use quantitative values instead of qualitative for both parts. It should be obvious to one skilled in the art how to combine the relevant mathematics without changing the essence of the invention.

In a preferred embodiment of the invention, the disclosed method is employed to determine the genetic state of one or more embryos for the purpose of embryo selection in the context of IVF. This may include the harvesting of eggs from the prospective mother and fertilizing those eggs with sperm from the prospective father to create one or more embryos. It may involve performing embryo biopsy to isolate a blastomere from each of the embryos. It may involve amplifying and genotyping the genetic data from each of the blastomeres. It may include obtaining, amplifying and genotyping a sample of diploid genetic material from each of the parents, as well as one or more individual sperm from the father. It may involve incorporating the measured diploid and haploid data of both the mother and the father, along with the measured genetic data of the embryo of interest into a dataset. It may involve using one or more of the statistical methods disclosed in this patent to determine the most likely state of the genetic material in the embryo given the measured or determined genetic data. It may involve the determination of the ploidy state of the embryo of interest. It may involve the determination of the presence of a plurality of known disease-linked alleles in the genome of the embryo. It may involve making phenotypic predictions about the embryo. It may involve generating a report that is sent to the physician of the couple so that they may make an informed decision about which embryo(s) to transfer to the prospective mother.

Another example could be a situation where a 44-year old woman undergoing IVF is having trouble conceiving. The couple arranges to have her eggs harvested and fertilized with sperm from the man, producing nine viable embryos. A blastomere is harvested from each embryo, and the genetic data from the blastomeres are measured using an ILLUMINA INFINIUM BEAD ARRAY. Meanwhile, the diploid data are measured from tissue taken from both parents also using the ILLUMINA INFINIUM BEAD ARRAY. Haploid data from the father's sperm is measured using the same method. The method disclosed herein is applied to the genetic data of the blastomere and the diploid maternal genetic data to phase the maternal genetic data to provide the maternal haplotype.

Those data are then incorporated, along with the father's diploid and haploid data, to allow a highly accurate determination of the copy number count for each of the chromosomes in each of the embryos. Eight of the nine embryos are found to be aneuploid, and the one embryo is found to be euploid. A report is generated that discloses these diagnoses, and is sent to the doctor. The report has data similar to the data found in Tables 9, 10 and 11. The doctor, along with the prospective parents, decides to transfer the euploid embryo which implants in the mother's uterus.

Another example may involve a pregnant woman who has been artificially inseminated by a sperm donor, and is pregnant. She is wants to minimize the risk that the fetus she is carrying has a genetic disease. She undergoes amniocentesis and fetal cells are isolated from the withdrawn sample, and a tissue sample is also collected from the mother. Since there are no other embryos, her data are phased using molecular haplotyping methods. The genetic material from the fetus and from the mother are amplified as appropriate and genotyped using the ILLUMINA INFINIUM BEAD ARRAY, and the methods described herein reconstruct the embryonic genotype as accurately as possible. Phenotypic susceptibilities are predicted from the reconstructed fetal genetic data and a report is generated and sent to the mother's physician so that they can decide what actions may be best.

Another example could be a situation where a racehorse breeder wants to increase the likelihood that the foals sired by his champion racehorse become champions themselves. He arranges for the desired mare to be impregnated by IVF, and uses genetic data from the stallion and the mare to clean the genetic data measured from the viable embryos. The cleaned embryonic genetic data allows the breeder to select the embryos for implantation that are most likely to produce a desirable racehorse.

TABLES 1-11

Table 1. Probability distribution of measured allele calls given the true genotype.
Table 2. Probabilities of specific allele calls in the embryo using the U and H notation.
Table 3. Conditional probabilities of specific allele calls in the embryo given all possible parental states.
Table 4. Constraint Matrix (A).
Table 5. Notation for the counts of observations of all specific embryonic allelic states given all possible parental states.
Table 6. Aneuploidy states (h) and corresponding $P(h|n_j)$, the conditional probabilities given the copy numbers.
Table 7. Probability of aneuploidy hypothesis (H) conditional on parent genotype.
Table 8. Results of PS algorithm applied to 69 SNPs on chromosome 7
Table 9. Aneuploidy calls on eight known euploid cells
Table 10. Aneuploidy calls on ten known trisomic cells
Table 11. Aneuploidy calls for six blastomeres.

TABLE 1

Probability distribution of measured allele calls given the true genotype.

| p(dropout) = 0.5, p(gain) = 0.02 | measured | | | |
|---|---|---|---|---|
| true | AA | AB | BB | XX |
| AA | 0.735 | 0.015 | 0.005 | 0.245 |
| AB | 0.250 | 0.250 | 0.250 | 0.250 |
| BB | 0.005 | 0.015 | 0.735 | 0.245 |

TABLE 2

Probabilities of specific allele calls in the embryo using the U and H notation.

| | Embryo readouts | | | |
|---|---|---|---|---|
| Embryo truth state | U | H | $\bar{U}$ | empty |
| U | $p_{11}$ | $p_{12}$ | $p_{13}$ | $p_{14}$ |
| H | $p_{21}$ | $p_{22}$ | $p_{23}$ | $p_{24}$ |

TABLE 3

Conditional probabilities of specific allele calls in the embryo given all possible parental states.

| Parental matings | Expected truth state in the embryo | Embryo readouts types and conditional probabilities | | | |
|---|---|---|---|---|---|
| | | U | H | $\bar{U}$ | empty |
| U×U | U | $p_{11}$ | $p_{12}$ | $p_{13}$ | $p_{14}$ |
| U×$\bar{U}$ | H | $p_{21}$ | $p_{22}$ | $p_{23}$ | $p_{24}$ |
| U×H | 50% U, 50% H | $p_{31}$ | $p_{32}$ | $p_{33}$ | $p_{34}$ |
| H×H | 25% U, 25% $\bar{U}$, 50% H | $p_{41}$ | $p_{42}$ | $p_{43}$ | $p_{44}$ |

TABLE 4

Constraint Matrix (A).

| 1 | 1 | 1 | 1 | | | | | | | | |
|---|---|---|---|---|---|---|---|---|---|---|---|
| | | | | 1 | 1 | 1 | 1 | | | | |
| | | | | 1 | | −1 | | | | | |
| −.5 | | | | | −.5 | | | 1 | | | |
| | −.5 | | | | −.5 | | | | 1 | | |
| | | −.5 | | | | −.5 | | | | 1 | |
| | | | −.5 | | | −.5 | | | | | 1 |
| −.25 | | −.25 | | −.5 | | | | | | 1 | |
| | −.5 | | | | −.5 | | | | | | 1 |
| −.25 | | −.25 | | | −.5 | | | | | | 1 |
| | | | | −.5 | | −.5 | | | | | 1 |

TABLE 5

Notation for the counts of observations of all specific embryonic allelic states given all possible parental states.

| Parental matings | Expected embryo truth state | Embryo readouts types and observed counts ||||
|---|---|---|---|---|---|
| | | U | H | $\bar{U}$ | Empty |
| UxU | U | $n_{11}$ | $n_{12}$ | $n_{13}$ | $n_{14}$ |
| Ux$\bar{U}$ | H | $n_{21}$ | $n_{22}$ | $n_{23}$ | $n_{24}$ |
| UxH | 50% U, 50% H | $n_{31}$ | $n_{32}$ | $n_{33}$ | $n_{34}$ |
| HxH | 25% U, 25% $\bar{U}$, 50% H | $n_{41}$ | $n_{42}$ | $n_{43}$ | $n_{44}$ |

TABLE 6

Aneuploidy states (h) and corresponding $P(h|n_j)$, the conditional probabilities given the copy numbers.

| N | H | P(h\|n) | In General |
|---|---|---|---|
| 1 | paternal monosomy | 0.5 | Ppm |
| 1 | maternal monosomy | 0.5 | Pmm |
| 2 | Disomy | 1 | 1 |
| 3 | paternal trisomy t1 | 0.5*pt1 | ppt*pt1 |
| 3 | paternal trisomy t2 | 0.5*pt2 | ppt*pt2 |
| 3 | maternal trisomy t1 | 0.5*pm1 | pmt*mt1 |
| 3 | maternal trisomy t2 | 0.5*pm2 | pmt*mt2 |

TABLE 7

Probability of aneuploidy hypothesis (H) conditional on parent genotype.

| | embryo allele counts | | hypothesis | (mother, father) genotype |||||||||
|---|---|---|---|---|---|---|---|---|---|---|---|---|
| copy # | nA | nC | H | AA,AA | AA,AC | AA,CC | AC,AA | AC,AC | AC,CC | CC,AA | CC,AC | CC,CC |
| 1 | 1 | 0 | father only | 1 | 1 | 1 | 0.5 | 0.5 | 0.5 | 0 | 0 | 0 |
| 1 | 1 | 0 | mother only | 1 | 0.5 | 0 | 1 | 0.5 | 0 | 1 | 0.5 | 0 |
| 1 | 0 | 1 | father only | 0 | 0 | 0 | 0 | 0.5 | 0.5 | 1 | 1 | 1 |
| 1 | 0 | 1 | mother only | 0 | 0.5 | 1 | 0.5 | 0.5 | 1 | 0 | 0.5 | 1 |
| 2 | 2 | 0 | disomy | 1 | 0.5 | 0 | 0.5 | 0.25 | 0 | 0 | 0 | 0 |
| 2 | 1 | 1 | disomy | 0 | 0.5 | 1 | 0.5 | 0.5 | 0.5 | 1 | 0.5 | 0 |
| 2 | 0 | 2 | disomy | 0 | 0 | 0 | 0 | 0.25 | 0.5 | 0 | 0.5 | 1 |
| 3 | 3 | 0 | father t1 | 1 | 0.5 | 0 | 0 | 0 | 0 | 0 | 0 | 0 |
| 3 | 3 | 0 | father t2 | 1 | 0.5 | 0 | 0.5 | 0.25 | 0 | 0 | 0 | 0 |
| 3 | 3 | 0 | mother t1 | 1 | 0 | 0 | 0.5 | 0 | 0 | 0 | 0 | 0 |
| 3 | 3 | 0 | mother t2 | 1 | 0.5 | 0 | 0.5 | 0.25 | 0 | 0 | 0 | 0 |
| 3 | 2 | 1 | father t1 | 0 | 0.5 | 1 | 1 | 0.5 | 0 | 0 | 0 | 0 |
| 3 | 2 | 1 | father t2 | 0 | 0.5 | 1 | 0 | 0.25 | 0.5 | 0 | 0 | 0 |
| 3 | 2 | 1 | mother t1 | 0 | 1 | 0 | 0.5 | 0.5 | 0 | 1 | 0 | 0 |
| 3 | 2 | 1 | mother t2 | 0 | 0 | 0 | 0.5 | 0.25 | 0 | 1 | 0.5 | 0 |
| 3 | 1 | 2 | father t1 | 0 | 0 | 0 | 0 | 0.5 | 1 | 1 | 0.5 | 0 |
| 3 | 1 | 2 | father t2 | 0 | 0 | 0 | 0.5 | 0.25 | 0 | 1 | 0.5 | 0 |
| 3 | 1 | 2 | mother t1 | 0 | 0 | 1 | 0 | 0.5 | 0.5 | 0 | 1 | 0 |
| 3 | 1 | 2 | mother t2 | 0 | 0.5 | 1 | 0 | 0.25 | 0.5 | 0 | 0 | 0 |
| 3 | 0 | 3 | father t1 | 0 | 0 | 0 | 0 | 0 | 0 | 0 | 0.5 | 1 |
| 3 | 0 | 3 | father t2 | 0 | 0 | 0 | 0 | 0.25 | 0.5 | 0 | 0.5 | 1 |
| 3 | 0 | 3 | mother t1 | 0 | 0 | 0 | 0 | 0 | 0.5 | 0 | 0 | 1 |
| 3 | 0 | 3 | mother t2 | 0 | 0 | 0 | 0 | 0.25 | 0.5 | 0 | 0.5 | 1 |

TABLE 8

Results of PS algorithm applied to 69 SNPs on chromosome 7

| probe_id | snp_id | p1 | p2 | m1 | m2 | b11 | b12 | b21 | b22 | b31 | b32 | h1 | h2 | h3 | e1 | e2 | T1 | T2 | E1 | E2 | conf |
|---|---|---|---|---|---|---|---|---|---|---|---|---|---|---|---|---|---|---|---|---|---|
| 80 | C_2972977_10 | A | A | A | A | A | A | A | X | X | A | A | X | A | A | A | A | A | A | A | 0.9983 |
| 81 | C_2972981_10 | T | T | T | T | X | X | X | X | X | X | X | T | T | T | T | T | T | T | T | 0.9775 |
| 98 | C_11611980_10 | G | A | A | A | A | A | G | G | X | X | G | X | X | G | A | A | G | A | A | 0.9890 |
| 26 | C_2280961_1_ | G | C | G | C | X | X | X | X | X | X | X | X | | | | G | C | | | |
| 8 | C_341386_1_ | C | C | C | C | X | X | C | C | C | C | X | C | C | C | C | C | C | C | C | 0.9985 |
| 9 | C_341387_1_ | C | C | C | C | X | C | C | C | C | C | X | C | C | C | C | C | C | C | C | 0.9988 |
| 71 | C_2606775_1_ | G | G | G | G | X | X | X | X | X | X | X | G | G | G | G | G | G | G | G | 0.9851 |
| 72 | C_2606779_1_ | G | G | G | G | X | X | G | G | G | X | G | X | G | G | G | G | G | G | G | 0.9972 |
| 27 | C_2280966_10 | T | A | T | A | X | X | X | X | X | X | X | X | | | | A | A | | | 0.9211 |
| 73 | C_2606790_10 | T | C | T | C | X | X | T | T | X | X | X | X | | | | T | C | | | 0.9917 |
| 105 | C_22273192_10 | G | G | G | A | X | X | G | G | G | G | A | G | G | X | X | G | A | G | A | |
| 106 | C_25619317_10 | A | A | A | A | X | A | A | X | A | X | X | X | X | A | A | A | A | A | A | 0.9940 |
| 64 | C_2559556_10 | G | G | T | G | X | X | T | T | X | X | G | G | X | | | G | T | G | G | 0.9798 |
| 20 | C_2258563_20 | T | T | T | C | C | C | X | X | X | X | T | X | T | | | C | C | | | 0.9324 |
| 49 | C_2546376_1_ | A | A | G | A | G | G | X | X | G | A | A | X | A | | | A | G | A | A | 0.9887 |
| 50 | C_2546377_20 | G | A | G | A | G | G | X | X | G | A | X | X | A | G | A | G | A | G | A | 0.9668 |
| 21 | C_2258567_10 | T | C | T | C | X | X | X | X | X | X | X | C | X | T | C | T | C | T | C | 0.8924 |
| 52 | C_2546385_10 | T | T | T | A | X | X | A | A | X | X | T | X | T | | | T | A | T | A | 0.9283 |

TABLE 8-continued

Results of PS algorithm applied to 69 SNPs on chromosome 7

| 53 | C_2546435_1_ | C | C | C | C | C | C | C | C | C | C | C | C | C | C | C | C | C | C | 0.9994 |
|---|---|---|---|---|---|---|---|---|---|---|---|---|---|---|---|---|---|---|---|---|
| 104 | C_16163603_10 | T | C | T | C | T | C | X | X | X | X | X | X | X | T | C | T | C | T | C | 0.9840 |
| 92 | C_8966543_10 | A | A | G | A | A | A | G | G | X | X | X | A | X |   | G | A | G | A | 0.8622 |
| 96 | C_11436986_10 | G | A | G | A | X | X | G | A | G | A | X | G | G | G | A | G | A | G | A | 0.9977 |
| 82 | C_2982699_10 | A | A | G | A | A | A | A | A | X | A | A | A | A | A | A | A | A | A | 0.9292 |
| 99 | C_15796183_10 | A | A | C | A | A | A | A | A | A | A | A | A | A | A | A | A | A | A | 0.9705 |
| 43 | C_2546319_10 | T | T | T | T | T | T | T | T | T | T | X | T | X | T | T | T | T | T | 0.9992 |
| 44 | C_2546335_20 | T | C | T | T | T | T | X | X | X | X | T | X | T | T | T | T | T | T | 0.8508 |
| 45 | C_2546344_10 | T | T | T | T | X | X | T | T | T | T | T | T | X | T | T | T | T | T | 0.9961 |
| 46 | C_2546353_1_ | T | T | T | C | X | X | T | T | X | X | T | T | T |   | T | C | T | C | 0.9346 |
| 56 | C_2555662_10 | T | C | T | C | X | X | C | C | X | X | C | C | C |   | T | C | C | T | 0.9328 |
| 57 | C_2555670_10 | T | C | T | T | T | T | T | T | T | C | T | X | T |   | T | C | T | C | 0.9604 |
| 58 | C_2555685_10 | T | C | T | T | T | T | T | T | T | T | C | C | T | T | T | T | T | T | 0.9982 |
| 59 | C_2555706_10 | A | A | G | A | A | X | X | A | A | X | G | G | A | A | A | A | A | A | 0.9345 |
| 15 | C_1843560_10 | T | C | T | C | X | X | X | X | X | X | C | X | T |   | T | C | C | T | 0.9683 |
| 102 | C_16151234_10 | G | A | G | G | X | X | X | X | X | A | X | A | X | G |   | A | A | X | G | 0.9944 |
| 94 | C_11436903_10 | G | C | C | C | C | C | G | C | G | C | X | C | C |   | G | C | G | C | 0.9991 |
| 18 | C_2256696_20 | G | A | G | G | G | G | G | G | G | A | A | X | G | G | G | G | G | G | 0.9638 |
| 7 | C_328336_10 | T | T | T | T | T | T | X | X | X | X | X | T | T | T | T | T | T | 0.9927 |
| 37 | C_2543108_10 | T | G | G | G | X | X | G | G | G | G | X | T | G | G | G | G | G | G | 0.9976 |
| 107 | C_25632606_10 | A | A | A | A | A | X | X | A | A | A | X | A | A | A | A | A | A | A | 0.9984 |
| 38 | C_2543111_10 | T | C | C | C | C | C | X | X | C | C | X | C | C | C | C | C | C | C | 0.9948 |
| 40 | C_2543116_10 | T | C | T | T | X | X | T | T | T | T | T | C | C | T | T | T | T | T | 0.9977 |
| 86 | C_8852708_10 | T | C | C | C | X | X | C | C | C | C | X | X | X | C | C | C | C | C | C | 0.9317 |
| 67 | C_2602203_10 | A | A | C | A | A | A | X | X | A | A | X | A | A | A | A | A | A | A | 0.9187 |
| 24 | C_2279233_10 | T | C | C | C | C | C | X | X | C | C | X | T | T | C | C | C | C | C | 0.9968 |
| 68 | C_2602208_10 | A | A | A | A | A | X | X | X | X | X | X | A | A | A | A | A | A | 0.9937 |
| 69 | C_2602221_10 | T | G | T | T | X | X | X | X | X | X | X | X | T | T | T | T | T | T | 0.9810 |
| 14 | C_656774_1_ | G | A | A | A | X | X | A | A | X | X | X | X | A | A | A | A | A | A | 0.8485 |
| 85 | C_3021372_10 | G | A | G | G | G | G | G | X | X | G | A | A | G | G | G | G | G | G | 0.9973 |
| 83 | C_3021345_10 | A | A | A | A | X | X | A | A | X | X | X | X | A | A | A | A | A | A | 0.9955 |
| 12 | C_656644_20 | C | C | C | C | C | C | C | C | C | C | X | X | X | C | C | C | C | C | 0.9992 |
| 11 | C_656642_1_ | A | A | G | G | G | G | G | G | G | X | A | X | G | G | G | G | G | 0.7858 |
| 61 | C_2558137_10 | T | C | T | T | T | T | X | X | T | T | C | C | T | T | T | T | T | T | 0.9957 |
| 87 | C_8853467_10 | G | G | G | G | X | X | X | X | X | X | X | X | G | G | G | G | G | G | 0.9866 |
| 3 | C_17027_10 | T | T | T | T | T | T | T | T | X | X | T | T | T | T | T | T | T | T | 0.9959 |
| 28 | C_2540863_10 | T | C | C | C | T | T | T | X | X | X | X |   | T | C | C | T | 0.9561 |
| 31 | C_2540896_1_ | T | C | T | T | X | X | X | X | X | X | X | X |   | T | C | T | C | 0.9058 |
| 35 | C_2540935_10 | C | C | C | C | X | X | X | X | C | X | X | X | C | C | C | C | C | C | 0.9944 |
| 36 | C_2540940_10 | T | G | T | G | T | T | X | X | T | G | T | X | T |   | T | G | G | T | 0.9828 |
| 109 | C_25632779_10 | A | A | G | A | X | X | A | A | A | A | A | A | A | A | A | A | A | 0.9269 |
| 4 | C_75266_10 | T | C | C | C | X | X | X | X | X | X | X | X |   | T | C | C | T | 0.9954 |
| 76 | C_2668636_10 | A | A | G | A | A | A | A | A | A | A | A | A | A | A | A | A | A | 0.9689 |
| 77 | C_2668640_10 | T | T | G | G | T | T | T | T | T | X | X | T | T | T | T | T | T | 0.6498 |
| 22 | C_2259838_10 | G | C | G | G | G | G | X | X | G | C | G | G | G | C | G | C | G | C | 0.9988 |
| 23 | C_2259850_10 | A | A | G | A | X | X | A | A | A | X | X | A | A | A | A | A | A | A | 0.9289 |
| 10 | C_349428_10 | A | A | A | A | A | A | A | A | X | A | X | A | A | A | A | A | A | 0.9974 |
| 5 | C_321446_10 | T | T | T | G | X | X | T | T | X | X | T | T | T | T | T | T | T | T | 0.8457 |
| 42 | C_2545620_10 | A | A | A | A | A | X | X | A | A | X | X | A | A | A | A | A | A | 0.9944 |
| 19 | C_2258307_10 | G | G | G | A | G | G | G | G | G | X | X | X | G | G | G | G | G | G | 0.9684 |
| 90 | C_8853956_10 | G | G | G | A | X | X | G | G | X | X | G | X | X | G | G | G | G | G | 0.8460 |

TABLE 9

Aneuploidy calls on eight known euploid cells

| Chr# | Cell 1 | | Cell 2 | | Cell 3 | | Cell 4 | | Cell 5 | | Cell 6 | | Cell 7 | | Cell 8 | |
|---|---|---|---|---|---|---|---|---|---|---|---|---|---|---|---|---|
| 1 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 2 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 3 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 4 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 5 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 6 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 7 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 8 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 9 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 10 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 11 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |

TABLE 9-continued

Aneuploidy calls on eight known euploid cells

| 12 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 13 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 14 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 15 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 16 | 2 | 1.00000 | 2 | 0.99997 | 2 | 1.00000 | 2 | 1.00000 | 2 | 1.00000 | 2 | 1.00000 | 2 | 1.00000 | 2 | 1.00000 |
| 17 | 2 | 1.00000 | 2 | 0.99995 | 2 | 1.00000 | 2 | 1.00000 | 2 | 1.00000 | 2 | 1.00000 | 2 | 1.00000 | 2 | 1.00000 |
| 18 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 19 | 2 | 1.00000 | 2 | 0.99998 | 2 | 1.00000 | 2 | 1.00000 | 2 | 1.00000 | 2 | 1.00000 | 2 | 1.00000 | 2 | 1.00000 |
| 20 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 21 | 2 | 0.99993 | 2 | 1.00000 | 2 | 1.00000 | 2 | 1.00000 | 2 | 1.00000 | 2 | 1.00000 | 2 | 1.00000 | 2 | 1.00000 |
| 22 | 2 | 1.00000 | 2 | 1.00000 | 2 | 0.99040 | 2 | 1.00000 | 2 | 1.00000 | 2 | 1.00000 | 2 | 1.00000 | 2 | 0.99992 |
| X  | 2 | 0.99999 | 2 | 0.99994 | 2 | 1.00000 | 2 | 1.00000 | 2 | 1.00000 | 2 | 1.00000 | 2 | 1.00000 | 2 | 1.00000 |

TABLE 10

Aneuploidy calls on ten known trisomic cells

| Chr# | Cell 1 | | Cell 2 | | Cell 3 | | Cell 4 | | Cell 5 | | Cell 6 | | Cell 7 | | Cell 8 | | Cell 9 | | Cell 10 | |
|---|---|---|---|---|---|---|---|---|---|---|---|---|---|---|---|---|---|---|---|---|
| 1  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 2  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 3  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 4  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 5  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 6  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 7  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 0.92872 | 2 | 1.00000 |
| 8  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 9  | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 10 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 11 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 12 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 13 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 14 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 15 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 0.99998 | 2 | 1.00000 |
| 16 | 2 | 1.00000 | 2 | 1.00000 | 2 | 1.00000 | 2 | 1.00000 | 2 | 0.99999 | 2 | 1.00000 | 2 | 1.00000 | 2 | 1.00000 | 2 | 1.00000 | 2 | 1.00000 |
| 17 | 2 | 1.00000 | 2 | 1.00000 | 2 | 1.00000 | 2 | 1.00000 | 2 | 0.96781 | 2 | 1.00000 | 2 | 1.00000 | 2 | 1.00000 | 2 | 1.00000 | 2 | 1.00000 |
| 18 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 19 | 2 | 1.00000 | 2 | 1.00000 | 2 | 0.99999 | 2 | 1.00000 | 2 | 1.00000 | 2 | 1.00000 | 2 | 1.00000 | 2 | 1.00000 | 2 | 1.00000 | 2 | 1.00000 |
| 20 | 2 | 1.00000 | 2 | 1.00000 | 2 | 1.00000 | 2 | 1.00000 | 2 | 0.99997 | 2 | 1.00000 | 2 | 1.00000 | 2 | 1.00000 | 2 | 1.00000 | 2 | 1.00000 |
| 21 | 3 | 1.00000 | 3 | 1.00000 | 3 | 1.00000 | 3 | 1.00000 | 3 | 1.00000 | 3 | 1.00000 | 3 | 1.00000 | 3 | 1.00000 | 3 | 1.00000 | 3 | 1.00000 |
| 22 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 23 | 1 | 1.00000 | 1 | 1.00000 | 1 | 1.00000 | 1 | 1.00000 | 1 | 1.00000 | 1 | 1.00000 | 1 | 1.00000 | 1 | 1.00000 | 1 | 1.00000 | 1 | 1.00000 |

TABLE 11

Aneuploidy calls for six blastomeres.

| Chr# | e1b1 | | e1b3 | | e1b6 | | e2b1 | | e2b2 | | e3b2 | |
|---|---|---|---|---|---|---|---|---|---|---|---|---|
| 1  | 2 | 1.00000 | 2 | 1.00000 | 1 | 1.00000 | 1 | 1.00000 | 1 | 1.00000 | 3 | 1.00000 |
| 2  | 2 | 1.00000 | 2 | 1.00000 | 3 | 1.00000 | 1 | 1.00000 | 1 | 1.00000 | 2 | 0.99994 |
| 3  | 2 | 1.00000 | 2 | 1.00000 | 2 | 1.00000 | 1 | 1.00000 | 1 | 1.00000 | 3 | 1.00000 |
| 4  | 2 | 1.00000 | 2 | 1.00000 | 2 | 1.00000 | 1 | 1.00000 | 1 | 1.00000 | 3 | 1.00000 |
| 5  | 2 | 1.00000 | 2 | 1.00000 | 2 | 1.00000 | 1 | 1.00000 | 1 | 1.00000 | 3 | 0.99964 |
| 6  | 2 | 1.00000 | 2 | 1.00000 | 2 | 1.00000 | 1 | 1.00000 | 1 | 1.00000 | 3 | 1.00000 |
| 7  | 2 | 1.00000 | 2 | 1.00000 | 2 | 1.00000 | 1 | 1.00000 | 1 | 1.00000 | 3 | 0.99866 |
| 8  | 2 | 1.00000 | 2 | 1.00000 | 3 | 0.99966 | 1 | 1.00000 | 1 | 1.00000 | 3 | 1.00000 |
| 9  | 2 | 1.00000 | 2 | 1.00000 | 2 | 1.00000 | 1 | 1.00000 | 1 | 1.00000 | 3 | 0.99999 |
| 10 | 2 | 1.00000 | 2 | 1.00000 | 2 | 1.00000 | 1 | 1.00000 | 1 | 1.00000 | 1 | 1.00000 |
| 11 | 2 | 1.00000 | 2 | 1.00000 | 2 | 1.00000 | 1 | 1.00000 | 1 | 1.00000 | 2 | 0.99931 |

TABLE 11-continued

Aneuploidy calls for six blastomeres.

| | | | | | | | | | |
|---|---|---|---|---|---|---|---|---|---|
| 12 | | 2 | 1.00000 | | 1 | 1.00000 | | 1 | 1.00000 |
| 13 | | 2 | 1.00000 | 0.98982 | 1 | 1.00000 | | 2 | 0.99969 |
| 14 | | 2 | 1.00000 | 0.99991 | 1 | 1.00000 | | 3 | 1.00000 |
| 15 | | 2 | 1.00000 | 0.99986 | 1 | 1.00000 | | 3 | 0.99999 |
| 16 | | 3 | 0.98609 | 0.74890 | 1 | 1.00000 | | 2 | 0.94126 |
| 17 | | 2 | 1.00000 | 0.97983 | 1 | 1.00000 | | 2 | 1.00000 |
| 18 | | 2 | 1.00000 | 0.98367 | 1 | 1.00000 | | 1 | 1.00000 |
| 19 | | 2 | 1.00000 | 0.64546 | 1 | 1.00000 | | 3 | 1.00000 |
| 20 | | 2 | 1.00000 | 0.58327 | 1 | 1.00000 | | 2 | 0.95078 |
| 21 | 0.9995 | 2 | 1.00000 | 0.97594 | 1 | 1.00000 | | 1 | 0.99776 |
| 22 | | 2 | 0.98219 | 0.99217 | 1 | 1.00000 | 0.99989 | 2 | 1.00000 |
| 23 | | 3 | 1.00000 | 1.00000 | 1 | 1.00000 | | 3 | 0.99998 |
| 24 | 0.99122 | 1 | 0.99778 | 0.99999 | | | | | |

What is claimed is:

1. A method for determining a number of copies of a segment of a chromosome in the genome of a target individual, comprising:
   creating, on a computer, a plurality of copy number hypotheses specifying the number of copies of the chromosome segment that are present in the genome of the target individual;
   obtaining genetic data from (1) the target individual at a plurality of single nucleotide polymorphic loci on the chromosome segment which data comprises measurement errors that result from allele drop outs or allele drop ins at a subset of the plurality of loci and (2) one or more biological parents of the target individual at the plurality of loci;
   calculating, on a computer, a distribution of measurement errors for the obtained genetic data;
   creating, on a computer, for each of the hypotheses, a probability distribution of the expected genotypes of the target individual from (i) the obtained genetic data from the one or more biological parents, (ii) the probability of one or more crossovers that may have occurred during the formation of a gamete that contributed a copy of the chromosome segment to the target individual, and (iii) the distribution of measurement errors for the obtained genetic data;
   applying, on a computer, a technique selected from the group consisting of maximum a-posteriori estimation, maximum likelihood estimation, and Bayesian estimation to the obtained genetic data of the target individual and the probability distribution of the expected genotypes of the target individual to rank one or more of the hypotheses according to the data fit between the obtained genetic data of the target individual and the probability distribution of the expected genotypes of the target individual; and
   selecting the hypothesis that is ranked the highest, thereby determining the number of copies of the chromosome segment in the genome of a target individual.

2. The method of claim 1 wherein the genetic data from the target individual is obtained by measuring genetic material from the target individual selected from the group consisting of one cell, two cells, three cells, four cells, five cells, between six and ten cells, between eleven and twenty cells, from twenty to fifty cells, extracellular DNA found in maternal blood and combinations thereof.

3. The method of claim 2, wherein the target individual's genetic material has, as part of the obtaining step, been amplified using a technique selected from the group consisting of Polymerase Chain Reaction (PCR), ligation mediated PCR, Whole Genome Amplification, degenerative oligonucleotide primer PCR, Multiple Displacement Amplification, allele-specific amplification and combinations thereof.

4. The method of claim 1 further comprising:
   determining, on a computer, the probability of the genetic data of the target individual under each of the hypotheses using measurements of the target individual's genetic material, measurements of the one or more biological parent's genetic material, and a plurality of parameters whose values may differ from one experiment to another; and
   integrating, on a computer, the copy number hypothesis probabilities and the genetic data probabilities over the plurality of parameters.

5. The method of claim 1 where the determination of the number of copies of chromosome segments that are present in the target individual's genome further comprises screening for a chromosomal condition selected from the group consisting of euploidy, nullsomy, monosomy, uniparental disomy, trisomy, tetrasomy, other aneuploidy, unbalanced translocation, deletions, insertions, mosaicism, and combinations thereof.

6. The method of claim 1, wherein the target individual's genetic data have, as part of the obtaining step, been measured using a tool or technique selected from the group consisting of the MOLECULAR INVERSION PROBE (MIP) assay, genotyping microarrays, the TAQMAN SNP genotyping assay, the ILLUMINA genotyping system, other genotyping assays, fluorescent in situ hybridization (FISH), sequencing, other high through-put genotyping platforms, and combinations thereof.

7. The method of claim 1, wherein the target individual's genetic data have been measured by analyzing substances selected from the group consisting of one or more diploid cells from the target individual, one or more haploid cells from the target individual, one or more blastomeres from the target individual, extra-cellular genetic material found in the target individual, extra-cellular genetic material from the target individual found in maternal blood, cells from the target individual found in maternal blood, genetic material known to have originated from the target individual, and combinations thereof.

8. The method of claim 1, wherein the one or more biological parents' genetic data have been obtained by analyzing substances selected from the group consisting of the one or more biological parents' bulk diploid tissue, one or more diploid cells from the one or more biological parents, one or more haploid cells taken from the one or more biological parents, one or more embryos created from (a) gamete(s) from the one or more biological parents, one or more blastomeres taken from such an embryo, extra-cellular genetic material found in the one or more biological parents, genetic material known to have originated from the one or more biological parents, and combinations thereof.

9. The method of claim 1, wherein the genetic data from the one or more biological parents comprises measured genetic data from sperm from the father of the target individual.

10. The method of claim 1, wherein the genetic data from the one or more biological parents comprises maternal haplotypic genetic data, and the maternal haplotypic genetic data are determined by inference using diploid genetic data measured from one or more blastomeres, diploid genetic data from one or more parents, and haploid genetic data from the father.

11. The method of claim 1, wherein the genetic data from the one or more biological parents comprises maternal haplotypic genetic data, and the maternal haplotypic genetic data that are used in the method have been determined without the use of genetic data from a born child, and without the use of genetic data from a parent of the mother, and without making use of a haplotypic tissue sample from the mother.

12. The method of claim 1, wherein the method is run alongside or in conjunction with a method that makes allele calls at multiple loci of the target individual, and where both methods use the same cell, or group of cells, from the target individual as a source of genetic material.

13. The method of claim 1 further comprising computing the maximum likelihood hypothesis using a plurality of parameters whose values may differ from one experiment to another.

14. The method of claim 1, wherein the measurement errors comprise errors due to variation in amplification efficiency.

15. A method of calling alleles in a chromosome of a target individual, comprising:
obtaining, genetic data at (1) a plurality of single nucleotide polymorphic loci on the chromosome of the target individual which data comprises measurement errors that result from allele drop outs or allele drop ins at a subset of the plurality of loci and (2) the plurality of loci in one or more biological parents of the target individual;
creating, on a computer, a plurality of hypotheses specifying what alleles are present at the plurality of loci in the target individual;
calculating, on a computer, a distribution of measurement errors for the obtained genetic data;
creating, on a computer, for each of the hypotheses, a probability distribution of the expected genotypes of the target individual from (i) the obtained genetic data from the one or more biological parents, (ii) the probability of one or more crossovers that may have occurred during the formation of a gamete that contributed a copy of the chromosome to the target individual, and (iii) the distribution of measurement errors for the obtained genetic data;
applying, on a computer, a technique selected from the group consisting of maximum a-posteriori estimation, maximum likelihood estimation, and Bayesian estimation to the obtained genetic data of the target individual and the probability distribution of the expected genotypes of the target individual to rank one or more of the hypotheses according to the data fit between the obtained genetic data of the target individual and the probability distribution of the expect genotypes of the target individual; and
selecting the hypothesis that is ranked the highest, thereby making allele calls at the plurality of loci of the target individual.

16. The method of claim 15 wherein the genetic data from the target individual is obtained by measuring genetic material from the target individual selected from the group consisting of one cell, two cells, three cells, four cells, five cells, between six and ten cells, between eleven and twenty cells, from twenty to fifty cells, extracellular DNA found in maternal blood and combinations thereof.

17. The method of claim 15, wherein the target individual's genetic data have been measured by analyzing substances selected from the group consisting of one or more diploid cells from the target individual, one or more haploid cells from the target individual, one or more blastomeres from the target individual, extra-cellular genetic material found in the target individual, extra-cellular genetic material from the target individual found in maternal blood, cells from the target individual found in maternal blood, genetic material known to have originated from the target individual, and combinations thereof.

18. The method of claim 15, wherein the biological parent's genetic data have been measured by analyzing substances selected from the group consisting of the biological parent's bulk diploid tissue, one or more diploid cells from the biological parent, one or more haploid cells taken from the biological parent, one or more embryos created from a gamete(s) from the biological parent, one or more blastomeres taken from such an embryo, extra-cellular genetic material found in the biological parent, genetic material known to have originated from the biological parent, and combinations thereof.

19. The method of claim 15, wherein the target individual's genetic data have been measured using a tool or technique selected from the group consisting of the MOLECULAR INVERSION PROBE (MIP) assay, genotyping microarrays, the TAQMAN SNP genotyping assay, the ILLUMINA genotyping system, other genotyping assays, fluorescent in-situ hybridization (FISH), sequencing, other high through-put genotyping platforms, and combinations thereof.

20. The method of claim 15, wherein the method does not make use of short tandem repeats.

21. The method of claim 15, wherein the most likely allele calls of the target individual at the one or more alleles are calculated by determining which, if any of the homologous chromosome segments from each of the one or more of the biological parent(s), on which each of the one or more alleles are located, are genetically the same as those chromosome segments in the target individual.

22. The method of claim 15, wherein the genetic data from at least one biological parent comprises maternal haplotypic genetic data, and the maternal haplotypic genetic data are determined by inference using diploid genetic data measured from one or more blastomeres, diploid genetic data from one or more parents, and haploid genetic data from the father.

23. The method of claim 15, wherein the genetic data from at least one biological parent comprises maternal haplotypic genetic data, and the maternal haplotypic genetic data that are used in the method have been determined without the use of genetic data from a born child, and without the use of genetic data from a parent of the mother, and without making use of a haplotypic tissue sample from the mother.

24. The method of claim 15, where the genetic data of only one biological parent who is a carrier of the disease linked allele is used.

25. The method of claim 15, wherein the method is run alongside or in conjunction with a method that determines the number of copies of a given chromosome segment present in the target individual, and where both methods use the same cell, or group of cells, from the target individual as a source of genetic material.

26. The method of claim 15, where at least one of the one or more most likely correct allele calls is an allele associated with a disease.

* * * * *